United States Patent [19]

Pellet et al.

[11] Patent Number: 4,740,650
[45] Date of Patent: Apr. 26, 1988

[54] XYLENE ISOMERIZATION

[75] Inventors: Regis J. Pellet, Croton-On-Hudson; Gary N. Long, Putnam Valley; Jule A. Rabo, Armonk; Peter K. Coughlin, Yorktown, all of N.Y.

[73] Assignee: Union Carbide Corporation, Danbury, Conn.

[21] Appl. No.: 874,994

[22] Filed: Jun. 16, 1986

[51] Int. Cl.$^4$ .................................................. C07C 5/22
[52] U.S. Cl. .................................... 585/480; 585/481; 585/482
[58] Field of Search ...................... 585/480, 481, 482

[56] References Cited

U.S. PATENT DOCUMENTS

| | | | |
|---|---|---|---|
| 4,310,440 | 1/1982 | Wilson et al. | 585/467 |
| 4,440,871 | 4/1984 | Lok et al. | 585/467 |
| 4,500,651 | 2/1985 | Lok et al. | 502/164 |
| 4,508,836 | 4/1985 | Hzzq et al. | 585/481 |
| 4,554,143 | 11/1985 | Messina et al. | 585/482 |
| 4,567,029 | 1/1986 | Wilson et al. | 585/482 |

Primary Examiner—Curtis R. Davis
Attorney, Agent, or Firm—Gerald L. Coon

[57] ABSTRACT

Xylene isomerization is carried out using specific non-zeolitic molecular sieve catalyst, e.g., the silicoaluminophosphate molecular sieves of U.S. Pat. No. 4,440,871, to provide improved production of p-xylene from $C_8$ aromatic compounds and the conversion of ethylbenzene to a xylene.

30 Claims, 3 Drawing Sheets

XYLENE ISOMERIZATION

XYLENE ISOMERIZATION

FIELD OF THE INVENTION

The instant invention relates to xylene isomerization and to the process for carrying out the isomerization of xylenes in the presence of novel isomerization catalysts.

BACKGROUND OF THE INVENTION

Xylenes are found as a mixture of the o-xylene, m-xylene and p-xylene and are found as components in petroleum reformates, or coal pyrolysis tar distillates and the like. Xylenes are generally recovered and separated by solvent extraction, distillation and/or fractional crystallization. For example, p-xylene may be separated from other $C_8$ aromatics by fractional crystallization.

Although o-xylene, m-xylene and p-xylene are as useful as chemical reagents, solvents, etc., p-xylene is particularly valuable, since p-xylene finds wide use in the manufacture of polyester. As a result of this significant commercial interest in p-xylene several processes have been developed to provide p-xylene. One such process is Octafining. In Octafining a $C_8$ aromatics mixture is subjected to a series of processing separation steps involving isomerization of a $C_8$ fraction depleted in the desired $C_8$ product component which is then charged to the isomerizer unit and the effluent isomerizate $C_8$ aromatics recycled to a product separation step. The isomerizer unit in Octafining itself is most simply described as a single reactor catalytic converter. The catalyst usually contains a small amount of platinum and an acid component which can be mordenite, silica-alumina and the like, and the reaction is carried out in a hydrogen atmosphere.

Xylene isomerization includes processes for the isomerization of monocyclic methyl-substituted aromatic hydrocarbon feedstocks. Several processes are employed commercially for the isomerization and include, but are not limited to, "Octafining" and the "LTI" process. These processes are only two of the processes which may be employed for xylene isomerization.

The design of an Octafiner process unit is generally characterized in the literature by the following specification ranges:

|  | Process Conditions |
| --- | --- |
| Reactor Pressure | 175 to 225 PSIG |
| Reactor Inlet Temperature Range | 750-900° F. |
| Heat of Reaction | Nil |
| Liquid Hourly Space Velocity | 0.6 to 1.6 Vol/Vol/Hr. |
| Number of Reactors | 1 |
| Downflow |  |
| Catalyst | Pt/silica-alumina |
| Catalyst Bed Depth Feet | 11 to 15 |
| Catalyst Density Lb/Cu. Ft | 38 |
| Recycle Circulation Moles Hydrogen/Mol Hydrocarbon Feed | 7.0 to 14.0 |
| Maximum Catalyst Pressure Drop. PSI | 20 |

Octafining is extensively discussed in the literature as exemplified by the following:

1. Pitts, P. M. Connor, J. E., Leun, L. N., Ind. Eng. Chem, 47, 770 (1955).
2. Fowle, M. J. Bent, R. D., Milner, B. E., presented at the Fourth World Petroleum Congress, Rome, Italy, June 1955.
3. Ciapetta, F. G., U.S. Pat. No. 2,550,531.
4. Ciapetta, F. G., And Buck, W. H., U.S. Pat. No. 2,589,189.
5. Octafining Process, Process Issue, Petroleum Refinery, 1st Vol. 38 (1959), No. 11, Nov., p. 278.

The $C_8$ aromatics feed may be derived from petroleum derivatives, e.g., aromatic gasoline fractions from various processes, including solvent extraction. $C_8$ aromatics generally comprise ethylbenzene, o-xylene, m-xylene, and p-xylene in amounts of from 10 to 32 wt. % ethylbenzene, 50 wt. % m-xylene, up to 25 wt. % o-xylene and up to 25 wt. % p-xylene. Under the conditions commonly employed for Octafining the calculated thermodynamic equilibria for the various $C_8$ aromatic isomers are:

| Temperature | 850° F. |
| --- | --- |
| Wt. % ethylbenzene | 8.5 |
| Wt. % para-xylene | 22.0 |
| Wt. % meta-xylene | 48.0 |
| Wt % ortho-xylene | 21.5 |
| TOTAL | 100.0 |

It has been reported that an increase in temperature of 50° F. will increase the equilibrium concentration of ethylbenzene by about 1 wt %, ortho-xylene is not changed and para- and meta-xylenes are both decreased by about 0.5 wt %. (See: U.S. Pat. No. 4,158,676).

In Octafining the process is capable of converting a portion of the ethylbenzene to xylenes and, accordingly, some ethylbenzene can be present in the process. The various processing steps employed in Octafining are well known in the art and will not be further discussed here.

Low Temperature Isomerization (LTI) is described in U.S. Pat. No. 3,377,400, dated Apr. 9, 1968. The LTI process is characterized by the capability of isomerizing xylenes in the liquid phase at relatively low temperatures and without the necessity of having a hydrogen pressure in the isomerization reactor. The zeolite catalyst ages very slowly even without hydrogen or a hydrogenation/dehydrogenation metal component on the catalyst. However, LTI has one disadvantage in that it does not result in the conversion of ethylbenzene. Since the ethylbenzene content of $C_8$ aromatic fractions is relatively unchanged in LTI operations, such operations generally incur increased costs in capital investment and operating expenses since ethylbenzene must be removed from the process. Because of the minor differences in the boiling points of ethylbenzene and certain of the xylenes, complete removal of ethylbenzene from the charge is extremely expensive. The practical way to remove ethylbenzene is to provide an additional distillation column for removing ethylbenzene. Unfortunately, the incorporation of this additional distillation column involves a significant additional cost and increases the operating expenses for the process.

The instant process relates to novel isomerization catalysts and to their use in isomerization processes to prepare xylene mixtures which are isomerized to an substantially equilibrium distributions or higher in the para-product. In some embodiments meta-xylene is isomerized to para- and ortho-xylenes and/or ethylbenzene is converted to products, e.g., xylenes, to provide process products having a lower ethylbenzene content than the feedstock.

DETAILED DESCRIPTION OF THE INVENTION

Figure 1:
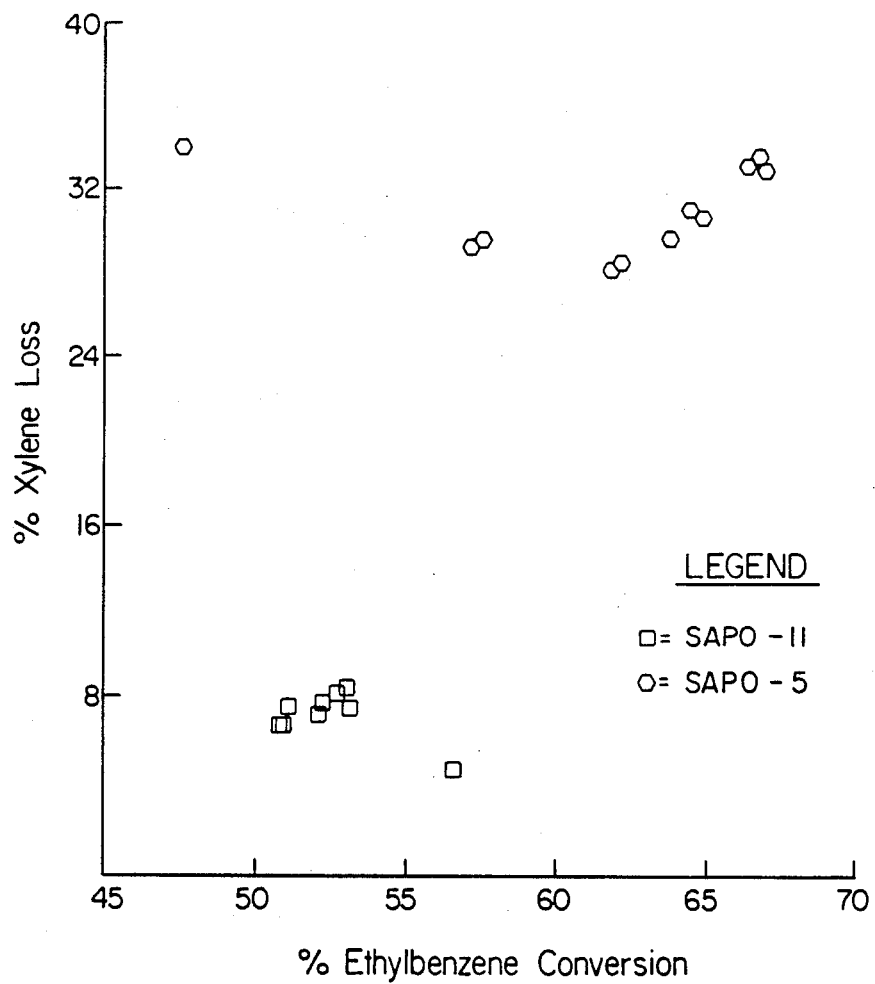
FIG. 1 is a plot of weight percent (wt. %) ethylbenzene conversion vs. wt. % xylenes loss for SAPO-5 and SAPO-11.

The instant invention relates to the isomerization of non-equilibriumxylene mixtures to obtain near equilibriumxylene mixtures or mixtures having increased paraxylene content. The invention also relates to conversion of ethylbenzene, if any, contained in such xylene mixtures whereby the amount of ethylbenzene present in the xylene mixtures (feedstocks) is decreased in the products. The invention employs novel catalysts comprising at least one non-zeolitic molecular sieve characterized in the calcined form by an adsorption of isobutane of at least 2 percent by weight, preferably at least 4 percent by weight (wt. %), at a partial pressure of 500 torr and a temperature of 20° C. and are also characterized by an adsorption of triethylamine less than 5 percent by weight, preferably less than 3 wt. %, at a partial pressure of 2.6 torr and a temperature of 22° C.

The non-zeolitic molecular sieves employed on the instant process are discussed hereinafter:

NON-ZEOLITIC MOLECULAR SIEVES ("NZMS")

The term "non-zeolitic molecular sieves" or "NZMS" is defined in the instant invention to include molecular sieves containing framework tetrahedral units ($TO_2$) of aluminum ($AlO_2$), phosphorus ($PO_2$) and at least one additional element (EL) as a framework tetrahedral unit ($EL_2$). "NZMS" includes the "SAPO" molecular sieves of U.S. Pat. No. 4,440,871, "ELAPSO" molecular sieves as disclosed in U.S. Ser. No. 600,312, filed Apr. 13, 1984 and certain "MeAPO", "FAPO", "TAPO" and "ELAPO" molecular sieves, as hereinafter described. Crystalline metal aluminophosphates (MeAPOs where "Me" is at least one of Mg, Mn, Co and Zn) are disclosed in U.S. Pat. No. 4,567,029, issued Jan. 28, 1986; crystalline ferroaluminophosphates (FAPOs) are disclosed in U.S. Pat. No. 4,554,143, issued Nov. 19, 1985; titanium aluminophosphates (TAPOs) are disclosed in U.S. Pat. No. 4,500,651, issued Feb. 19, 1985; certain non-zeolitic molecular sieves ("ELAPO") are disclosed U.S. in EPC Application No. 85104386.9 (Publication No. 0158976, published Oct. 13, 1985 and 85104388.5 (Publication No. 158349, published Oct. 16, 1985); and ELAPSO molecular sieves are disclosed in copending U.S. Ser. No. 600,312, filed Apr. 13, 1984 (EPC Publication No. 0159624, published Oct. 30, 1985). The aforementioned applications and patents are incorporated herein by reference thereto. The nomenclature employed herein to refer to the members of the aforementioned NZMSs is consistent with that employed in the aforementioned applications or patents. A particular member of a class is generally referred to as a "-n" species wherein "n" is an integer, e.g., SAPO- 11, MeAPO- 11 and ELAPSO- 31. In the following discussion on NZMSs set forth hereinafter the mole fraction of the NZMSs are defined as compositional values which are plotted in phase diagrams in each of the identified patents, published applications or copending applications.

ELAPSO MOLECULAR SIEVES

"ELAPSO" molecular sieves are described in copending U.S. Ser. No. 600,312, filed Apr. 13, 1984, (EPC Publication No. 0159,624, published Oct. 30, 1985, incorporated herein by reference) as crystalline molecular sieves having three-dimensional microporous framework structures of $ELO_2$, $AlO_2$, $PO_2$, $SiO_2$ oxide units and having an empirical chemical composition on an anhydrous basis expressed by the formula:

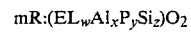

wherein "R" represents at least one organic templating agent present in the intracrystalline pore system; "m" represents the molar amount of "R" present per mole of $(EL_wAl_xP_ySi_z)O_2$ and has a value of from zero to about 0.3; "EL" represents at least one element capable of forming a three dimensional oxide framework, "EL" is characterized as an element having a mean "T-O" distance in tetrahedral oxide structures between about 1.51 Angstroms and about 2.06 Angstroms, "EL" has a cation electronegativity between about 125 kcal/g-atom to about 310 kcal/g-atom and "EL" is capable of forming stable M-O-P, M-O-Al or M-O-M bonds in crystalline three dimensional oxide structures having a "M-O" bond dissociation energy greater than about 59 kcal/g-atom at 298° K.; and "w", "lx", "y" and "z" represent the mole fractions of "EL", aluminum, phosphorus and silicon, respectively, present as framework oxides said mole fractions being within the limiting compositional values or points as follows:

| Point | Mole Fraction | | |
|---|---|---|---|
| | x | y | (z + w) |
| A | 0.60 | 0.39–(0.01)p | 0.01(p + 1) |
| B | 0.39–(0.01 p) | 0.60 | 0.01(p + 1 ) |
| C | 0.01 | 0.60 | 0.39 |
| D | 0.01 | 0.01 | 0.98 |
| E | 0.60 | 0.01 | 0.39 | where "p" is an integer corresponding to the number of elements "El" in the $(El_wAl_xP_ySi_z)O_2$ constituent.

The "ELAPSO" molecular sieves are also described as crystalline molecular sieves having three dimensional microporous framework structures of $ELO_2$, $AlO_2$, $SiO_2$ and $PO_2$ tetrahedral oxide units and having an empirical chemical composition on an anhydrous basis expressed by the formula:

wherein "R" represents at least one organic templating agent present in the intracrystalline pore system; "m" represents the molar amount of "R" present per mole of $(EL_wAl_xP_ySi_z)O_2$ and has a value of from zero to about 0.3; "EL" represents at least one element capable of forming a framework tetrahedral oxide and is selected from the group consisting of arsenic, beryllium, boron, chromium, cobalt, gallium, germanium, iron, lithium, magnesium, manganese, titanium and zinc; and "w", "x", "y" and "z" represent the mole fractions of "EL", aluminum, phosphorus and silicon, respectively, present as tetrahedral oxides said mole fractions being within the limiting compositional values or points as follows:

| Point | Mole Fraction | | |
|---|---|---|---|
| | x | y | (z + w) |
| a | 0.60 | 0.39–(0.01)p | 0.01(p + 1) |
| b | 0.39–(0.01 p) | 0.60 | 0.01(p + 1) |
| c | 0.10 | 0.55 | 0.35 |
| d | 0.55 | 0.10 | 0.35 | where "p" is as above defined.

The "ELAPSO" molecular sieves include numerous species which are intended herein to be within the scope of the term "non-zeolitic molecular sieves" such being disclosed in the following copending and commonly assigned applications, incorporated herein by reference thereto:

| U.S. Ser. No. | Filed | NZMS |
|---|---|---|
| 600,174 | April 13, 1984 | CoAPSO |
| 600,173 | April 13, 1984 now U.S. Pat. No. 4,683,217 | FeAPSO |
| 600,180 | April 13, 1984 | MgAPSO |
| 600,175 | April 13, 1984 now U.S. Pat. No. 4,686,092 | MnAPSO |
| 600,179 | April 13, 1984 now U.S. Pat. No. 4,684,617 | TiAPSO |
| 600,170 | April 13, 1984 | ZnAPSO |
| 600,168 | April 13, 1984 now abandoned | CoMgAPSO |
| 600,182 | April 13, 1984 now abandoned | CoMnMgAPSO |
| 845,984 | March 31, 1986 | AsAPSO |
| 845,255 | March 28, 1986 | BAPSO |
| 841,752 | March 20, 1986 | BeAPSO |
| 852,174 | April 15, 1986 | CAPSO |
| 845,985 | March 31, 1986 | GaAPSO |
| 852,175 | April 15, 1986 | GeAPSO |
| 847,227 | April 12, 1986 | LiAPSO |

TiAPSO MOLECULAR SIEVES

The TiAPSO molecular sieves of U.S. Ser. No. 600,179, filed Apr. 13, 1984 have three-dimensional microporous framework structures of $TiO_2$, $AlO_2$, $PO_2$ and $SiO_2$ tetrahedral oxide units having an empirical chemical composition on an anhydrous basis expressed by the formula:

$$mR:(Ti_wAl_xP_ySi_z)O_2$$

wherein "R" represents at least one organic templating agent present in the intracrystalline pore system; "m" represents the molar amount of "R" present per mole of $(Ti_wAl_xP_ySi_z)O_2$ and has a value of from zero to about 0.3; and "w", "x", "y" and "z" represent the mole fractions of titanium, aluminum, phosphorus and silicon, respectively, present as tetrahedral oxides and each has a value of at least 0.01. The mole fractions "w", "x", "y" and "z" are generally defined being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |

-continued

| Point | Mole Fraction | | |
|---|---|---|---|
| | x | y | (z + w) |
| D | 0.01 | 0.01 | 0.98 |
| E | 0.60 | 0.01 | 0.39 |

In a subclass of TiAPSO molecular sieves the values "w", "x", "y" and "z" in the above formula are within the tetragonal compositional area defined by points a, b, c and d, said points a, b, c and d representing the following values for "w", "x", "y" and "z":

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

TiAPSO compositions are generally synthesized by hydrothermal crystallization from a reaction mixture containing active resources of titanium, silicon, aluminum and phosphorus, and preferably an organic templating, i.e., structure-directing, agent, preferably a compound of an element or Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the TiAPSO product are obtained, usually a period of from hours to several weeks. Generally, the crystallization time is from about 2 hours to about 30 days and typically from about 4 hours to about 20 days. The product is recovered by any convenient method such as centrifugation or filtration.

In synthesizing the TiAPSO, it is preferred to employ a reaction mixture composition expressed in terms of the molar ratios as follows:

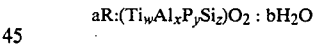
$$aR:(Ti_wAl_xP_ySi_z)O_2 : bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "w", "x", "y" and "z" represent the mole fractions of titanium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that $(w+x+y+z)=1.00$ mole. Molecular sieves containing titanium, aluminum, phosphorus and silicon as framework tetrahedral oxides are prepared as follows:

Preparative Reagents

TiAPSO compositions are typically prepared numerous regents. Typical reagents which may be employed and abbreviations employed in U.S. Ser. No. 600,179 for such reagents are as follows:
(a) Alipro: aluminum isopropoxide;
(b) LUDOX LS: LUDOX-LS is the trade name of DuPont for an aqueous solution of 30 weight percent $SiO_2$ and 0.1 weight percent $Na_2O$;
(c) $H_3PO_4$: 85 weight percent aqueous phosphoric acid;
(d) Tiipro: titanium isopropoxide;
(e) TEAOH: 40 weight percent aqueous solution of tetraethylammonium hydroxide;
(f) $Pr_2NH$: di-n-propylamine, $(C_3H_7)_2NH$;
(g) $Pr_3NH$: tri-n-propylamine, $(C_3H_7)_3N$;
(h) Quin: Quinuclidine, $(C_7H_{13}N)$;
(i) MQuin: Methyl Quinuclidine hydroxide, $(C_7H_{13}NCH_3OH)$; and
(j) C-hex: cyclohexylamine.

Preparative Procedures

TiAPSOs may be prepared by forming a starting reaction mixture by adding the $H_3PO_4$ and the water. This mixture is mixed and to this mixture aluminum isopropoxide is added. This mixture is then blended until a homogeneous mixture is observed. To this mixture the LUDOX-LS is added and the resulting mixture blended (about 2 minutes) until a homogeneous mixture is observed.

The titanium isopropoxide is added to the above mixture and the resulting mixture blended until a homogeneous mixture is observed. The organic templating agent is then added to the resulting mixture and the resulting mixture blended until a homogeneous mixture is observed, i.e., about 2 to 4 minutes. When the organic templating agent is quinuclidine the procedure is modified such that the quinuclidine is dissolved in about one half the water and accordingly the $H_3PO_4$ is mixed with about one half the water. (The pH of the mixture is measured and adjusted for temperature). The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out at the autogenous pressure.

The products are removed from the reaction vessel and cooled.

MgAPSO MOLECULAR SIEVES

The MgAPSO molecular sieves of U.S. Ser. No. 600,180, filed Apr. 13, 1984 have three-dimensional microporous framework structures of $MgO_2^{-2}$, $AlO_2^{-}$, $PO_2^{+}$ and $SiO_2$ tetrahedral oxide units and have an empirical chemical composition on an anhydrous basis expressed by the formula:

wherein "R" represents at least one organic templating agent present in the intracrystalline pore system; "m" represents the molar amount of "R" present per mole of $(Mg_wAl_xP_ySi_z)O_2$ and has a value from zero (0) to about 0.3; and "w", "x", "y" and "z" represent the mole fractions of magnesium, aluminum, phosphorus and silicon, respectively, present as tetrahedral oxides and each preferably has a value of at least 0.01. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.39 | 0.59 | 0.02 |
| C | 0.01 | 0.60 | 0.39 |
| D | 0.01 | 0.01 | 0.98 |
| E | 0.60 | 0.01 | 0.39 |

In a preferred subclass of the MgAPSO molecular sieves the values "w", "x", "y" and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

MgAPSO compositions are generally synthesized by hydrothermal crystallization for an effective time at effective pressures and temperatures from a reaction mixture containing reactive sources of magnesium, silicon, aluminum and phosphorus, an organic templating, i.e., structure-directing, agent, preferably a compound of an element of Group VA of the Periodic Table, and may be an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the MgAPSO product are obtained, usually a period of from several hours to several weeks. Generally, the crystallization period will be from about 2 hours to about 30 days with it typically being from about 4 hours to about 20 days for obtaining MgAPSO crystals. The product is recovered by any convenient method such as centrifugation or filtration.

In synthesizing the MgAPSO compositions, it is preferred to employ reaction mixture compositions expressed in terms of the molar ratios as follows:

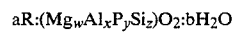

wherein "R" is an organic templating agent; "a" is the amount of organic templating agent "R" and can have a value within the range of from zero (0) to about 6 and is more preferably an effective amount greater than zero to about 6; "b" has a value of from zero (0) to about 500, preferably between about 2 and about 300; and "w", "x", "y" and "z" represent the mole fractions of magnesium, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that $(w+x+y+z)=1.00$ mole. Molecular sieves containing magnesium, aluminum, phosphorus and silicon as framework tetrahedral oxides are prepared as follows:

Preparative Reagents

MgAPSO compositions are prepared using numerous reagents. Typical reagents which may be employed to prepare MgAPSOs include:
(a) Alipro: aluminum isopropoxide;
(b) CATAPAL: Trademark of Condea for hydrated pseudoboehmite;
(c) LUDOX-LS: Trademark of DuPont for an aqueous solution of 30 weight percent $SiO_2$ and 0.1 weight percent $Na_2O$;
(d) $Mg(Ac)_2$ : magnesium acetate tetrahydrate, $Mg(C_2H_3O_2)_2 \cdot 4H_2O$;
(e) $H_3PO_4$: 85 weight percent aqueous phosphoric acid in water;
(f) TBAOH: tetraethylammonium hydroxide (40 wt. % in water);
(g) $Pr_2NH$: di-n-propylamine;
(h) $Pr_3NH$: tri-n-propylamine;
(i) Quin: Quinuclidine;
(j) MQuin: Methyl Quinuclidine hydroxide, (17.9% in water);
(k) C-hex: cyclohexylamine;
(l) TEAOH: tetraethylammonium hydroxide (40 wt. % in water);
(m) DEEA: Diethylethanolamine;
(n) i-$Pr_2NH$: di-isopropylamine;
(o) TEABr: tetraethylammonium bromide; and
(p) TPAOH: tetrapropylammonium hydroxide (40 wt. % in water).

Preparative Procedures

The MgAPSO compositions may be prepared by preparing reaction mixtures having a molar composition expressed as:

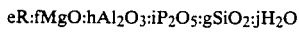
$eR:fMgO:hAl_2O_3:iP_2O_5:gSiO_2:jH_2O$ wherein e, f, g, h, i and j represent the moles of template R, magnesium (expressed as the oxide), $SiO_2$, $Al_2O_3$, $PO_2O_5$ ($H_3PO_4$ expressed as $P_2O_5$) and $H_2O$, respectively.

The reaction mixtures may be prepared by the following representative procedures, designated hereinafter as Methods A, B and C.

Method A

The reaction mixture is prepared by mixing the ground aluminum source (Alipro or CATAPAL) with the $H_3PO_4$ and water on a gradual basis with occasional cooling with an ice bath. The resulting mixture is blended until a homogeneous mixture is observed. When the aluminum source is CATAPAL the water and $H_3PO_4$ is first mixed with the CATAPAL added thereto. The magnesium acetate is dissolved in portion of the water and is then added followed by addition of the LUDOX-LS. The combined mixture is blended until a homogenous mixture is observed. The organic templating agent is added to this mixture and blended until a homogenous mixture is observed. The resulting mixture (final reaction mixture) is placed in a lined (polytetrafluoroethylene) stainless steel pressure vessel and digested at a temperature (150° C. or 200° C.) for an effective time. Alternatively, if the digestion temperature is 100° C. the final reaction mixture is placed in a lined (polytetrafluoroethylene) screw top bottle for a time. Digestions are typically carried out at the autogenous pressure. The products are removed from the reaction vessel, cooled and evaluated as set forth hereinafter.

Method B

When method B is employed the organic templating agent is di-n-propylamine. The aluminum source, silicon source and one-half of the water are first mixed and blended until a homogenous mixture is observed. A second solution was prepared by mixing the remaining water, the $H_3PO_4$ and the magnesium acetate. This solution is then added to the above mixture. The magnesium acetate and $H_3PO_4$ solution is then added to the above mixture and blended until a homogenous mixture is observed. The organic templating agent(s) is then added and the resulting reaction mixture digested and product recovered as is done in Method A.

Method C

Method C is carried out by mixing aluminum isopropoxide, LUDOX-LS and water in a blender or by mixing water and aluminum isopropoxide in a blender followed by addition of the LUDOX-LS. $H_3PO_4$ and magnesium acetate are then added to this mixture. The organic templating agent is then added to the resulting mixture and digested and product recovered as is done in Method A.

MnAPSO MOLECULAR SIEVES

The MnAPSO molecular sieves of U.S. Ser. No. 600,175, filed Apr. 13, 1984 have a framework structure of $MnO_2^{-2}$, $AlO_2^{-}$, $PO_2^{+}$, and $SiO_2$ tetrahedral units having an empirical chemical composition on an anhydrous basis expressed by the formula:

$mR:(Mn_wAl_xP_ySi_z)O_2$ wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of element manganese, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |

-continued

| Point | Mole Fraction | | |
|---|---|---|---|
| | x | y | (z + w) |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w, x, y and z may be as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

MnAPSO compositions are generally synthesized by hydrothermal crystallization from a reaction mixture containing reactive sources of manganese, silicon, aluminum and phosphorus, preferably an organic templating, i.e., structure-directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between about 50° C. and about 250° C., and preferably between about 100° C. and about 200° C. until crystals of the MnAPSO product are obtained, usually a period of from several hours to several weeks. Typical effective times of from 2 hours to about 30 days with generally from about 4 hours to about 20 days have been observed. The product is recovered by any convenient method such as centrifugation or filtration.

In synthesizing the MnAPSO compositions, it is preferred to employ a reaction mixture composition expressed in terms of the molar ratios as follows:

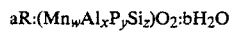
$$aR:(Mn_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "w", "x", "y" and "z" represent the mole fractions of manganese, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that $(w+x+y+z)=1.00$ mole. Molecular sieves containing manganese, aluminum, phosphorus and silicon as framework tetrahedral oxide units are prepared as follows:

Preparative Reagents

MnAPSO compositions may be prepared by numerous reagents. Reagents which may be employed to prepare MnAPSOs include:

(a) Alipro: aluminum isopropoxide;
(b) CATAPAL: Trademark of Condea Corporation for hydrated pseudoboehmite;
(c) LUDOX-LS: LUDOX-LS is the trade name of DuPont for an aqueous solution of 30 weight percent $SiO_2$ and 0.1 weight percent $Na_2O$;
(d) $H_3PO_4$: 85 weight percent aqueous phosphoric acid;
(e) MnAc: Manganese acetate, $mn(C_2H_3O_2)_2.4H_2O$;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: tri-n-propylamine $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2-diethylaminoethanol.

Preparative Procedures

MnAPSOs are prepared by forming a starting reaction mixture by adding the $H_3PO_4$ to one half of the quantity of water. This mixture is mixed and to this mixture the aluminum isopropoxide or CATAPAL is added. This mixture is then blended until a homogeneous mixture is observed. To this mixture the LUDOX-LS is added and the resulting mixture blended (about 2 minutes) until a homogeneous mixture is observed. A second mixture is prepared using the manganese acetate and the remainder (about 50%) of the water. The two mixtures are admixed and the resulting mixture blended until a homogenous mixture is observed. The organic templating agent is then added to the resulting mixture and the resulting mixture blended until a homogeneous mixture is observed, i.e., about 2 to 4 minutes. (The pH of the mixture is measured and adjusted for temperature). The mixture is then placed in a lined (polytetrafluoroethylene) stainless steel pressure vessel and digested at a temperature (150° C. or 200° C.) for a time or placed in lined screw top bottles for digestion at 100° C. Digestions are typically carried out at the autogenous pressure.

CoAPSO MOLECULAR SIEVES

The CoAPSO molecular sieves of U.S. Ser. No. 600,174, filed Apr. 13, 1984 have three-dimensional microporous framework structures of $CoO_2^{-2}$, $AlO_2^{-}$, $PO_2^{+}$ and $SiO_2$ tetrahedral units and have an empirical chemical composition on an anhydrous basis expressed by the formula:

$$mR:(Co_wAl_xP_ySi_z)O_2$$

wherein "R" represents at least one organic templating agent present in the intracrystalline pore system; "m" represents the molar amount of "R" present per mole of $(Co_wAl_xP_ySi_z)O_2$ and has a value of from zero to about 0.3; and "w", "x", "y" and "z" represent the mole fractions of cobalt, aluminum, phosphorus and silicon, respectively, present as tetrahedral oxides, where the mole fractions "w", "x", "y" and "z" are each at least 0.01 and are generally defined, as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the CoAPSO molecular sieves the values of "w", "x", "y", and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

CoAPSO compositions are generally synthesized by hydrothermal crystallization from a reaction mixture containing reactive sources of cobalt, silicon, aluminum and phosphorus, an organic templating, i.e., structure-directing, agent, preferably a compound of an element of Group VA of the Periodic Table, and optionally an alkali metal. The reaction mixture is generally placed in a sealed pressure vessel, preferably lined with an inert plastic material such as polytetrafluoroethylene and heated, preferably under autogenous pressure at an effective temperature which is generally between 50° C. and 250° C. and preferably between 100° C. and 200° C. until crystals of the CoAPSO product are obtained, usually for an effective time of from several hours to several weeks. Generally the effective crystallization time will be from about 2 hours to about 30 days and typically from about 4 hours to about 20 days. The product is recovered by any convenient method such as centrifugation or filtration.

In synthesizing the CoAPSO, it is preferred to employ a reaction mixture composition expressed in terms of the molar ratios as follows:

$aR:(Co_wAl_xP_ySi_z)O_2:bH_2O$ wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and 300; and "w", "x", "y" and "z" represent the mole fractions of cobalt, aluminum, phosphorus and silicon, respectively, and each has a value of at least 0.01. In a preferred embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that $(w+x+y+z)=1.00$ mole. Molecular sieves containing cobalt, aluminum, phosphorus and silicon as framework tetrahedral oxide units are prepared as follows:

Preparative Reagents

CoAPSO compositions may be prepared using numerous reagents. Reagents which may be employed to prepared CoAPSOs include:
(a) Alipro: aluminum isoproproxide;
(b) CATAPAL: Trademark of Condea Corporation for pseudoboehmite;
(c) LUDOX-LS: Trademark of DuPont for an aqueous solution of 30 weight percent $SiO_2$ and 0.1 weight percent $Na_2O$;
(d) $Co(Ac)_2$: cobalt acetate $Co(C_2H_3O_2)_2.4H_2O$;
(e) $CoSO_4$: cobalt sulfate $(CoSO_4.7H_2O)$;
(f) $H_3PO_4$: 85 weight percent phosphoric acid in water;
(g) TBAOH: tetrabutylammonium hydroxide (25 wt % in methanol);
(h) $Pr_2NH$: di-n-propylamine, $(C_3H_7)_2NH$;
(i) $Pr_3N$: tri-n-propylamine, $(C_3H_7)_3N$;
(j) Quin: Quinuclidine $(C_7H_{13}N)$;
(k) MQuin: Methyl Quinuclidine hydroxide, $(C_7H_{13}NCH_3OH)$;
(l) C-hex: cyclohexylamine;
(m) TEAOH: tetraethylammonium hydroxide (40 wt. % in water);
(n) DEEA: diethanolamine;
(o) TPAOH: tetrapropylammonium hydroxide (40 wt. % in water); and
(p) TMAOH: tetramethylammonium hydroxide (40 wt. % in water).

Preparative Procedure

CoAPSO compositions may be prepared by preparing reaction mixtures having a molar composition expressed as:

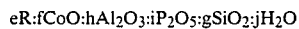

wherein e, f, h, i, g and j represent the moles of template R, cobalt (expressed as the oxide), $Al_2O_3$, $P_2O_5$ ($H_3PO_4$ expressed as $P_2O_5$), $SiO_2$ and $H_2O$, respectively.

The reaction mixtures are prepared by forming a starting reaction mixture comprising the $H_3PO_4$ and one-half of the water. This mixture is stirred and the aluminum source (Alipro or CATAPAL) added. The resulting mixture is blended until a homogeneous mixture is observed. The LUDOX-LS is then added to the resulting mixture and the new mixture blended until a homogeneous mixture is observed. The cobalt source (e.g., $Co(Ac)_2$, $Co(SO_4)$ or mixtures thereof) is dissolved in the remaining water and combined with the first mixture. The combined mixture is blended until a homogeneous mixture is observed. The organic templating agent is added to this mixture and blended for about two to four minutes until a homogeneous mixture is observed. The resulting mixture (final reaction mixture) is placed in a lined (polytetrafluoroethylene) stainless steel pressure vessel and digested at a temperature (150° C., 200° C. or 225° C.) for a time. Digestions are typically carried out at the autogenous pressure. The products are removed from the reaction vessel and cooled.

ZnAPSO MOLECULAR SIEVES

The ZnAPSO molecular sieves of U.S. Ser. No. 600,170, filed Apr. 13, 1984 comprise framework structures of $ZnO_2^{-2}$, $AlO_2^-$, $PO_2^+$ and $SiO_2$ tetrahedral units having an empirical chemical composition on an anhydrous basis expressed by the formula:

$$mR:(Zn_wAl_xP_ySi_z)O_2$$

wherein "R" represents at least one organic templating agent present in the intracrystalline pore system; "m" represents the molar amount of "R" present per mole of $(Zn_wAl_xP_ySi_z)O_2$ and has a value of zero to about 0.3; and "w", "x", "y" and "z" represent the mole fractions of zinc, aluminum, phosphorus and silicon, respectively, present as tetrahedral oxides and each has a value of at least 0.01. The mole fractions "w", "x", "y" and "z" are generally defined being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of ZnAPSO molecular sieves the values "w", "x", "y" and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

ZnAPSO compositions are generally synthesized by hydrothermal crystallization at effective process conditions from a reaction mixture containing active sources of zinc, silicon, aluminum and phosphorus, preferably an organic templating, i.e., structure-directing, agent, preferably a compound of an element or Group VA of the Periodic Table, and/or optionally an alkali of other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the ZnAPSO product are obtained, usually a period of from several hours to several weeks. Generally the effective crystallization period is from about 2 hours to about 30 days with typical periods of from about 4 hours to about 20 days being employed to obtain ZnAPSO products.

The product is recovered by any convenient method such as centrifugation or filtration.

In synthesizing the ZnAPSO compositions, it is preferred to employ a reaction mixture composition expressed in terms of the molar ratios as follows:

$$aR:(Zn_wAl_xP_ySi_z)O_2:bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, more preferably between about 2 and about 300; and "w", "x", "y" and "z" represent the mole fractions of zinc, aluminum, phosphorus and silicon, respectively, and each has a value of at least 0.01. In a preferred embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "w", "x", "y" and "z" such that $(w+x+y+z)=1.00$ mole. Molecular sieves containing zinc, aluminum, phosphorus and silicon as framework tetrahedral oxide units are prepared as follows:

Preparative Reagents

ZnAPSO compositions are typically prepared using numerous reagents. Reagents which may be employed to prepare ZnAPSOs include:

(a) Alipro: aluminum isopropoxide;
(b) LUDOX-LS: LUDOX-LS is the trade name of DuPont for an aqueous solution of 30 weight percent $SiO_2$ and 0.1 weight percent $Na_2O$;
(c) CATAPAL: Trademark of Condea Corporation for hydrated pseudoboehmite;
(d) $H_3PO_4$: 85 weight percent aqueous phosphoric acid;
(e) ZnAc: Zinc Acetate, $Zn(C_2H_3O_2)_2.4H_2O$;
(f) TEAOH: 40 weight percent aqueous solution of tetraethylammonium hydroxide;
(g) TBAOH: 40 weight percent aqueous solution of tetrabutylammonium hydroxide;
(h) TMAOH: Tetramethylammonium hydroxide pentahydrate, $(CH_3)_4NOH.5H_2O$;
(i) TPAOH: 40 weight percent aqueous solution of tetrapropylammonium hydroxide, $(C_3H_7)_4NOH$;
(j) $Pr_2NH$: di-n-propylamine, $(C_3H_7)_2NH$;
(k) $Pr_3N$: Tri-n-propylamine, $(C_3H_7)_3N$;
(l) Quin: Quinuclidine, $(C_7H_{13}N)$;
(m) C-hex: cyclohexylamine; and
(n) DEEA: diethylethanolamine, $(C_2H_5)_2NC_2H_5OH$.

Preparative Procedure

ZnAPSO compositions are typically prepared by forming reaction mixtures having a molar composition expressed as:

$$eR:fZnO:gAl_2O_3:hP_2O_5:iSiO_2:jH_2O$$

wherein e, f, g, h, i and j represent the moles of template R, zinc (expressed as the oxide), $Al_2O_3$, $P_2O_5$ ($H_3PO_4$ expressed as $P_2O_5$), $SiO_2$ and $H_2O$, respectively.

The reaction mixtures are generally prepared by forming a starting reaction mixture comprising the $H_3PO_4$ and a portion of the water. This mixture is stirred and the aluminum source added. The resulting mixture is blended until a homogeneous mixture is observed. The LUDOX-LS is then added to the resulting mixture and the new mixture blended until a homogeneous mixture is observed. The zinc source (zinc acetate) is dissolved in the remaining water and combined with the first mixture. The combined mixture is blended until a homogenous mixture is observed. The organic templating agent is added to this mixture and blended for about two to four minutes until a homogenous mixture is observed. The resulting mixture (final reaction mixture) is placed in a lined (polytetrafluoroethylene) stainless steel pressure vessel and digested at an effective temperature for an effective time. Digestions are typically carried out at the autogenous pressure. The products are removed from the reaction vessel and cooled.

FeAPSO MOLECULAR SIEVES

The FeAPSO of U.S. Ser. No. 600,173, filed Apr. 13, 1984 have molecular sieves having a three dimensional microporous crystal framework structures of $FeO_2^{-2}$, (and/or $FeO_2^-$), $AlO_2^-$, $PO^+_2$ and $SiO_2$ Tetrahedral oxide units and having a unit empirical formula, on an anhydrous basis, of:

$$mR:(Fe_wAl_xP_ySi_z)O_2 \quad (1)$$

wherein "R" represents at least one organic templating agent present in the intracrystalline pore system; "m" represents the moles of "R" present per mole of $(Fe_wAl_xP_ySi_z)O_2$ and has a value of from zero (0) to about 0.3; the maximum value of "m" in each case depends upon the molecular dimensions of the templating agent and the available void volume of the pore system of the particular molecular sieve involved; and "w", "x", "y" and "z" represent the mole fractions of iron, aluminum, phosphorus and silicon, respectively, present as tetrahedral oxides, said mole fractions being such that they are within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w, x, y and z may be as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The FeAPSOS of the instant invention are generally synthesized by hydrothermal crystallization from a reaction mixture comprising reactive sources of iron, aluminum, phosphorus and silicon, and preferably one or more organic templating agents. Optionally, alkali or other metal(s) may be present in the reaction mixture and may act as templating agents. The reaction mixture is generally placed in a pressure vessel, preferably lined with an inert plastic material, such as polytetrafluoroethylene, and heated, preferably under the autogenous pressure, at an effective temperature which is generally between about 50° C., and about 250° C. and preferably between about 100° C. and 200° C. until crystals of the FeAPSO product are obtained, usually a period of from several hours to several weeks. Molecular sieves containing iron, aluminum phosphorus and silicon as framework tetrahedral oxide units are typically prepared as follows:

Preparative Reagents

FeAPSO compositions may be prepared using numerous reagents. Reagents which may employed to prepare FeAPSOs include:
(a) Alipro: aluminum isopropoxide, $Al(OCH(CH_3)_2)_3$;
(b) LUDOX-LS: LUDOX-LS is the trademark of Du Pont for an agueous solution of 30 weight percent $SiO_2$ and 0.1 weight percent $Na_2O$;
(c) CATAPAL: trademark for hydrated aluminum oxide containing about 75 wt. percent $Al_2O_3$ (pseudoboehmite phase) and about 25 wt. percent water;
(d) $Fe(Ac)_2$ : Iron (II) acetate;
(e) $FeSO_4$ : Iron (II) sulfate hexahydrate;
(f) $H_3PO_4$: 85 weight percent phosphoric acid in water;
(g) TEAOH: 40 weight percent aqueous solution of tetraethylammonium hydroxide;
(h) TBAOH: 40 weight percent aqueous solution of tetrabutylammonium hydroxide;
(i) $Pr_2NH$: di-n-propylamine $((C_3H_7)_{d2}NH)$;
(j) $Pr_3N$: tri-n propylamine $((C_3H_7)_3N)$;
(k) Quin: Quinuclidine $(C_7H_{13}N)$;
(l) MQuin: Methyl Quinuclidine hydroxide $(C_7H_{13}NCH_3OH)$;
(m) TMAOH: tetramethylammonium hydroxide pentahydrate; and
(o) C-hex: cyclohexylamine.

(a) Reaction mixtures to prepare FeAPSOs are typically prepared by grinding an aluminum isopropoxide in a blender followed by slowly adding a $H_3PO_4$ solution with mixing. A solution/dispersion of iron acetate in water is added and then a silica (e.g., LUDOX-LS) is added. The organic templating agent is then added to this mixture, or in some cases one-half of this mixture, and the mixture blended to form a homogeneous mixture. For example, in one embodiment, the number of moles of each component in the reaction mixture is as follows:

| Component | Moles |
|---|---|
| Al₂O₃ | 0.9 |
| P₂O₅ | 0.9 |
| SiO₂ | 0.2** |
| FeO* | 0.2 |
| TEAOH | 1.0 |
| H₂O | 50 |

*Iron (II) acetate reported as Iron (II) oxide.
**SiO₂ was 0.6 in examples 5C to 8C The reaction mixture is sealed in a stainless steel pressure vessel lined with polytetrafluoroethylene and heated in an oven at a temperature, time and at the autogenous pressure. The solid reaction product is recovered by filtration, washed with water and dried at room temperature.

In another embodiment, reaction mixtures are prepared by grinding the aluminum isopropoxide in a blender followed by addition of a solution/dispersion of iron (II) acetate. H₃PO₄ is added to this mixture and the resulting mixture blended to form a homogeneous mixture. A silica (e.g., LUDOX-LS) is added to this mixture except that in some instances the silica may be added with the H₃PO₄. The resulting mixtures were blended until a homogeneous mixture is observed. Organic templating agent is added to each mixture and the resulting mixtures placed in a stainless steel pressure vessel lined with polytetrafluoroethylene and heated, washed and the product recovered. In this embodiment the number of moles of each component in the reaction mixture is as follows:

| Component | Moles |
|---|---|
| Al₂O₃ | 0.9 |
| P₂O₅ | 0.9 |
| SiO₂ | 0.2 |
| FeO* | 0.2 |
| Template | 1.0 |
| H₂O | 50 |

*Iron (II) acetate reported as Iron (II) oxide.

CoMnAPSO MOLECULAR SIEVES

CoMnAPSO molecular sieves may be expressed by the empirical chemical formula (anhydrous) as follows:

$$mR:(Co_uMn_vAl_xP_ySi_z)O_2$$

where "u", "v", "x", "y" and "z" represent the mole. The CoMnAPSO molecular sieves have an empirical chemical composition on an anhydrous basis expressed by the formula:

$$mR : (Co_uMn_vAl_xP_ySi_z)O_2$$

wherein "R" represents at least one organic templating agent present in the intracrystalline pore system; "m" represents the molar amount of "R" present per mole of $(Co_uMn_vAl_xP_ySi_z)O_2$ from zero (0) to about 0.3; and "u", "v", "x", "y" and "z" represent the mole fractions of cobalt, manganese, aluminum, phosphorus and silicon, respectively, present as tetrahedral oxides. The mole fractions "u", "v", "x", "y", and "z" are generally defined as being within the limiting compositional values or points as follows, wherein "w", the combined mole fractions of manganese and cobalt, is the sum of "u" and "v":

| Point | Mole Fraction | | |
|---|---|---|---|
| | x | y | (z + w) |
| A | 0.60 | 0.37 | 0.03 |
| B | 0.37 | 0.60 | 0.03 |
| C | 0.01 | 0.60 | 0.39 |
| D | 0.01 | 0.01 | 0.98 |
| E | 0.60 | 0.01 | 0.39 |

Preferably the mole fractions u, v, x, y and z will fall within the limiting compositional values or points as follows:

| Point | Mole Fraction | | |
|---|---|---|---|
| | x | y | (z + w) |
| a | 0.55 | 0.42 | 0.03 |
| b | 0.42 | 0.55 | 0.03 |
| c | 0.10 | 0.55 | 0.35 |
| d | 0.55 | 0.10 | 0.35 |

CoMnAPSO compositions are generally synthesized by hydrothermal crystallization from a reaction mixture containing reactive sources of cobalt, manganese, aluminum, phosphorus and silicon and preferably an organic templating agent, i.e., structure-directing, agent. The structure-directing agents are preferably a compound of an element of Group VA of the Periodic Table, and may be an alkali or other metal. The reaction mixture is generally placed in a sealed pressure vessel, preferably lined with an inert plastic material such as polytetrafluoroethylene and heated, preferably under autogenous pressure and at typical effective temperatures between 50° C. and 250° C., preferably between 100° C. and 200° C., until crystals of the CoMnAPSO product are obtained, usually over a period of from several hours to several weeks. Typical effective crystallization times are from about 2 hours to 30 days with from about 4 hours to about 20 days being generally employed to obtain CoMnAPSO products. The product is recovered by any convenient method such as centrifugation or filtration.

In synthesizing the CoMnAPSO compositions, it is preferred to employ a reaction mixture composition expressed in terms of the molar ratios as follows:

$$aR : (Co_uMn_vAl_xP_ySi_z)O_2: bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "u", "v", "x", "y", and "z" represent the mole fractions of elements cobalt, manganese, aluminum, phosphorus and silicon, respectively, and each has a value of at least 0.01.

In one embodiment the reaction mixture is selected such that the mole fractions "w", "x", "y" and "z" are generally defined as being within the limiting compositional values or points as follows:

| Point | Mole Fraction | | |
|---|---|---|---|
| | x | y | (z + w) |
| F | 0.60 | 0.37 | 0.03 |
| G | 0.37 | 0.60 | 0.03 |

| Point | Mole Fraction | | |
|---|---|---|---|
| | x | y | (z + w) |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "u", "v", "x", "y" and "z" such that $(u+v+x+y+z) = 1.00$ mole. CoMnAPSO compositions were prepared using numerous regents.

Reagents which may be employed to prepare CoMnAPSOs include:
(a) Alipro: aluminum isopropoxide;
(b) LUDOX-LS: LUDOX-LS is the trade name of DuPont for an agueous solution of 30 weight percent $SiO_2$ and 0.1 weight percent $Na_2O$;
(c) $H_3PO_4$: 85 weight percent phosphoric acid;
(d) MnAc: Manganese acetate, $Mn(C_2H_3O_2)_2.4H_2O$;
(e) CoAc: Cobalt Acetate, $Co(C_2H_3O_2)_2.4H_2O$;
(f) TEAOH: 40 weight percent aqueous solution of tetraethylammonium hydroxide; and
(g) $Pr_2NH$: di-n-propylamine, $(C_3H_7)_2NH$.

Preparative Procedures

CoMnAPSOs may be prepared by forming a starting reaction mixture by adding $H_3PO_4$ and one-half of the quantity of water. To this mixture an aluminum isopropoxide is added. This mixture is then blended until a homogeneous mixture is observed. To this mixture a silica (e.g., LUDOX-LS) is added and the resulting mixture blended (about 2 minutes) until a homogeneous mixture is observed. A second mixture is prepared using manganese acetate and one-half of the remaining water. A third mixture is prepared using cobalt acetate and one-half of the remaining water. The three mixtures are admixed and the resulting mixture blended until a homogeneous mixture is observed. The organic templating agent is then added to the resulting mixture and the resulting mixture blended until a homogeneous mixture is observed, i.e., about 2 to 4 minutes. The pH of the mixture is measured and adjusted for temperature. The mixture is then placed in a lined (polytetrafluoroethylene) stainless steel pressure vessel and digested at a temperature. Digestions are typically carried out at the autogenous pressure.

CoMnMgAPSO MOLECULAR SIEVES

The CoMnMgAPSO molecular sieves of U.S. Ser. No. 600,182, filed Apr. 13, 1984 have three-dimensional microporous framework structures of $CoO_2^{-2}$, $MnO_2^{-2}$, $MgO_2^{-2}$, $AlO_2^-$, $PO_2^+$ and $SiO_2$ tetrahedral oxide units and have an empirical chemical composition on an anhydrous basis expressed by the formula:

wherein "R" represents at least one organic templating agent present in the intracrystalline pore system; "m" represents the molar amount of "R" present per mole of $(Co_tMn_uMg_vAl_xP_ySi_z)O_2$, and has a value of from zero to about 0.3; and "t", "u", "v", "x", "y" and "z" represent the mole fractions of cobalt, manganese, magnesium, aluminum, phosphorus and silicon, respectively, present as tetrahedral oxides, each having a value of at least 0.01. The mole fractions "t", "u", "v", "x", "y" and "z" are generally defined as being within the limiting compositional values or points as follows, wherein "w", the combined mole fractions of cobalt, manganese and magnesium, is the sum of "t", "u" and "v":

| Point | Mole Fraction | | |
|---|---|---|---|
| | x | y | (z + w) |
| A | 0.60 | 0.36 | 0.04 |
| B | 0.36 | 0.60 | 0.04 |
| C | 0.01 | 0.60 | 0.39 |
| D | 0.01 | 0.01 | 0.98 |
| E | 0.60 | 0.01 | 0.39 |

In a preferred subclass of the CoMnMgAPSO molecular sieves the values of "w", "x", "y" and "z" in the above formula are within the limiting compositional values or points as follows:

| Point | Mole Fraction | | |
|---|---|---|---|
| | x | y | (z + w) |
| a | 0.55 | 0.41 | 0.04 |
| b | 0.41 | 0.55 | 0.04 |
| c | 0.10 | 0.55 | 0.35 |
| d | 0.55 | 0.10 | 0.35 |

CoMnMgAPSO compositions are generally synthesized by hydrothermal crystallization from a reaction mixture containing reactive sources of cobalt, manganese, magnesium, aluminum, phosphorus and silicon, and preferably an organic templating agent, i.e., structure-directing, agent. The structure-directing agents are preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the CoMnMgAPSO product are obtained, usually over a period of from several hours to several weeks. Typical crystallization times are from about 2 hours to about 30 days with from about 4 hours to about 20 days generally being employed to obtain CoMnMgAPSO products. The product is recovered by any convenient method such as centrifugation or filtration.

In synthesizing the CoMnMgAPSO compositions, it is preferred to employ a reaction mixture composition expressed in terms of the molar ratios as follows:

wherein "R" is an organic templating agent; "a" is the amount of organic templating agent "R" and has a value of from zero to about 6 and is preferably an effective amount within the range of greater than zero (0) to about 6 and more preferably from greater than zero to about 2; "b" has a value of from zero (0) to about 500, preferably between about 2 and about 300; and "t", "u", "v", "x", "y", and "z" represent the mole fractions of cobalt, manganese, magnesium, aluminum, phosphorus and silicon, respectively, and each has a value of at least 0.01.

In a preferred embodiment the reaction mixture is selected such that the mole fractions "w", "x", "y" and "z", where "w" is the sum of "t"+"u"+"v", are generally defined as being within the limiting compositional values or points as follows:

| Point | Mole Fraction | | |
|---|---|---|---|
| | x | y | (z + w) |
| F | 0.60 | 0.36 | 0.04 |
| G | 0.36 | 0.60 | 0.04 |
| H | 0.01 | 0.60 | 0.39 |
| I | 0.01 | 0.01 | 0.98 |
| J | 0.60 | 0.01 | 0.39 |

In the foregoing expression of the reaction composition, the reactants are normalized with respect to the total of "t", "u", "v", "x", "y" and "z" such that $(t+u+v+x+y+z)=1.00$ mole. Molecular sieves containing cobalt, manganese, magnesium, aluminum, phosphorus and silicon as framework tetrahedral oxide units are prepared as follows:

Preparative Reagents

CoMnMgAPSO compositions may be prepared by using numerous reagents. Reagents which may be employed to prepare CoMnAPSOs include:
(a) Alipro: aluminum isopropoxide;
(b) LUDOX-LS: LUDOX-LS is the trade name of Du Pont for an agueous solution of 30 weight percent $SiO_2$ and 0.1 weight percent $Na_2O$;
(c) $H_3PO_4$: aqueous solution which is 85 weight percent phosphoric acid;
(d) MnAc: Manganese acetate, $Mn(C_2H_3O_2)_2.4H_2O$;
(e) CoAc: Cobalt Acetate, $Co(C_2H_3O_2)_2.4H_2O$;
(f) MgAc: Magnesium Acetate $Mg(C_2H_3O_2).4H_2O$;
(g) TEAOH: 40 weight percent aqueous solution of tetraethylammonium hydroxide; and
(h) $Pr_2NH$: di-n-propylamine, $(C_3H_7)_2NH$.

Preparative Procedures

CoMnMgAPSOs may be prepared by forming a starting reaction mixture by adding $H_3PO_4$ and one-half of the quantity of water. To this mixture an aluminum isopropoxide is added. This mixture is then blended until a homogeneous mixture is observed. To this mixture a silica (e.g., LUDOX-LS) is added and the resulting mixture blended (about 2 minutes) until a homogeneous mixture is observed.

Three additional mixtures are prepared using cobalt acetate, magnesium acetate and manganese acetate using one third of the remainder of the water for each mixture. The four mixtures are then admixed and the resulting mixture blended until a homogeneous mixture is observed. An organic templating agent is then added to the resulting mixture and the resulting mixture blended until a homogeneous mixture is observed, i.e., about 2 to 4 minutes. The mixture is then placed in a lined (polytetrafluoroethylene) stainless steel pressure vessel and digested at a temperature for a time. Digestions are typically carried out at the autogenous pressure.

MeAPO MOLECULAR SIEVES

MeAPO molecular sieves are crystalline microporous aluminophosphates in which the substituent metal is one of a mixture of two or more divalent metals of the group magnesium, manganese, zinc and cobalt and are disclosed in U.S. Pat. No. 4,567,029. Members of this novel class of compositions have a three-dimensional microporous crystal framework structure of $MO_2^{-2}$, $AlO_2^{-}$ and $PO_2^{+}$ tetrahedral units and have an essential empirical chemical composition, on an anhydrous basis, of:

$mR : (M_xAl_yP_z)O_2$ wherein "R" represents at least one organic templating agent present in the intracrystalline pore system; "m" represents the moles of "R" present per mole of $(M_xAl_yP_z)O_2$ and has a value of from zero to 0.3, maximum value in each case depending upon the molecular dimensions of the templating agent and the available void volume of the pore system of the particular metal aluminophosphate involved; "x", "y", and "z" represent the mole fractions of the metal "M", (i.e., magnesium, manganese, zinc and cobalt), aluminum and phosphorus, respectively, present as tetrahedral oxides, said mole fractions being such that they are representing the following values for "x", "y", and "z":

| Point | Mole Fraction | | |
|---|---|---|---|
| | x | y | z |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the metal aluminophosphates of this invention, the values of "x", "y" and "z" in the formula above are representing the following values for "x", "y" and "z":

| Point | Mole Fraction | | |
|---|---|---|---|
| | x | y | z |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The as synthesized compositions are capable of withstanding 350° C. calcination in air for extended periods, i.e., at least 2 hours, without becoming amorphous. While it is believed that the M, Al and P framework constituents are present in tetrahedral coordination with oxygen, it is theoretically possible that some minor fraction of these framework constituents are present in coordination with five or six oxygen atoms. It is not, moreover, necessarily the case that all of the M, Al and/or P content of any given synthesized product be a part of the framework in the aforesaid types of coordination with oxygen. Some of each constituent may be merely occluded or in some as yet undetermined form and may or may not be structurally significant.

Since the term "metal aluminophosphate" is somewhat cumbersome, particularly in view of the need for numerous repetitions thereof in describing such compositions, the "short hand" reference "MeAPO" is employed hereinafter. Also in those cases where the metal "Me" in the composition is magnesium, the acronym MAPO is applied to the composition. Similarly, ZAPO, MnAPO, and CoAPO are applied to the compositions which contain zinc, manganese and cobalt, respectively. To identify the various structural species which make up each of the subgeneric classes MAPO, ZAPO, CoAPO and MnAPO, each species is assigned a number and is identified, for example, as ZAPO-5, MAPO-11, CoAPO-11 and so forth.

The term "essential empirical chemical composition" is meant to include the crystal framework and can include any organic templating agent present in the pore system, but does not include alkali metal or other ions which can be present by virtue of being contained in the reaction mixture or as a result of post-synthesis ion exchange. Such ionic species, when present, function primarily as charge-balancing ions for $AlO_2^-$ and/or $MO_2^{-2}$ tetrahedra not associated with $PO_2^+$ tetrahedra or an organic ion derived from the organic templating agent.

The metal aluminophosphates ("MeAPOs") are synthesized by hydrothermal crystallization from a reaction mixture containing reactive sources of the metal "M", alumina and phosphate, an organic templating, i.e., structure directing, agent, preferably a compound of an element of Group VA of the Periodic Table, and optionally an alkali metal. The reaction mixture is placed in a sealed pressure vessel, preferably lined with an inert plastic material such as polytetrafluoroethylene and heated, preferably under autogenous pressure at a temperature between 100° C. and 225° C., and preferably between 100° C. and 200° C. until crystals of the metal aluminophosphate product are obtained, usually a period of from 4 hours to 2 weeks. The product is recovered by any convenient method such as centrifugation or filtration.

In synthesizing the MeAPO compositions, it is preferred to employ a reaction mixture composition expressed in terms of molar ratios as follows:

$$aR:(M_xAl_yP_z)O_2:bH_2O$$

wherein "R" is an organic templating agent; "a" has a value great enough to constitute an effective concentration of "R" and is within the range of >0 to 6; "b" has a value of from zero to 500, preferably 2 to 30; "M" represents a metal of the group zinc, magnesium, manganese and cobalt, "x", "y" and "z" represent the mole fractions, respectively, of "M", aluminum and phosphorus in the $(M_xAl_yP_z)O_2$ constituent, and each has a value o at least 0.01, the said points E, F, G, H, I, and J representing the following values for "x", "y" and "z":

| Point | Mole Fraction | | |
|---|---|---|---|
| | x | y | z |
| E | 0.01 | 0.70 | 0.29 |
| F | 0.01 | 0.29 | 0.70 |
| G | 0.29 | 0.01 | 0.70 |
| H | 0.40 | 0.01 | 0.59 |
| I | 0.40 | 0.59 | 0.01 |
| J | 0.29 | 0.70 | 0.01 |

In the foregoing expression of the reaction composition, the reactants are normalized with respect to a total of $(M+Al+P)=(x+y+z)=1.00$ mole.

In forming the reaction mixture from which the metal aluminophosphates are crystallized the organic templating agent can be any of those heretofore proposed for use in the synthesis of conventional zeolite aluminosilicates and microporous aluminophosphates. In general these compounds contain elements of Group VA of the Periodic Table of Elements, particularly nitrogen, phosphorus, arsenic and antimony, preferably N or P and most preferably N, which compounds also contain at least one alkyl or aryl group having from 1 to 8 carbon atoms. Particularly preferred nitrogen containing compounds for use as templating agents are the amines and quaternary ammonium compounds, the latter being represented generally by the formula $R_4N^+$ wherein each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. Both mono-, di- and triamines are advantageously utilized, either alone or in combination with a quaternary ammonium compound or other templating compound. Mixtures of two or more templating agents can either produce mixtures of the desired metal aluminophosphates or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; di-n-propylamine; tripropylamine; triethylamine; triethanolamine; piperidine; cyclohexylamine; 2-methylpyridine; N,N'-dimethylbenzylamine; N,N-dimethylethanolamine; choline; N,N'-dimethylpiperazine; 1,4-diazabicyclo (2,2,2) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; di-n-butylamine, neopentylamine; di-n-pentylamine; isopropylamine; t-butylamine; ethylenediamine; pyrrolidine; and 2-imidazolidone. Not every templating agent will direct the formation of every species of metal aluminophosphate (MeAPO), i.e., a single templating agent can, with proper manipulation of the reaction conditions, direct the formation of several MeAPO compositions, and a given MeAPO composition can be produced using several different templating agents.

The preferred phosphorus source is phosphoric acid, but organic phosphates such as triethylphosphate have been found satisfactory, and so also have crystalline or amorphous aluminophosphates such as the $AlPO_4$ composition of U.S. Pat. No. 4,310,440. Organo phosphorus compounds, such as tetrabutylphosphonium bromide do not, apparently serve as reactive sources of phosphorus, but these compounds do function as templating agents. Conventional phosphorus salts such as sodium metaphosphate, may be used, at least in part, as the phosphorus source, but are not preferred.

The aluminum source is preferably either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The metals zinc, cobalt, magnesium and manganese can be introduced into the reaction system in any form which permits the formation in situ of reactive divalent ions of the respective metals. Advantageously salts, oxides or hydroxides of the metals are employed such as cobalt chloride hexahydrate, alpha cobaltous iodide, cobaltous sulfate, cobalt acetate, cobaltous bromide, cobaltous chloride, zinc acetate, zinc bromide, zinc formate, zinc iodide, zinc sulfate heptahydrate, magnesium acetate, magnesium bromide, magnesium chloride, magnesium iodide, magnesium nitrate, magnesium sulfate, manganous acetate, manganous bromide, manganous sulfate, and the like.

While not essential to the synthesis of MeAPO compositions, it has been found that in general, stirring or other moderate agitation of the reaction mixture and/or seeding the reaction mixture with seed crystals of either the MeAPO species to be produced or a topologically similar aluminophosphate or aluminosilicate composition, facilitates the crystallization procedure.

After crystallization the MeAPO product is isolated and advantageously washed with water and dried in air. The as-synthesized MeAPO contains within its internal pore system at least one form of the templating agent employed in its formation. Most commonly the organic moiety is present, at least in part, as a charge balancing cation as is generally the case with as-synthesized aluminosilicate zeolites prepared from organic containing reaction systems. It is possible, however, that some or all of the organic moiety is an occluded molecular species in a particular MeAPO species. As a general rule, the templating agent, and hence the occluded organic species, is too larqe to move freely through the pore system of the MeAPO product and must be removed by calcining the MeAPO at temperatures of 200° C. to 700° C. to thermally degrade the organic species. In a few instances the pores of the MeAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein and in the claims does not include the condition of the MeAPO phase wherein the organic moiety occupying the intracrystalline pore system as a result of the hydrothermal crystallization process has been reduced by post synthesis treatment such that the value of "m" in the composition formula:

mR:(M$_x$Al$_y$P$_z$)O$_2$ has a value of less than 0.02. The other symbols of the formula are as defined hereinabove. In those preparations in which an aluminum alkoxide is employed as the source of aluminum, the corresponding alcohol is necessarily present in the reaction mixture since it is a hydrolysis product of the alkoxide. It has not been determined whether this alcohol participates in the syntheses process as a templating agent. For the purposes of this application, however, this alcohol is arbitrarily omitted from the class of templating agents, even if it is present in the as synthesized MeAPO material.

Since the MeAPO compositions are formed from AlO$_2$, PO$_2$, and MO$_2$ tetrahedral units which, respectively, have a net charge of $-1$, $+1$, and $-2$, the matter of cation exchangeability is considerably more complicated than in the case of zeolitic molecular sieves in which, ideally, there is a stoichiometric relationship between AlO$_2$ tetrahedra and charge balancing cations. In the MeAPO compositions, an AlO$_2^-$ tetrahedron can be balanced electrically either by association with a PO$_2^+$ tetrahedron or a simple cation such as an alkali metal cation, a cation of the metal "M" present in the reaction mixture, or an organic cation derived from the templating agent. Similarly an MO$_2^{-2}$ tetrahedron can be balanced electrically by association with PO$_2^+$ tetrahedra, a cation of the metal "M", organic cations derived from the templating agent, or other divalent or polyvalent metal cations introduced from an extraneous source. It has also been postulated that non adjacent AlO$_2^-$ and PO$_2^+$ tetrahedral pairs can be balanced by Na$^+$ and OH$^-$, respectively [Flanigen and Grose, Molecular Sieve Zeolites-I, ACS, Washington, D.C. (1971)].

FAPO MOLECULAR SIEVES

Ferroaluminophosphates are disclosed in U.S. Pat. No. 4,554,143, incorporated herein by reference, and have a three dimensional microporous crystal framework structure of AlO$_2$, FeO$_2$, and PO$_2$ tetrahedral units and have an essential empirical chemical composition, on an anhydrous basis, of:

mR:(Fe$_x$Al$_y$P$_z$)O$_2$ wherein "R" represents at least one organic templating agent present in the intracrystalline pore system; "m" represents the moles of "R" present per mole of (Fe$_x$Al$_y$P$_z$)O$_2$ and has a value of from zero to 0.3, t maximum value in each case depending upon the molecular dimensions of the templating agent and the available void volume of the pore system of the particular ferroaluminophosphate involved; "x", "y", and z"z" represent the mole fractions of iron, aluminum and phosphorus, respectively, present as tetrahedral oxides, representing the following values for "x", "y", and "z":

| Point | Mole Fraction | | |
|---|---|---|---|
| | x | y | z |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the ferroaluminophosphates the values of "x", "y" and "z" in the formula above are representing the following values for "x", "y" and "z":

| Point | Mole Fraction | | |
|---|---|---|---|
| | x | y | z |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The iron of the FeO$_2$ structural units can be in either the ferric or ferrous valence state, depending largely upon the source of the iron in the synthesis gel. Thus, an FeO$_2$ tetrahedron in the structure can have a net charge of either $-1$ or $-2$. While it is believed that the Fe, Al and P framework constituents are present in tetrahedral coordination with oxygen (and are referred to herein as such), it is theoretically possible that some minor fraction of these framework constituents are present in co-ordination with five or six oxyqen atoms. It is not, moreover, necessarily the case that all of the Fe, Al and/or P content of any given sy:thesized product is a part of the framework in the aforesaid types of coordination with oxygen. Some of each constituent may be merely occluded or in some as yet undetermined form, and may or may not be structurally siqnificant.

For convenience in describing the ferroaluminophosphates, the "short-hand" acronym "FAPO" is sometimes employed hereinafter. To identify the various structural species which make up the generic class FAPO, each species is assiqned a number and is identified, for example, as FAPO-11, FAPO-31 and so forth.

The term "essential empirical chemical composition" is meant to include the crystal framework and can include any organic templating agent present in the pore system, but does not include alkali metal or other ions which can be present by virtue of being contained in the reaction mixture or as a result of post synthesis ion exchange. Such ionic species, when present, function primarily as charge balancing ions for $FeO_2{}^-$ tetrahedra, and/or $AlO_2{}^{-2}$ tetrahedra, $FeO_2{}^{-2}$ tetrahedra associated with $PO_2{}^+$ tetrahedra or not associated with $PO_2{}^+$ tetrahedra or an organic ion derived from the organic templating agent.

The aforesaid ferroaluminophosphates are synthesized by hydrothermal crystallization from a reaction mixture containing reactive sources of iron oxide, alumina and phosphate, an organic templating, i.e., structure directing, agent, preferably a compound of an element of Group VA of the Periodic Table, and optionally an alkali metal. The reaction mixture is placed in a sealed pressure vessel, preferably lined with an inert plastic material such as polytetrafluoroethylene and heated, preferably under autogenous pressure at a temperature of at least 100° C., and preferably between 100° C. and 250° C. until crystals of the metal aluminophosphate product are obtained, usually a period of from 2 hours to 2 weeks. The product is recovered by any convenient method such as centrifugation or filtration.

In synthesizing the FAPO compositions, it is preferred to employ a reaction mixture composition expressed in terms of molar ratios as follows:

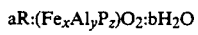

$$aR:(Fe_xAl_yP_z)O_2:bH_2O$$

wherein "R" is an organic templating agent; "a" has a value great enough to constitute an effective concentration of "R" and is within the range of $>0$ to 6; "b" has a value of from zero to 500, preferably 2 to 80; "x", "y" and "z" represent the mole fractions, respectively, of iron, aluminum and phosphorus in the $(Fe_xAl_yP_z)O_2$ constituent, and each has a value o least 0.01, and representing the following values for "x", "y" and "Z":

| Point | Mole Fraction | | |
|---|---|---|---|
| | x | y | z |
| E | 0.01 | 0.70 | 0.29 |
| F | 0.01 | 0.29 | 0.70 |
| G | 0.29 | 0.01 | 0.70 |
| H | 0.40 | 0.01 | 0.59 |
| I | 0.40 | 0.59 | 0.01 |
| J | 0.29 | 0.70 | 0.01 |

In the foregoing expression of the reaction composition, the reactants are normalized with respect to a total of $(Fe+Al+P)=(x+y+z)=1.00$ mole.

In forming the reaction mixture from which the ferroaluminophosphates are crystallized, the anic templating agent can be any of those heretofore proposed for use in the synthesis of conventional zeolite aluminosilicates and microporous aluminophosphates. In general these compounds contain elements of Group VA of the Periodic Table of Elements, particularly nitrogen, phosphorus, arsenic and antimony, preferably N or P and most preferably N, which compounds also contain at least one alkyl or aryl qroup having from 1 to 8 carbon atoms. Particularly preferred nitrogen-containing compounds for use as templating agents are the amines and quaternary ammonium compounds, the latter being represented generally by the formula $R_4N^+$ wherein each R is an alkyl or aryl qroup containing from 1 to 8 carbon atoms. Polymeric quaternary ammonium salts such as $[(C_{14}H_{32}N_2)(OH)_2]_x$ wherein "x" has a value of at least 2 are also suitably employed. Both mono-, di- and triamines are advantaqeously utilized, either alone or in combination with a quaternary ammonium compound or other templating compound. Mixtures of two or more templating agents can either produce mixtures of the desired metal aluminophosphates or the more strongly directing templating species may control the course of the reaction with the other templating species serving primarily to establish the pH conditions of the reaction gel. Representative templating agents include tetramethylammonium, tetraethylammoniun, tetrapropylammonium or tetrabutylammonium ions; di-n-propylamine; tri-n-propylamine; triethylamine; triethanolamine; piperidine; cyclohexylamine; 2-methylpyridine; N,N-dimethylbenzylamine; N,N-dimethylethanolamine; choline; N,N'-dimethylpiperazine; 1,4-diazabicyclo (2,2,2) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; di-n-butylamine, neopentylamine; di-n-pentylamine; isopropylamine; t-butylamine; ethylenediamine; pyrrolidine; and 2-imidazolidone. Not every templating agent will direct the formation of every species of ferroaluminophosphate (FAPO), i.e., a single templating agent can, with proper manipulation of the reaction conditions, direct the formation of several FAPO compositions, and a given FAPO composition can be produced using several different templating agents.

The phosphorus source is preferably phosphoric acid, but organic phosphates such as triethylphosphate have been found satisfactory, and so also have crystalline or amorphous aluminophosphates such as the $AlPO_4$ composition of U.S. Pat. No. 4,310,440. Organo phosphorus compounds, such as tetrabutylphosphonium bromide do not, apparently serve as reactive sources of phosphorus, but these compounds do function as templating agents. Conventional phosphorus salts such as sodium metaphosphate, may be used, at least in part, as the phosphorus source, but are not preferred.

The aluminum source is preferably either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

Iron can be introduced into the reaction system in any form which permits the formation in situ of reactive ferrous or ferric ions. Advantageously iron salts, oxides or hydroxides are employed such as iron sulfate, iron acetate, iron nitrate, or the like. Other sources such as a freshly precipitated iron oxide Y-FeOOH, are also suitable.

While not essential to the synthesis of FAPO compositions, it has been found that in qeneral, stirring or other moderate agitation of the reaction mixture and/or seeding the reaction mixture with seed crystals of either the FAPO species to be produced or a topologically similar aluminophosphate or aluminosilicate composition, facilitates the crystallization procedure.

After crystallization the FAPO product is isolated and advantageously washed with water and dried in air.

The as synthesized FAPO contains within its internal pore system at least one form of the templating agent employed in its formation. Most commonly the organic moiety is present, at least in part, as a charge balancing cation as is generally the case with as synthesized aluminosilicate zeolites prepared from organic containing reaction systems. It is possible, however, that some or all of the organic moiety is an occluded molecular species in a particular FAPO species. As a general rule, the templating agent, and hence the occluded organic species, is too large to move freely through the pore system of the FAPO product and must be removed by calcining the FAPO at temperatures of 200° C. to 700° C. to thermally degrade the organic species. In a few instances the pores of the FAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein and in the claims does not include the condition of the FAPO phase wherein th organic moiety occupying the intracrystalline pore system as a result of the hydrothermal crystallization process has been reduced by post synthesis treatment such that the value of "m" in the composition formula:

$mR:(Fe_xAl_yP_z)O_2$ has a value of less than 0.02. The other symbols of the formula are as defined hereinabove. In those preparations in which an aluminum alkoxide is employed as the source of aluminum, the corresponding alcohol is necessarily present in the reaction mixture since it is a hydrolysis product of the alkoxide. It has not been determined whether this alcohol participates in the syntheses process as a templating agent. For the purposes of this application, however, this alcohol is arbitrarily omitted from the class of templating agents, even if it is present in the as synthesized FAPO material.

Since the FAPO compositions are formed from $AlO_2^-$, $PO_2^+$, $FeO_2$ and/or $FeO_2^{-2}$ units the matter of cation exchangeability is considerably more complicated than in the case of zeolitic molecular sieves in which, ideally, there is a stoichiometric relationship between $AlO_2$ tetrahedra and charge balancing cations. In the FAPO compositions, an $AlO_2^-$ tetrahedron can be balanced electrically either by association with a $PO_2^+$ tetrahedron or a simple cation such as an alkali metal cation, a $Fe^{+2}$ or Fe $^{+3}$ cation present in the reaction mixture, or an organic cation derived from the templating agent. Similarly an $FeO_2^-$ or $FeO_2^{-2}$ tetrahedron can be balanced electrically by association with $PO_2^+$ tetrahedron, a $Fe^{+2}$ or $Fe^{+3}$ cation, organic cations derived from the templating agent, or other metal cation introduced from an extraneous source. It has also been postulated that non adjacent $AlO_2^-$ and $PO_2^+$ tetrahedral pairs can be balanced by $Na^+$ and $OH^-$, respectively [Flanigen and Grose, Molecular Sieve Zeolites-I, ACS, Washington, D.C. (1971)].

TAPO MOLECULAR SIEVES

TAPO molecular sieves are disclosed in U.S. Pat. No. 4,500,561, incorporated herein by reference, and comprise a three dimensional microporous crystal framework structure of $[TiO_2]$, $AlO_2$]and $[PO_2]$ tetrahedral units which has a unit empirical formula on an anhydrous basis of:

$mR:(Ti_xAl_yP_z)O_2$ wherein "R" represents at least one organic templating agent present in the intracrystalline pore system; "m" represents the moles of "R" present per mole of $(Ti_xAl_yP_z)O_2$ and has a value of between zero and a 5.0, the maximum value in each case depending upon the molecular dimensions of the templating agent and the available void volume of pore system of the particular titanium molecular sieve; "x", "y" and "z" represent the mole fractions of titanium, aluminum and phosphorus, respectively, present as tetrahedral oxides, representing the following values for "x", "y" and "z":

| Point | Mole Fraction | | |
|---|---|---|---|
| | x | y | z |
| A | 0.001 | 0.45 | 0.549 |
| B | 0.88 | 0.01 | 0.11 |
| C | 0.98 | 0.01 | 0.01 |
| D | 0.29 | 0.70 | 0.01 |
| E | 0.001 | 0.70 | 0.299 |

The parameters "x", "y" and "z" are preferably within the following values for "x", "y" and "z":

| Point | Mole Fraction | | |
|---|---|---|---|
| | x | y | z |
| a | 0.002 | 0.499 | 0.499 |
| b | 0.20 | 0.40 | 0.40 |
| c | 0.20 | 0.50 | 0.30 |
| d | 0.10 | 0.60 | 0.30 |
| e | 0.002 | 0.60 | 0.398 |

The titanium containing molecular sieves are referred to hereinafter, solely for point of reference herein as "TAPO" molecular sieves, or as "TAPOs" if the reference is to the class as a whole. This designation is simply made for the sake of convenient reference herein and is not meant to designate a particular structure for any qiven TAPO molecular sieve. The members of the class of TAPO's employed hereinafter in the examples will be characterized simply by referring to such members as TAPO-5, TAPO-11, etc, i.e., a particular species will be referred to as TAPO n where "n" is a number specific to a given class member as its preparation is reported herein. This designation is an arbitrary one and is not intended to denote structural relationship to another material(s) which may also be characterized by a numbering system.

The term "unit empirical formula" is used herein according to its common meaning to designate the simplest formula which gives the relative number of moles of titanium, aluminum and phosphorus which form the $[TiO_2]$, $[PO_2]$ and $[AlO_2]$ tetrahedral unit within a titanium-containing molecular sieve and which forms the molecular framework of the TAPO composition(s). The unit empirical formula is given in terms of titanium, aluminum and phosphorus as shown in Formula (1), above, and does not include other compounds, cations or anions which may be present as a result of the preparation or the existence of other impurities or materials in the bulk composition not containing the aforementioned tetrahedral unit. The amount of template R is reported as part of the composition when the as synthesized unit empirical formula is given, and water may also be reported unless such is defined as the anhydrous form. For convenience, coefficient "m" for template "R" is reported as a value that is normalized by dividing the number of moles of organic by the total moles of titanium, aluminum and phosphorus.

The unit empirical formula for a TAPO may be given on an "as-synthesized" basis or may be given after an "as-synthesized" TAPO composition has been subjected to some post treatment process, e.q., calcination. The term "as-synthesized" herein shall be used to refer to the TAPO composition(s) formed as a result of the hydrothermal crystallization but before the TAPO composition has been subjected to post treatment to remove any volatile components present therein. The actual value of "m" for a post treated TAPO will depend on several factors (including: the particular TAPO, template, severity of the post-treatment in terms of its ability to remove the template from the TAPO, the proposed application of the TAPO composition, and etc.) and the value for "m" can be within the range of values as defined for the as-synthesized TAPO compositions although such is generally less than the as-synthesized TAPO unless such post-treatment process adds template to the TAPO so treated. A TAPO composition which is in the calcined or other post-treatment form generally has an empirical formula represented by Formula (1), except that the value of "m" is generally less than about 0.02. Under sufficiently severe post treatment conditions, e.g., roasting in air at high temperature for long periods (over 1 hr.), the value of "m" may be zero (0) or, in any event, the template, R, is undetectable by normal analytical procedures.

The TAPO molecular sieves are generally further characterized by an intracrystalline adsorption capacity for water at 4.6 torr and about 24° C. of about 3.0 weight percent. The adsorption of water has been observed to be completely reversible while retaining the same essential framework topology in both the hydrated and dehydrated state. The term "essential framework topology" is meant to desiqnate the spatial arrangement of the primary bond linkages. A lack of change in the framework topology indicates that there is no disruption of these primary bond linkages.

The TAPO molecular sieves are generally synthesized by hydrothermal crystallization from a reaction mixture comprising reactive sources of titanium, aluminum and phosphorus, and one or more organic templating agents. Optionally, alkali metal(s) may be present in the reaction mixture. The reaction mixture is placed in a pressure vessel, preferably lined with an inert plastic material, such as polytetrafluoroethylene, and heated, preferably under the autoqenous pressure, at a temperature of at least about 100° C., and preferably between 100° C. and 250° C., until crystals of the molecular sieve product are obtained, usually for a period of from 2 hours to 2 weeks. While not essential to the synthesis of the TAPO molecular sieves, it has been found that in qeneral stirring or other moderate aqitation of the reaction mixture and/or seeding the reaction mixture with seed crystals of either the TAPO to be produced, or a topologically similar composition, facilitates the crystallization procedure. The product is recovered by any convenient method such as centrifugation or filtration.

After crystallization the TAPO(s) may be isolated and washed with water and dried in air. As a result of the hydrothermal crystallization, the as-synthesized TAPO contains within its intracrystalline pore system at least one form of the template employed in its formation. Generally, the template is a molecular species, but it is possible, steric considerations permitting, that at least some of the template is present as a charge balancing cation. Generally the template is too large to move freely through the intracrystalline pore system of the formed TAPO and may be removed by a post-treatment process, such as by calcining the TAPO at temperatures of between about 200° C. and to about 700° C. so as to thermally degrade the template or by employing some other post-treatment process for removal of at least part of the template from the TAPO. In some instances the pores of the TAPO are sufficiently large to permit transport of the template, and, accordingly, complete or partial removal thereof can be accomplished by conventional desorption procedures such as carried out in the case of zeolites.

The TAPOs are preferably formed from a reaction mixture having a mole fraction of alkali metal cation which is sufficiently low that it does not interfere with the formation of the TAPO composition. The TAPO compositions are generally formed from a reaction mixture containing reactive sources of TiO$_2$, Al$_2$O$_3$, and P$_2$O$_5$ and an organic templating agent, said reaction mixture comprising a composition expressed in terms of molar oxide ratios of:

fR$_2$O:(Ti$_x$Al$_y$P$_z$)O$_2$ g H$_2$O wherein "R" is an organic templating agent; "f" has a value large enough to constitute an effective amount of "R" said effective amount being that amount which form said TAPO compositions; "g" has a value of from zero to 500; "x", "y" and "z" represent the mole fractions, respectively of titanium, aluminum and phosphorus in the (Ti$_x$Al$_y$P$_z$)O$_2$ constituent, and each has a value of at least 0.001 and being within the following values for "x", "y" and "z":

| Point | Mole Fraction | | |
|---|---|---|---|
| | x | y | z |
| h | 0.001 | 0.989 | 0.01 |
| i | 0.001 | 0.01 | 0.989 |
| j | 0.32 | 0.24 | 0.44 |
| k | 0.98 | 0.01 | 0.01 |

Althouqh the TAPO compositions will form if higher concentrations of alkali metal cation are present, such reaction mixtures are not qenerally preferred. A reaction mixture, expressed in terms of molar oxide ratios, comprising the following bulk composition is preferred:

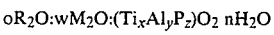

oR$_2$O:wM$_2$O:(Ti$_x$Al$_y$P$_z$)O$_2$ nH$_2$O wherein "R" is an organic template; "o" has a value great enough to constitute an effective concentration of "R" and is preferably within the range of from greater than zero (0) to about 5.0; "M" is an alkali metal cation; "w" has a value of from zero to 2.5; "n" has a value between about zero (0) and about 500; "x", "y" and "z" represent the mole fractions, respectively, of titanium, aluminum and phosphorus in (Ti$_x$Al$_y$P$_z$)O$_2$ "x", "y" and "z" represent the mole ions, respectively of titanium, aluminum and phosphorus in the (Ti$_x$Al$_y$P$_z$)O$_2$ constituent, and each has a value of at least 0.001 and being within the following values for "x", "y" and "z":

| Point | Mole Fraction | | |
|---|---|---|---|
| | x | y | z |
| h | 0.001 | 0.989 | 0.01 |
| i | 0.001 | 0.01 | 0.989 |
| j | 0.32 | 0.24 | 0.44 |
| k | 0.98 | 0.01 | 0.01 |

When the TAPOs are synthesized by this method the value of "m" in Formula (1) is generally above about 0.02.

Though the presence of alkali metal cations is not preferred, when they are present in the reaction mixture it is preferred to first admix at least a portion (e.g., at least about 10 weight percent) of each of the aluminum and phosphorus sources in the substantial absence (e.g., preferably less than about 20 percent of the total weight of the aluminum source and phosphorus source) of the titanium source. This procedure avoids adding the phosphorus source to a basic reaction mixture containing the titanium source and aluminum source, (as was done in most of the published attempts to substitute isomorphously [$PO_2$] tetrahedra for [$SiO_2$] tetrahedra in zeolitic structures). Although the reaction mechanism is by no means clear at this time, the function of the template may be to favor the incorporation of [$PO_2$] and [$AlO_2$] tetrahedra in the framework structures of the crystalline products with [$TiO_2$] tetrahedra isomorphously replacing [$PO_2$] tetrahedra.

The reaction mixture from which these TAPOs are formed contains one or more organic templating agents (templates) which can be most any of those heretofore proposed for use in the synthesis of aluminosilicates and aluminophosphates. The template preferably contains at least one element of Group VA of the Periodic Table, particularly nitroqen, phosphorus, arsenic and/or antimony, more preferably nitrogen or phosphorus and most preferably nitrogen and are of the formula $R_4X^+$ wherein X is selected from the group consisting of nitrogen, phosphorus, arsenic and/or antimony and R may be hydrogen, alkyl, aryl, aralkyl, or alkylaryl group and is preferably aryl or alkyl containing between 1 and 8 carbon atoms, although more than eight carbon atoms may be present in "R" of group of the template. Nitrogen containing templates are preferred, including amines and quaternary ammonium compounds, the latter being represented generally by the formula $R'_4N^+$ wherein each R' is an alkyl, aryl, alkylaryl, or araalkyl group; wherein R' preferably contains from 1 to 8 carbon atoms or higher when R' is alkyl and greater than 6 carbon atoms when R' is otherwise, as hereinbefore discussed. Polymeric quaternary ammonium salts such as $[(C_{14}H_{32}N_2)(OH)_2]_x$ wherein "x" has a value of at least 2 may also be employed. The mono-, di- and triamines, including mixed amines, may also be employed as templates either alone or in combination with a quaternary ammonium compound or another template. The exact relationship of various templates when concurrently employed is not clearly understood. Mixtures of two or more templating agents can produce either mixtures of TAPOs or in the instance where one template is more strongly directing than another template the more strongly directing template may control the course of the hydrothermal crystallization wherein with the other template serving primarily to establish the pH conditions of the reaction mixture.

Representative templates include tetramethylammonium, tetraethylammonium, tetrapropylammonium or tetrabutylammonium ions; di-n-propylamine; tripropylamine; triethylamine; triethanolamine; piperidine; cyclohexylamine; 2-methylpyridine; N,N-dimethylbenzylamine; N,N-diethylethanolamine; dicyclohexylamine; N,N-dimethylethanolamine; 1,4-diazabicyclo (2,2,2) octane; N-methyldiethanolamine, N-methylethanolamine; N-methylcyclohexylamine; 3-methylpyridine; 4-methylpyridine; quinuclidine; N,N'-dimethyl-1,4-diazabicyclo (2,2,2) octane ion; di-n-butylamine, neopentylamine; di-n-pentylamine; isopropylamine; t-butylamine; ethylenediamine; pyrrolidine; and 2-imidazolidone. As will be readily apparent from the illustrative examples set forth hereinafter, not every template will produce every TAPO composition although a single template can, with proper selection of the reaction conditions, cause the formation of different TAPO compositions, and a given TAPO composition can be produced using different templates.

In those instances where an aluminum alkoxide is the reactive aluminum source, the corresponding alcohol is necessarily present in the reaction mixture since it is a hydrolysis product of the alkoxide. It has not as yet been determined whether this alcohol participates in the synthesis process as a templating agent, or in some other function and, accordingly, is not reported as a template in the unit formula of the TAPOs, although such may be acting as templates.

Alkali metal cations, if present in the reaction mixture, may facilitate the crystallization of certain TAPO phases, although the exact function of such cations, when present, in crystallization, if any, is not presently known. Alkali cations present in the reaction mixture generally appear in the formed TAPO composition, either as occluded (extraneous) cations and/or as sstructural cations balancing net negative charges at various sites in the crystal lattice. It should be understood that although the unit formula for the TAPOs does not specifically recite the presence of alkali cations they are not excluded in the same sense that hydrogen cations and/or hydroxyl groups are not specifically provided for in the traditional formulae for zeolitic aluminosilicates.

Most any reactive titanium source may be employed herein. The preferred reactive titanium sources include titanium alkoxides, water-soluble titanates and titanium chelates.

Most any reactive phosphorous source may be employed. Phosphoric acid is the most suitable phosphorus source employed to date. Accordingly, other acids of phosphorus are generally believed to be suitable phosphorus scurces for use herein. Organic phosphates such as triethyl phosphate have been found satisfactory, and so also have crystalline or amorphous aluminophosphates such as the $AlPO_4$ compositions of U.S. Pat. No. 4,310,440. Organo-phosphorus compounds, such as tetrabutyl-phosphonium bromide have not, apparently, served as reactive sources of phosphorus, but these compounds do function as templating agents and may also be capable of being suitable phosphorus sources under proper process conditions (yet to be ascertained). Organic phosphorus compounds, e.g., esters, are believed to be generally suitable since they can generate acids of phosphorus in situ. Conventional phosphorus salts, such as sodium metaphosphate, may be used, at least in part as the phosphorus source, but they are not preferred.

Most any reactive aluminum source may be employed herein. The preferred reactive aluminum sources include aluminum alkoxides, such as aluminum isopropoxide, and pseudoboehmite. Crystalline or amorphous aluminophosphates which are a suitable source of phosphorus are, of course, also suitable sources of aluminum. Other sources of aluminun used in zeolite synthesis, such as gibbsite, sodium aluminate and aluminum trichloride, can be employed but as generally not preferred.

Since the exact nature of the TAPO molecular sieves are not clearly understood at present, although all are believed to contain [$TiO_2$] tetrahedra in the three-dimensional microporous crystal framework structure, it is advantageous to characterize the TAPO molecular sieves by means of their chemical composition. This is due to the low level of titanium present in certain of the TAPO molecular sieves prepared to date which makes it difficult to ascertain the exact nature of the interaction between titanium, aluminum and phosphorus. As a result, although it is believed that titanium, [$TiO_2$], has substituted isomorphously for [$AlO_2$] or [$PO_2$] tetrahedra, it is appropriate to characterize certain TAPO compositions by reference to their chemical composition in terms of the mole ratios of oxides in the as-synthesized and anhydrous form as:

$$vR:pTiO_2:qAl_2O_3:rP_2O_5$$

wherein "R" represents at least one organic templating agent present in the intracrystalline pore system; "v" represents an effective amount of the organic templating agent to form said TAPO compositions and preferably has a value between and including zero and about 3.0; "p", "q" and "r" represent moles, respectively, of titanium, alumina and phosphorus pentaoxide, based on said moles being such that they are within the following values for "p", "q" and "r":

| Point | Mole Fraction | | |
|-------|-------|-----|--------|
|       | p     | q   | r      |
| A     | 0.004 | 1.0 | 1.22   |
| B     | 176   | 1.0 | 11.0   |
| C     | 196   | 1.0 | 1.0    |
| D     | 0.828 | 1.0 | 0.0143 |
| E     | 0.003 | 1.0 | 0.427  |

The parameters "p", "q" and "r" are preferably within the following values for "p", "q" and "r":

| Point | Mole Fraction | | |
|-------|-------|-----|------|
|       | p     | q   | r    |
| a     | 0.008 | 1.0 | 1.0  |
| b     | 1.0   | 1.0 | 1.0  |
| c     | 0.80  | 1.0 | 0.60 |
| d     | 0.333 | 1.0 | 0.50 |
| e     | 0.067 | 1.0 | 0.663 |

ELAPO MOLECULAR SIEVES

"ELAPO" molecular sieves are a class of crystalline molecular sieves in which at least one element capable of forming a three-dimensional microporous framework form crystal framework structures of $AlO_2^-$, $PO_2^+$ and $MO_2^n$ tetrahedral oxide units wherein "$MO_2^n$" represents at least one different element (other than Al or P) present as tetrahedral oxide units "$MO_2^n$" with charge "n" where "n" may be $-3$, $-2$, $-1$, 0 or $+1$. The members of this novel class of molecular sieve compositions have crystal framework structures of $AlO_2^-$, $PO_2^+$ and $MO_2^n$ tetrahedral units and have an empirical chemical composition on an anhydrous basis expressed by the formula:

$$mR:(M_xAl_yP_z)O_2$$

wherein "R" represents at least one organic templating agent present in the intracrystalline pore system; "m" represents the molar amount of "R" present per mole of $(M_xAl_yP_z)O_2$; "M" represents at least one capable of forming framework tetrahedral oxides; and "x", "y" and "z" represent the mole fractions of "M", aluminum and phosphorus, respectively, present as tetrahedral oxides. "M" is at least one different elements ($M_1$) such that the molecular sieves contain at least one framework tetrahedral units in addition to $AlO_2^-$ and $PO_2^+$. "M" is at least one element selected from the group consisting of arsenic, beryllium, boron, chromium, gallium, germanium and lithium, and when "M" denotes two elements the second element may be one of the aforementioned and/or is at least one element selected from the group consisting of cobalt, iron, magnesium, manganese, titanium and zinc. ELAPOs and their preparation are disclosed in European Patent Application Ser. No. 85104386.9, filed Apr. 11, 1985 (EPC Publication No. 0158976, published Oct. 13, 1985, incorporated herein by reference) and 85104388.5, filed Apr. 11, 1985 (EPC Publication No. 158349, published Oct. 16, 1985, incorporated herein by reference).

The ELAPO molecular sieves are generally referred to herein by the acronym or "ELAPO" to designate element(s) "M" in a framework of $AlO_2^-$, $PO_2^+$ and $MO_2^n$ tetrahedral oxide units. Actual class members will be identified by replacing the "EL" of the acronym with the elements present as $MO_2^n$ tetrahedral units. For example, "MgBeAPO" designates a molecular sieve comprised of $AlO_2^-$, $PO_2^+$, $MgO_2^{-2}$ and $BeO_2^{-2}$ tetrahedral units. To identify various structural species which make up each of the subgeneric classes, each species is assigned a number and is identified as "ELAPO i" wherein "i" is an integer. The given species designation is not intended to denote a similarity in structure to any other species denominated by a similar identification system.

The ELAPO molecular sieves comprise at least one additional element capable of forming framework tetrahedral oxide units ($MO_2^n$) to form crystal framework structures with $AlO_2^-$ and $PO_2^+$ tetrahedral oxide units wherein "M" represents at least one element capable of forming tetrahedral units "$MO_2^n$", where "n" is $-3$, $-2$, $-1$, 0 or $+1$ and is at least one element selected from the group consisting of arsenic, beryllium, boron, chromium, gallium, germanium and lithium. When "M" denotes two elements "M" may also be at least one element selected from the group consisting of cobalt, iron, magnesium, manganese, titanium and zinc. For example, in each instance "M" includes at least one of the first group of elements, e.g., As, Be, etc., and when two or more elements are present, the second and further elements may be selected from the first group of elements and/or the second group of elements, as above discussed.

The ELAPO molecular sieves have crystalline three-dimensional microporous framework structures of $AlO_2^-$, $PO_2^+$ and $MO_2^n$ tetrahedral units and have an empirical chemical composition on an anhydrous basis expressed by the formula:

$$mR:(M_xAl_yP_z)O_2;$$

wherein "R" represents at least one organic templating agent present in the intracrystalline pore system; "m" represents the molar amount of "R" present per mole of $(M_xAl_yP_z)O_2$ and has a value of zero to about 0.3; "M" represents at least one element capable of forming framework tetrahedral oxides where "M" is at least one element selected from the group consisting of arsenic, beryllium, boron, chromium, gallium, germanium and lithium. When "M" includes an additional element such additional elements "M" may be at least one element selected from the group consisting of cobalt, iron, magnesium, manganese, titanium, and zinc.

The relative amounts of element(s) "M", aluminum and phosphorus are expressed by the empirical chemical formula (anhydrous):

$$mR: (M_xAl_yP_z)O_2$$

where "x", "y" and "z" represent the mole fractions of said "M", aluminum and phosphorus. The individual mole fractions of each "M" (or when M denotes two or more elements, $M_1$, $M_2$, $M_3$, etc.) may be represented by "$x_1$", "$x_2$", "$x_3$", etc. wherein "$x_1$", "$x_2$", and "$x_3$", and etc. represent the individual mole fractions of elements $M_1$, $M_2$, $M_3$, and etc. for "M" as above defined. The values of "$x_1$", "$x_2$", "$x_3$", etc. are as defined for "x", hereinafter, where "$x_1$"+"$x_2$" "$x_3$" . . . ="x" and where $x_1$, $x_2$, $x_3$, etc. are each at least 0.01.

The ELAPO molecular sieves have crystalline three-dimensional microporous framework structures of $MO_2^n$, $AlO_2^-$ and $PO_2^+$ tetrahedral units having an empirical chemical composition on an anhydrous basis expressed by the formula:

$$mR:(M_xAl_yP_z)O_2$$

wherein "R" represents at least one organic templating agent present in the intracrystalline pore system; "m" represents a molar amount of "R" present per mole of $(M_xAl_yP_z)O_2$ and has a value of zero to about 0.3; "M" represents at least one different element (other than Al or P) capable of forming framework tetrahedral oxides, as hereinbefore defined, and "x", "y" and "z" represent the mole fractions of "M", aluminum and phosphorus, respectively, present as tetrahedral oxides; said mole fractions "x", "y" and "z" being generally defined as within the following values for "x", "y", and "z":

| Point | Mole Fraction | | |
|---|---|---|---|
| | x | y | z |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

In a preferred sub-class of the ELAPOs of this invention, the values of "x", "y" and "z" in the formula above are within the following values for "x", "y" and "z":

| Point | Mole Fraction | | |
|---|---|---|---|
| | x | y | z |
| a | 0.02 | 0.60 | 0.38 |
| b | 0.02 | 0.38 | 0.60 |
| c | 0.39 | 0.01 | 0.60 |
| d | 0.60 | 0.01 | 0.39 |
| e | 0.60 | 0.39 | 0.01 |
| f | 0.39 | 0.60 | 0.01 |

ELAPO compositions are generally synthesized by hydrothermal crystallization from a reaction mixture containing reactive sources of the elements "M", aluminum and phosphorus, preferably an organic templating, i.e., structure directing, agent, preferably a compound of an element of Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the ELAPO product are obtained, usually a period of from several hours to several weeks. Typical crystallization times are from about 2 hours to about 30 days with from about 2 hours to about 20 days being generally employed to obtain crystals of the ELAPO products. The product is recovered by any convenient method such as centrifugation or filtration.

In synthesizing the ELAPO compositions of the instant invention, it is preferred to employ a reaction mixture composition expressed in terms of the molar ratios as follows:

$$aR:(M_xAl_yP_z)O_2:bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and 300; "M" represents at least one element, as above described, capable of forming tetrahedral oxide framework units, $MO_2^n$, with $AlO_2^-$ and $PO_2^+$ tetrahedral units; "n" has a value of −3, −2, −1, 0 or +1; and "x", "y" and "z" represent the mole fractions of "M", aluminum and phosphorus, respectively, "y" and "z" each have a value of at least 0.01 and "x" has a value of at least 0.01 with each element "M" having a mole fraction of at least 0.01. The mole fractions "x", "y" and "z" are preferably within the following values for "x" "y" and "z":

| Point | Mole Fraction | | |
|---|---|---|---|
| | x | y | z |
| F | 0.01 | 0.60 | 0.39 |
| G | 0.01 | 0.39 | 0.60 |
| H | 0.39 | 0.01 | 0.60 |
| I | 0.98 | 0.01 | 0.01 |
| J | 0.39 | 0.60 | 0.01 |

In the foregoing expression of the reaction composition, the reactants are normalized with respect to a total of $(M+Al+P)=(x+y+z)=1.00$ mole, whereas in many of the working examples appearing hereinafter the reaction mixtures are expressed in terms of molar oxide ratios and may be normalized to 1.00 mole of $P_2O_5$. This latter form is readily converted to the former form by routine calculations by dividing the total number of moles of "M", aluminum and phosphorus into the moles of each of "M", aluminum and phosphorus. The moles of template and water are similarly normalized by dividing the total moles of "M", aluminum and phosphorus.

In forming the reaction mixture from which the instant molecular sieves are formed the organic templating agent can be any of those heretofore proposed for use in the synthesis of conventional zeolite aluminosilicates. In general these compounds contain elements of Group VA of the Periodic Table of Elements, particularly nitrogen, phosphorus, arsenic and antimony, preferably nitrogen or phosphorus and most preferably nitrogen, which compounds also contain at least one alkyl or aryl group having from 1 to 8 carbon atoms. Particularly preferred compounds for use as templating agents are the amines, quaternary phosphonium compounds and quaternary ammonium compounds, the latter two being represented generally by the formula $R_4X^+$ wherein "X" is nitrogen or phosphorus and each R is an alkyl or aryl group containing from 1 to 8 carbon atoms Polymeric quaternary ammonium salts such as $[(C_{14}H_{32}N_2)(OH)_2]_x$ wherein "x" has a value of at least 2 are also suitably employed. The mono-, di- and tri-amines are advantageously utilized, either alone or in combination with a quaternary ammonium compound or other templating compound. Mixtures of two or more templating agents can either produce mixtures of the desired ELAPOs or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; tetrapentylammonium ion; di-n-propylamine; tripropylamine; triethylamine; triethanolamine; piperidine; cyclohexylamine; 2-methylpyridine; N,N-dimethylbenzylamine; N,N dimethylethanolamine; choline; N,N'-dimethylpiperazine; 1,4-diazabicyclo (2,2,2,) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4 diazabicyclo (2,2,2) octane ion; di-n-butylamine, neopentylamine; di-n-pentylamine; isopropylamine; t-butylamine; ethylenediamine; pyrrolidine; and 2-imidazolidone. Not every templating agent will direct the formation of every species of ELAPO, i.e., a single templating agent can, with proper manipulation of the reaction conditions, direct the formation of several ELAPO compositions, and a given ELAPO composition can be produced using several different templating agents.

The phosphorus source is preferably phosphoric acid, but organic phosphates such as triethyl phosphate may be satisfactory, and so also may crystalline or amorphous aluminophosphates such as the AlPO$_4$ composition of U.S. Pat. No. 4,310,440. Organo phosphorus compounds, such as tetrabutylphosphonium bromide, do not apparently serve as reactive sources of phosphorus, but these compounds may function as templating agents. Conventional phosphorus salts such as sodium metaphosphate, may be used, at least in part, as the phosphorus source, but are not preferred.

The aluminum source is preferably either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The element(s) "M" can be introduced into the reaction system in any form which permits the formation in situ of reactive form of the element, i.e., reactive to form the framework tetrahedral oxide unit of the element. The organic and inorganic salts, of "M" such as oxides, alkoxides, hydroxides, halides and carboxylates, may be employed including the chlorides, bromides, iodides, nitrates, sulfates, acetates, formates, ethoxides, propoxides and the like.

While not essential to the synthesis of ELAPO compositions, stirring or other moderate agitation of the reaction mixture and/or seeding the reaction mixture with seed crystals of either the ELAPO species to be produced or a topologically similar species, such as aluminophosphate, aluminosilicate or molecular sieve compositions, facilitates the crystallization procedure.

After crystallization the ELAPO product may be isolated and advantageously washed with water and dried in air. The as-synthesized ELAPO generally contains within its internal pore system at least one form of the templating agent employed in its formation. Most commonly the organic moiety is present, at least in part, as a charge balancing cation as is generally the case with as-synthesized aluminosilicate zeolites prepared from organic-containing reaction systems. It is possible, however, that some or all of the organic moiety is an occluded molecular species in a particular ELAPO species. As a general rule the templating agent, and hence the occluded organic species, is too large to move freely through the pore system of the ELAPO product and must be removed by calcining the ELAPO at temperatures of 200° C. to 700° C. to thermally degrade the organic species. In a few instances the pores of the ELAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as synthesized" as used herein does not include the condition of the ELAPO phase wherein the organic moiety occupying the intracrystalline pore system as a result of the hydrothermal crystallization process has been reduced by post-synthesis treatment such that the value of "m" in the composition formula:

$$mR:(M_xAl_yP_z)O_2$$

has a value of less than 0.02. The other symbols of the formula are as defined hereinabove. In those preparations in which an alkoxide is employed as the source of element "M", aluminum or phosphorus, the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as-synthesized ELAPO material.

Since the present ELAPO compositions are formed from $MO_2^n$, $AlO_2$, and $PO_2^+$ tetrahedral oxide units which, respectively, have a net charge of "n", (where "m" may be $-3$, $-2$, $-1$, 0 or $+1$), $-1$ and $+1$, the matter of cation exchangeability is considerably more complicated than in the case of zeolitic molecular sieves in which, ideally, there is a stoichiometric relationship between $AlO_2^-$ tetrahedra and charge-balancing cations. In the instant compositions, an $AlO_2^-$ tetrahedron can be balanced electrically either by association with a $PO_2^+$ tetrahedron or a simple cation such as an alkali metal cation, a proton (H+), a cation of "M" present in the reaction mixture, or an organic cation derived from the templating agent. Similarly an $MO_2^n$ tetrahedron, where "n" is negative, can be balanced electrically by association with $PO_2^+$ tetrahedra, a cation of "M" present in the reaction mixture, organic cations derived from the templating agent, a simple cation such as an alkali metal cation, or other divalent or polyvalent maetal cation, a proton (H+), anions or cations introduced from an extraneous source. It has also been postulated that non-adjacent $AlO_2^-$ and $PO_2^+$ tetrahedral pairs can be balanced by $Na^{30}$ and $OH^-$respectively [Flanigen and Grose, Molecular Sieve Zeolites-I, ACS, Washington, DC (1971)]

SILICOALUMINOPHOSPHATE MOLECULAR SIEVES

The preferred NZMS are the silicoaluminophosphate molecular sieves described in U.S. Pat. No. 4,440,871. The use of such catalysts in reforming catalysts or as components in heretofore employed reforming/dehydrocyclization catalysts provides improved catalysts and provide products characterized by an improved selectivity to iso-products and provides improved activity in reforming/dehydrocyclization reactions.

The silicoaluminophosphate molecular sieves of U.S. Pat. No. 4,440,871 are disclosed as microporous crystalline silicoaluminophosphates, the pores of which are uniform and have nominal diameters of greater than about 3 Angstroms and whose essential empirical chemical composition in the as-synthesized and anhydrous form is:

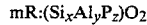

wherein "R" represents at least one organic templating agent present in the intracrystalline pore system; "m" represents the moles of "R" present per mole of $(Si_xAl_yP_z)O_2$ and has a value of from 0.02 to 0.3 , "x", "y" and "z" represent the mole fractions of silicon, aluminum and phosphorus, respectively, present as tetrahedral oxides, said mole fractions being such that they are within the pentagonal compositional area defined by points A, B, C, D and E of the ternary diagram of FIG. 1 and are preferably within the pentagonal compositional area defined by points a, b, c, d and e of FIG. 2 of U.S. Pat. No. 4,440,871. The SAPO molecular sieves of U.S. Pat. No. 4,440,871 are also described as silicoaluminophosphates having a three-dimensional microporous framework structure of $PO_2^+$, $AlO_2^-$ and $SiO_2$ tetrahedral units, and whose essential empirical chemical composition on an anhydrous basis is:

wherein "R" represents at least one organic templating agent present in the intracrystalline pore system; "m" represents the moles of "R" present per mole of $(Si_xAl_yP_z)O_2$ and has a value of from zero to 0.3; "x", "y" and "z" represent, respectively, the mole fractions of silicon, aluminum and phosphorus present in the oxide moiety, said mole fractions being within the compositional area bounded by points A, B, C, D and E on the ternary diagram which is FIG. 1 of U.S. Pat. No. 4,440,871, said silicoaluminophosphate having a characteristic X-ray powder diffraction pattern which contains at least the d spacings set forth below in any one of Tables I, III, V, VII, IX, XIII, XVII, XXI, XXIII or XXV of U.S. Pat. No. 4,440,871. Further, the as-synthesized crystalline silicoaluminophosphates of U.S. Pat. No. 4,440,871 may be calcined at a temperature sufficiently high to remove at least some of any organic templating agent present in the intracrystalline pore system as a result of such synthesis. The silicoaluminophosphates of U.S Pat. No. 4,440,871 are generally referred to therein as "SAPO", as a class, or as "SAPO-n" wherein "n" is an integer denoting a particular SAPO as its preparation is reported in U S. Pat. No. 4,440,871. The preparation of the SAPOs is disclosed in U.S. Pat. No. 4,440,871, incorporated herein by reference.

MP-SAPOs characterized by the aforementioned isobutane and triethylamine adsorption characteristics include SAPO-11, SAPO-31, SAPO-40 and SAPO-41.

The species SAPO-11 as referred to herein is a silicoaluminophosphate material having a three-dimensional microporous crystal framework structure of $PO_2^+$, $AlO_2^+$, and $SiO_2$ tetrahedral units, and whose essential empirical chemical composition on an anhydrous basis is:

wherein "R" represents at least one organic templating agent present in the intracrystalline pore system; "m" represents the moles of "R" present per mole of $(Si_xAl_yP_z)O_2$ and has a value of from zero to 0.3; , "y" and "z" represent, respectively, the mole fractions of silicon, aluminum and phosphorus present in the oxide moiety, said mole fractions being within the compositional area bounded by points A, B, C, D and E on the ternary diagram which is FIG. 1 of U.S. Pat. No. 4,440,871, and preferably withIn the area bounded by points a, b, c, d and e on the ternary diagram which is FIG. 2 of U.S. Pat. No. 4,440,871, said silicoaluminophosphate having a characteristic X-ray powder diffraction pattern which contains at least the d spacings set forth below:

| | SAPO 11 | |
|---|---|---|
| $2\theta$ | d(Å) | Relative Intensity |
| 9.4–9.65 | 9.41–9.17 | m |
| 20.3–20.6 | 4.37–4.31 | m |
| 21.0–21.3 | 4.23–4.17 | vs |
| 21.1–22.35 | 4.02–3.99 | m |
| 22.5–22.9 (doublet) | 3.95–3.92 | m |
| 23.15–23.35 | 3.84–3.81 | m–s |

The species SAPO-31 as referred to herein is a silicoaluminophosphate having a three-dimensional microporous crystal framework structure of $PO_2^+$, $AlO_2^-$ and $SiO_2$ tetrahedral units, and whose essential empirical chemical composition on an anhydrous basis is:

wherein "R" represents at least one organic templating agent present in the intracrystalline pore system; "m" represents the moles of "R" present per mole of $(Si_xAl_yP_z)O_2$ and has a value of from zero to 0.3; , "y" and "z" represent, respectively, the mole fractions of silicon, aluminum and phosphorus present in the oxide moiety, said mole fractions being within the compositional area bounded by points A, B, C, D and E on the ternary diagram which is FIG. 1 of U.S. Pat. No. 4,440,871, and preferably within the area bounded by points a, b, c, d and e on the ternary diagram which is FIG. 2 of U.S. Pat. No. 4,440,871, said silicoaluminophosphate having a characteristic X-ray powder diffraction pattern which contains at least the d-spacings set forth below:

| | SAPO-31 | |
|---|---|---|
| 2θ | d(Å) | Relative Intensity |
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

The species SAPO-40 as referred to herein is a silicoaluminophosphate material having a three-dimensional microporous crystal framework structure of $PO_2^+$, $AlO_2^-$ and $SiO_2$ tetrahedral units, and whose essential empirical chemical composition on an anhydrous basis is:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3; , "y" and "z" represent, respectively, the mole fractions of silicon, aluminum and phosphorus present in the oxide moiety, said mole fractions being within the compositional area bounded by points A, B, C, D and E on the ternary diagram which is FIG. 1of U.S. Pat. No. 4,440,871, or preferably within the area bounded by points a, b, c, d and e on the ternary diagram which is FIG. 2 of U.S. Pat. No. 4,440,871, said silicoaluminophosphate having a characteristic X-ray powder diffraction pattern which contains at least the d-spacings set forth below. In the form as synthesized in accordance with the process of this invention, "m" has a value of from 0.02 to 0.3.

| | SAPO-40 | |
|---|---|---|
| 2θ | d(Å) | Relative Intensity |
| 7.5–7.7 | 11.79–11.48 | VW–M |
| 8.0–8.1 | 11.05–10.94 | S–VS |
| 12.4–12.5 | 7.14–7.08 | W–VS |
| 13.6–13.8 | 6.51–6.42 | M–S |
| 14.0–14.1 | 6.33–6.28 | W–M |
| 27.8–28.0 | 3.209–3.18 | W–M |

The species SAPO-41 as referred to herein is a silicoaluminophosphate having a three-dimensional microporous crystal framework structure of $PO_2^+$, $AlO_2^-$ and $SiO_2$ tetrahedral units, and whose essential empirical chemical composition on an anhydrous basis is:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3; "x", "y" and "z" represent, respectively, the mole fractions of silicon, aluminum and phosphorus present in the oxide moiety, said mole fractions being within the compositional area bounded by points A, B, C, D and E on the ternary diagram which is FIG. 1 of U.S. Pat. No. 4,440,871, or preferably within the area bounded by points a, b, c, d and e on the ternary diagram which is FIG. 2 of U.S. Pat. No. 4,440,871, said silicoaluminophosphate having a characteristic X-ray powder diffraction pattern which contains at least the d-spacings set forth below:

| | SAPO-41 | |
|---|---|---|
| 2θ | d(Å) | Relative Intensity |
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.44 | w–m |

NZMS-CONTAINING ISOMERIZATION CATALYSTS

The specific NZMSs employed in the instant invention are characterized in their calcined form by an adsorption of isobutane of at least 2 percent by weight, preferably at least 4 percent by weight, at a partial pressure of 500 torr and a temperature of 20° C. and are also characterized in their calcined form by an adsorption of triethylamine of less than 5 percent by weight, preferably less than 3 percent by weight, at a partial pressure of 2.6 torr and a temperature of 22° C. NZMSs characterized by the above described adsorption of isobutane and triethylamine include, but are not limited to, ELAPSO-11, ELAPSO-31, ELAPSO-41, SAPO-11, SAPO-31, SAPO-40, SAPO-41, CoAPSO-11, CoAPSO-31, CoAPSO-41, FeAPSO-11, FeAPSO-31, FeAPSO-41, MgAPSO-11, MgAPSO-31, MgAPSO-41, MnAPSO-11, MnAPSO-31, MNAPSO-41, TiAPSO-11, TiAPSO-31, TiAPSO-41, ZnAPSO-11, ZnAPSO-31, ZnAPSO-41, CoMgAPSO-11, CoMgAPSO-31, CoMgAPSO-41, CoMnMgAPSO-11, CoMnMgAPSO-31, CoMgMnAPSO-41, MeAPO-11, MeAPO-31, MeAPO-41, TAPO-11, TAPO-31, TAPO-41, FAPO-11, FAPO-31, FAPO-41, and mixtures thereof.

The above characterization of the NZMSs employed in the instant invention relates to an adsorption characterization that is carried out on a NZMS which has been subjected to a post synthesis treatment, e.g., calcination or chemical treatment, to remove at least a portion, preferably a substantial portion, of the template "R" which is present as a result of synthesis. Although a particular NZMS is characterized herein by reference to its adsorption of isobutane and triethylamine as being to the adsorption characteristics of the NZMS in its calcined form, the instant invention necessarily includes the use of a non calcined or modified NZMSs which may be characterized by such adsorption in its modified or calcined form. For example, upon use of such a non calcined NZMS in the instant process at effective isomerization process conditions the NZMS may be calcined or hydrothermally treated in situ so as to have the characteristic adsorption of isobutane or triethylamine. Thus, the NZMS may be rendered in situ to a form characterized by the aforementioned adsorption characteristics. For example, an as-synthesized MgAPO-11 or MgAPSO 11 may not be characterized by the aforementioned adsorption of isobutane and triethylamine due to the presence of template "R" which is present as a result of synthesis, althouqh the calcined form of MgAPO-11 and MgAPSO-11 will be characterized by the aforementioned adsorption of isobutane and triethylamine. Thus, reference to a NZMS having a particular adsorption characteristic in its calcined or anhydrous form is not intended to exclude the use of the NZMS in its as-synthesized form which upon in situ calcination, hydrothermal treatment and/or other treatment, e.g., ion exchange with suitable atoms, would have such adsorption characteristics.

In one embodiment NZMSs may be employed in conjunction with traditional xylene isomerization catalysts and optionally, e.g., a zeolite aluminosilicate, isomerization component may be employed in conjunction with the NZMS containing isomerization component of this invention. The isomerization component of such catalysts may be any aluminosilicate or silicate heretofore employed as a component in isomerization catalysts. Representative of such crystalline zeolitic such that the weight ratio of the aluminosilicate and/or silicate to NZMS is between about 1:100 and about 100:1 aluminosilicates and crystalline silicates are ferrierite, silicalite, omega, ZSM type zeolites and mixtures thereof. The term "ZSM-type" zeolites is generally employed in the art to refer to those zeolites denominated by the nomenclature "ZSM n" where "n" is an integer. The ZSM type aluminosilicates include but are not limited to ZSM-5, ZSM-11, ZSM-12, ZSM-23, ZSM-35, ZSM-38, ZSM-48; and other similar materials designated by the patent and non patent literature by nomenclature "ZSM n" where "n" is an integer.

The catalysts of the instant invention comprise an effective amount of at least one NZMS, as above characterized, to provide for the isomerization of a mixture of xylene to provide an increase in the concentration of a desired xylene component, preferably para-xylene, as discussed and characterized. The composition of the finished catalyst will depend at least in part, on the composition of the selected feedstock and on the desired product distribution of xylenes to be obtained therefrom, but in all instances an effective amount of at least one NZMS is employed to provide an increase in the product mixture of at least one of the xylene components, as compared to the starting feedstock xylene content for the desired component. Further, one or more hydrogenation components comprising Pt, Pd, Ni and the like may be employed. Surprisingly, it has been discovered that the hydrogenation metal component is preferably added to the NZMS as a separate component associated with an appropriate carrier, e.g., the inorganic oxide matrix component. This is contrasted with isomerization catalysts containing zeolites where the metal component is added by ion exchange of the zeolite.

The isomerization catalysts of this invention are typically employed with an inorganic oxide component which may be any of the inorganic oxide components which have been employed heretofore in the formulation of isomerization catalysts including: amorphous inorganic oxides, e.g., clays, silicas, aluminas, and the like and mixtures thereof. The preferred inorganic oxide matrix component is a non catalytically active matrix component such as a silica.

XYLENE ISOMERIZATION PROCESSES

The instant process may be carried out at effective isomerization conditions as heretofore employed in such processes, e.g., Octafining and LTI. For example, isomerization is generally carried out at temperatures between about 500° F. and about 1000° F., at pressures between about 100 psig and 900 psig, a LVSV of between about 0.1 and about 20 and a hydrogen to hydrocarbon molar ratio between zero (0) and about 20 and may be in the liquid or vapor phase. Octafining is described in the BACKGROUND OF THE INVENTION, said discussion incorporated herein. The LTI process is generally operated in the liquid phase at temperatures of 500° F. to 660° F. under pressure sufficient to liquefy the charge. Aside from the need to maintain liquid phase conditions, pressure does not seem to be a critical parameter and will be dictated in the usual case by economic and engineering considerations. Excessively high pressures, about 1000 p.s.i.g. will be generally undesirable, though fully operative, because of the great strength of reaction vessel walls required at high pressure, making the equipment unnecessarily expensive and requiring expensive compression stages. Space velocities will vary in the range of 0.1 to about 50 volumes of charge per volume of catalyst per hour (liquid hourly space velocity, LHSV), preferably between about 0.1 to about 10 In general, temperature and LHSV will be coordinated to provide a desired severity which will provide an adequate degree of xylene isomerization and ethylbenzene conversion without excessive losses to by-products.

The instant invention is particularly beneficial in two embodiments. In one embodiment a mixture of xylenes and, optionally, ethylbenzene is contacted under effective isomerization conditions with a catalyst containing at least one NZMS effective in the isomerization of ortho- and meta-xylene to para-xylene. This isomerization is not generally carried out in the presence of hydrogen. In another embodiment an aromatic feedstock containing aromatics having 8 carbon atoms and containing, optionally, ethylbenzene is contacted under effective conditions in the presence of a NZMS, hydrogen and a hydro-dehydrogenation catalyst component for the conversion of ethylbenzene to one or more xylene products. In addition, ortho- and meta-xylenes present in such $C_8$ aromatic mixtures may undergo isomerization to para-xylene.

NZMS PREPARATION

Several non zeolitic molecular sieves were prepared in accordance with the aforementioned discussion for use in the following examples. The NZMS were prepared as follows for each example:

NZMS for Example 1

SAPO-5 was prepared by adding 69.1 grams of CATAPAL TM alumina to 115.3 grams of 85% orthophosphoric ($H_3PO_4$) in 111.6 grams of $H_2O$. A slurry of 0.375 grams NaOH, 508.6 grams of 40% solution of tetrapropylammonium hydroxide and 13.0 grams of CABOSIL ™ silica was added to the previous mixture. The composite was blended to form a homogeneous mixture and then digested at 217° C. for 112 hours. The product was water washed, dried then calcined in air at 600° C. for one hour to remove organic template.

NSMS for Example 2

SAPO-11 was prepared as follows: 115.3 grams of 85% phosphoric acid was dissolved in 200 ml. of water; this solution was added to 204.3 grams of aluminum isopropoxide with stirring and cooling. 10.0 grams of LUDOX-LS ™ silica gel and 30 ml. of $H_2O$ were added to the above mixture followed by 50.5 grams of dipropylamine and about 100 ml. of $H_2O$. The resulting mixture was blended to form a homogeneous mixture and then digested at 150° C. for 136 hours. The product was water washed, dried and calcined in air at 500° C. for 2 hours to remove organic template.

NZMS for Example 3

MAPO-11 was prepared as follows: 646 grams $H_2O$, 174.3 grams CATAPAL ™ alumina and 323.2 grams of 85% H were blended to form a gel to which was added 50.1 grams of magnesium acetate tetrahydrate dissolved in 175 grams $H_2O$. To the above mixture was added 142 grams of di-isopropyl amine and the resulting mixture was stirred to form a homogeneous mixture and then digested at 205° C. for 8 days. The product was water washed, dried and calcined in air at 500° C. for 11 days.

NZMS for Example 4

SAPO-31 was prepared by blending 81.7 grams of aluminum isopropoxide, 46.1 grams of 85% orthophosphoric acid, 24.0 grams of LUDOX ™ LS silica gel, 20.2 grams of di-n-propylamine and 161.8 grams of water, blending to insure a homogeneous mixture; to the above mixture there was added 5.6 grams of $AlPO_4$-31 as seed crystals. The final composite was then digested for 3.8 days at 200° C., water washed, dried and calcined in air at 550° C. for 2 hours to remove organic template.

NZMS for Example 5

SAPO-40 was prepared by adding 22.1 grams of CATAPAL ™ alumina to 36.9 grams of 85% orthophosphoric acid dissolved in 35.72 grams of water. To this mixture was added 162.8 grams of a 40% tetrapropylammonium hydroxide solution containing 0.12 grams of sodium hydroxide. The resulting mixture was blended to form a homogeneous mixture and then digested for one day at 225° C.. The product was water washed and dried. X-ray analysis indicated at least a 25% SAPO-5 impurity phase. The product was calcined in air to remove organic template.

NZMS for Example 6

SAPO-5 was obtained by adding 27.2 grams of CATAPAL ™ alumina to a solution of 41.3 grams of 85% orthophosphoric acid in 121.5 grams of $H_2O$. To this mixture was added a slurry of 0.6 grams CABOSIL ™ silica in 28.7 grams of tripropylamine. The mixture was blended to form a homogeneous mixture and then digested at 150° C. for 72 hours, then water washed, dried and calcined.

NZMS for Example 7

SAPO-11 was prepared by blending 67.9 grams of CATAPAL ™ alumina into a solution containing 114.6 grams of 85% orthophosphoric acid and 113.4 grams of $H_2O$. To this mixture was added a slurry of 24.3 grams CABOSIL ™ silica and 519 grams of a 25% solution (aqueous) of tetrabutyl ammonium hydroxide. To this total composite was added 101.2 grams of di-n-propyl amine. The resulting mixture was blended to form a homogeneous mixture and then digested at 202° C. for one day, water washed, dried and calcined in air at 550° C. for 2 hours to remove organic template.

EXAMPLES

The following examples were carried out to demonstrate the invention and are not intended to be limiting thereof. The evaluation of each catalyst as a xylene isomerization catalyst is reported in terms the weight percent of components in the products. Several calculations are computed as follows:

M-xylene conversion: (Weight percent meta-xylene converted to products)

Ethylbenzene conversion: (Weight percent ethylbenzene converted to products)

$$\text{Equilibrium } (P/Peq): \frac{\text{(Weight percent para-xylene in xylene product)}}{\text{(Weight percent para-xylene at thermodynamic equilibrium in xylene product at the reaction temperature)}} \times 100$$

Total xylene loss: weight percent xylene converted to other than xylene product

% m-xylene isomerization: (percent m-xylene converted to ortho- or para-xylene)

% m-xylene loss: percent of m-xylene going to products other than ortho- or para-xylene % m-xylene isomerization + % m-xylene loss = 100

(m-xylene loss) (m-xylene conversion) = 100

$$P/(P + O + M): \frac{\text{Weight of para-xylene}}{\text{Weight (para + ortho + meta-xylene)}} \times 100$$

$$P/O \text{ ratio}: \frac{\text{(Weight of para-xylene)}}{\text{(Weight of ortho-xylene)}} \times 100$$

EXAMPLES 1–5

SAPO-5, SAPO-11, MgAPO-11, SAPO-31 and SAPO-40 were evaluated as xylene isomerization catalysts. A comparative catalyst was prepared using LZ-105 was prepared according to example 8 of U.S. Pat. No. 4,257.885. LZ-105 product was washed with an acid solution (1.1 molar HCl) at 100° C. for 1 hour and then water washed until substantially all $Cl^{31}$ was removed and then dried in air at 100° C. The final acid washed LZ-105 had a $SiO_2/Al_2O_3$ molar ratio of 35.9.

The catalysts were evaluated in a micro reactor as follows.

The evaluation of a given catalyst was carried out using a micro reactor comprising a stainless steel tube [¼ inch (ID)]. Each catalyst is evaluated by employing 1 gram of catalyst as the powder by introducing the powder into the reactor. The feedstock is fed to the reactor by a syringe pump and the reactor temperature is maintained by heating the reactor in a fluidized sandbath. The sandbath temperature is controlled by a thermocouple temperature indicator located in the sand bath. The reaction temperature was monitored by a thermocouple in the catalyst bed. Prior to operation the reactor is pressurized to 100 psig with a nitrogen purge. The syringe pump is filled with a feedstock containing 100% meta-xylene. The reactor and catalyst was preheated to 800° F. or the desired temperature. The feed was then introduced into the reactor and liquid sample products collected at 0.5 hour intervals for up to five hours. Gas products were not collected. Liquid products were analyzed by vapor phase chromatography.

Table I sets forth the initial performance results of the evaluation (obtained by linear regression and interpolation to time zero) of the aforementioned catalysts. The evaluation was carried out without the use of added hydrogen and without a metal hydrogenation component. The data in Table I demonstrate the ability of catalysts prepared according to the instant invention containing SAPO-11, MAPO-11 and SAPO-31 with the characteristic adsorption properties of this invention to isomerize meta-xylene to ortho- and para-xylene and to provide this conversion with little conversion to non-$C_8$ aromatics. This result should be compared to SAPO-5 (not characterized by the adsorption properties of this invention) and LZ-105 where non-$C_8$ aromatics are formed with comparative catalyst LZ-105 converting a substantial portion of the products to non-$C_8$ aromatics. The SAPO-11, SAPO-31 and MgAPO-11 catalysts demonstrated good equilibration to xylenes homologs with low xylene loss. The ratio of para-xylene to the percent para-xylene predicted by thermodynamic equilibrium (or the "percent xylene equilibration") is greater than 80 wt. % and usually greater than 90 wt. % for each catalyst employed in the process according to this invention.

TABLE I[4]

| Example | NZMS Catalyst | % Conversion to o, p-xylenes | % Conversion[1] to Non-$C_8$ Aromatics | % Xylene Equilibration |
|---|---|---|---|---|
| 1 | SAPO-5[2] | 41.8% | 39.7% | >90 |
| 2 | SAPO-11 | 40.2% | 3.2% | >90 |
| 3 | MgAPO-11 | 32.5% | 1.8% | >90 |
| 4 | SAPO-31 | 39.0% | 15.1% | >90 |
| 5 | SAPO-40[3] | 21.7% | 53.4% | >90 |
| 6 | LZ-105[2] | 5.5% | 53.4% | >90 |

[1]Non-$C_8$ Aromatics were benzene, toluene & $C_9^+$ aromatics.
[2]Comparative Catalyst Compositions
[3]SAPO-40 sample contained at least 25 wt. % SAPO-5 impurity phase. This impurity phase is believed to account for the high % Conversion to non-$C_8$ aromatics.
[4]Results obtained by linear regression followed by interpolation to time zero to indicate initial catalyst performance.

EXAMPLE 6

The procedure described for examples 1 to 5 were repeated with a feedstock containing 17 percent by weight ethylbenzene and 83 percent by weight meta-xylene to evaluate the conversion of ethylbenzene while isomerizing meta-xylene to equilibrium and minimizing loss of valuable xylene products by use of the catalyst of the instant invention. The test conditions did not employ added hydrogen and were as follows:

| FEED: | 17 wt. % Ethylbenzene |
|---|---|
|  | 83 wt. % Meta-xylene |
| FEED RATE: | 8 cc/hour |
| PRESSURE: | 100 psig |
| TEMPERATURE | 800° F. |

The Wt. % Conversion of the Ethylbenzene (EB) was determined by the formula:

$$\text{Wt \% Conversion } EB = \frac{(\text{Wt. \% } EB \text{ in Feed}) - (\text{Wt \% } EB \text{ in Products})}{\text{Wt \% } EB \text{ in Feed}} \times 100$$

Three molecular sieves were prepared as in examples 1 to 5 using SAPO-11, SAPO-31 and LZ-105, respectively. The results of this evaluation are set forth in Table II. The results demonstrate that catalysts containing SAPO-11 and SAPO-31 were effective in the isomerization of meta-xylene and conversion of ethylbenzene and that the catalyst containing LZ-105 was not effective under these conditions as indicated by the high loss of xylene products and production of non-$C_8$-aromatic products under comparable process additions.

TABLE II[1]

| NZMS Catalyst | % m Xylene[1] to o, p xylenes | % m Xylene[1] to non $C_8$ Aromatics | % E.B.[1] Conversion | Xylene[1] Loss Ratio E.B. Conv. | % Xylene Equilibration |
|---|---|---|---|---|---|
| SAPO-11 | 40.2 | 6.6% | 20.1% | 0.33 | >90% |
| SAPO-31 | 32.8 | 0.7% | 8.1% | 0.09 | >90% |
| LZ-105 | 24.7 | 43.7% | 94.4% | 0.46 | >90% |

[1]Results obtained by linear regression followed by interpolation to time zero to indicate initial catalyst performance.

EXAMPLE 7

Two NZMSs-containing catalysts were prepared comprising SAPO-5 and SAPO-11, respectively, and a hydrogenation component. The SAPO-5 and SAPO-11 were prepared according to U.S. Pat. No. 4,440,871.

The first catalyst, a comparative catalyst, was prepared using SAPO-5 and a second catalyst, according to the instant invention, was prepared using SAPO-11. The hydrogenation component was prepared using a pseudoboehmite alumina which had been calcined at 1000° F. in air for 3 hours and then cooled to room temperature. The cooled alumina was mixed with an aqueous solution of tetraamine platinum dichloride dissolved in sufficient H₂O to fill the pore volume of the alumina component. Sufficient platinum was added to give 1.6 wt. % platinum based on the weight of alumina. The mixture was dried at 100° C. in air for 16 hours and then calcined at 1000° F. in air for 3 hours. The final Pt/Al$_2$O$_3$ product contained 1.6 wt. % platinum, based on the weight of the alumina. The two catalysts were then prepared by physically mixing 40.0 grams of the Pt/Al$_2$O$_3$ hydrogenation component with 40.0 grams of the selected SAPO and 20.0 grams of a silica (anhydrous weight) provided as a 40 percent by weight silica in water. The resulting mixture was extruded to form 1/16 inch extrudates. The extrudates were dried at 100° C. in air for about 16 hours and then calcined at 500° C. in air for 3 hours.

The two catalysts were then evaluated for the conversion of meta-xylene to ortho- and para-xylene and for the conversion of ethylbenzene. The evaluation of each catalyst was carried out in a bench scale unit using a 50 cc catalyst charge and the following test conditions:

| | TEST CONDITIONS |
|---|---|
| FEED: | 13 wt. % Ethylbenzene |
| | 65 wt. % Meta-xylene |
| | 21 wt. % Hydrogen |
| WHSV: | 1.0 (SAPO-11) |
| | 2.0 (SAPO-5) |
| TEMPERATURE | 800° F. |
| PRESSURE: | 185 psig |
| H$_2$/HYDROCARBON MOLE RATIO: | 14 |

The ethylbenzene and meta-xylene feedstock simulates the composition of C$_8$ aromatic feedstock obtained from reformate gasoline. The above conditions are similar to the conditions employed commercially for Octafining.

The liquid products were analyzed by gas chromatography for the aromatics content and the gaseous products were analyzed for C$_1$–C$_5$ hydrocarbons. The results of the evaluation for the catalysts containing SAPO-5 and SAPO-11 are set forth as weight percents in Tables III and IV. The results in Table III demonstrate that the catalyst containing SAPO-5 gave a 58–67% conversion of ethylbenzene with a 90 to 97% xylene equilibration with a 29 to 33% xylene loss to non-aromatic products. The results in Table IV demonstrate that the catalyst containing SAPO-11 gave a 50–56% conversion of ethylbenzene and converted 97 to 100% of the meta-xylene to ortho- and para-xylene with a 6 to 8% xylene loss to non-aromatic products. The comparative catalyst containing SAPO-5 gave a much higher xylene loss to undesirable products as compared to the catalyst of the present invention.

TABLE III

| (SAPO-5) | | | | |
|---|---|---|---|---|
| Time on Stream (hours) | 22.38 | 48.92 | 73.07 | 93.54 |
| Product Distribution | | | | |
| Benzene | 0.58 | 0.57 | 0.56 | 0.61 |
| Toluene | 6.67 | 4.94 | 5.19 | 5.10 |

TABLE III-continued

| (SAPO-5) | | | | |
|---|---|---|---|---|
| Ethylbenzene | 5.80 | 3.83 | 4.18 | 4.21 |
| P—Xylene | 10.41 | 8.83 | 9.46 | 9.45 |
| M-Xylene | 28.93 | 20.95 | 22.70 | 22.58 |
| O—Xylene | 9.95 | 9.30 | 9.99 | 9.96 |
| 1,2,3 Trimethylbenzene | 0.12 | 0.00 | 0.00 | 0.00 |
| 1,2,4 Trimethylbenzene | 1.36 | 4.75 | 4.69 | 4.76 |
| 1,3,5 Trimethylbenzene | 0.67 | 1.77 | 1.76 | 1.75 |
| M&P Ethyl Toluene[1] | 0.64 | 1.24 | 1.25 | 1.23 |
| O—Ethyl Toluene | 0.07 | 0.19 | 0.19 | 0.19 |
| C$_{10}$—Aromatics | 7.96 | 1.87 | 1.86 | 2.02 |
| Non-Aromatics | 4.70 | 2.76 | 3.03 | 3.00 |
| C$_5^-$ | −2.02 | 14.56 | 10.70 | 10.69 |
| Hydrogen | 24.17 | 24.43 | 24.45 | 24.45 |
| Performance Calculations | | | | |
| Ethylbenzene Conversion | 57.37 | 66.43 | 64.78 | 64.53 |
| Xylene Loss | 29.35 | 33.20 | 30.74 | 31.01 |
| Equilibration (P/PEQ) | 90.26 | 96.57 | 95.92 | 96.15 |
| H$_2$ Consumption | −1.43 | −2.52 | −2.60 | −2.60 |
| X/EB Loss Ratio | 0.51 | 0.50 | 0.47 | 0.48 |
| P/O Xylene Ratio | 1.05 | 0.95 | 0.95 | 0.95 |

[1]M&P Ethyl Toluene = Weight Percent meta- and para- ethyltoluene.
[2]X/EB Loss Ratio.

TABLE IV

| (SAPO-11) | | | | |
|---|---|---|---|---|
| Time on Stream (hours) | 24.63 | 48.48 | 74.43 | 93.78 |
| Product Distribution | | | | |
| Benzene | 0.44 | 0.34 | 0.45 | 0.43 |
| Toluene | 2.30 | 1.91 | 2.17 | 2.01 |
| Ethylbenzene | 6.38 | 6.21 | 6.66 | 6.74 |
| P—Xylene | 13.02 | 13.21 | 13.93 | 14.04 |
| M-Xylene | 31.95 | 30.74 | 32.93 | 31.58 |
| O—Xylene | 13.88 | 13.20 | 14.19 | 14.01 |
| 1,2,3 Trimethylbenzene | 0.00 | 0.00 | 0.00 | 0.00 |
| 1,2,4 Trimethylbenzene | 1.40 | 1.25 | 1.32 | 1.17 |
| 1,3,5 Trimethylbenzene | 0.45 | 0.39 | 0.42 | 0.37 |
| 1,3,5 Trimethylbenzene | 0.45 | 0.39 | 0.42 | 0.32 |
| M&P Ethyl Toluene[1] | 0.40 | 0.36 | 0.39 | 0.35 |
| C$_{10}$—Aromatics | 0.46 | 0.55 | 0.58 | 0.49 |
| Non-Aromatics | 3.89 | 4.12 | 4.21 | 4.03 |
| C$_5^-$ | 2.91 | 5.38 | 0.11 | 1.44 |
| Hydrogen | 21.67 | 22.20 | 22.59 | 22.28 |
| Performance Calculations | | | | |
| Ethylbenzene Conversion | 53.12 | 52.89 | 52.22 | 50.79 |
| Xylene Loss | 7.41 | 8.29 | 7.50 | 6.49 |
| Equilibration (P/PEQ) | 99.03 | 98.65 | 97.53 | 98.95 |
| H$_2$ Consumption | 2.08 | −0.32 | −2.08 | −0.68 |
| X/EB Loss Ratio[2] | 0.14 | 0.16 | 0.14 | 0.13 |
| P/O Xylene Ratio | 1.00 | 0.99 | 0.98 | 1.00 |

[1]M&P Ethyl Toluene = Weight Percent meta- and para- ethyltoluene.
[2]X/EB Loss Ratio =

EXAMPLES 8–20

The procedure employed in Example 6 was employed to evaluate NZMSs, MnAPSO-31 and CoAPSO-31, such being characterized by the adsorption criteria of isobutane and triethylamine characteristic of the NZMSs employed in the process of the instant invention. The MnAPSO-31 NZMSs were prepared according to the disclosure of EPC Publication No. 85104390.1 and the indicated example in the following table. The CoAPSO-31 NZMSs were prepared according to the disclosure of example 101 of EPC Publication No. 85104389.3. The following NZMSs were evaluated as isomerization catalysts:

| Example | NZMS | Prep. Ex. | Post Synthesis Treatment[4] |
|---|---|---|---|
| 8 | MnAPSO-31 | 51 | Calcined in air at 540° C. for 1 hour |
| 9 | MnAPSO-31 | 51 | Calcined in air at 540° C. for 1 hour |
| 10 | MnAPSO-31 | 51 | Calcined 1% O$_2$/99% N$_2$ at 500° C. for 20 hours[5] |

-continued

| Example | NZMS | Prep. Ex. | Post Synthesis Treatment[4] |
|---|---|---|---|
| 11 | MnAPSO-31 | 51 | Calcined in air at 550° C. for 3 hours[6] |
| 12 | MnAPSO-31 | 52 | Calcined in air at 500° C. for 2 hours |
| 13 | MnAPSO-31 | 50[1] | Calcined in air at 500° C. for 2 hours |
| 14 | MnAPSO-31 | 50[2] | Calcined in air at 550° C. for 3 hours[7] |
| 15 | MnAPSO-31 | 50[3] | Calcined in air at 500° C. for 2 hours |
| 16 | MnAPSO-31 | 50 | Calcined in air at 550° C. for 3 hours[8] |
| 17 | CoAPSO-31 | 101 | Calcined in air at 540° C. for 1 hour |
| 18 | CoAPSO-31 | 101 | Calcined in 1% $O_2$/99% $N_2$ at 500° C. for 20 hours[9] |
| 19 | CoAPSO-31 | 101 | Calcined in 1% $O_2$/99% $N_2$ at 500° C. for 20 hours[10] |
| 20 | CoAPSO-31 | 101 | Calcined in air at 550° C. for 3 hours[11] |

[1] Prepared as in Example 50 except the molar amount of MnO was 0.4 instead of 0.2 and the seed was MnAPSO-31.
[2] Prepared by the same procedure employed in Example 13.
[3] Prepared as in Example 50 except the molar amount of MnO was 0.1, instead of 0.4, the seed was MnAPSO-31 and the mixture was heated for 8 hours.
[4] The as-synthesized MnAPSO-31 and CoAPSO-31 were treated by the following procedures to remove organic template or, in the case of regenerated catalysts, to remove catalytic residues from the previous test.
[5] Regeneration of catalyst from Example 8, carried out in reactor.
[6] Regeneration of catalyst from Example 10.
[7] Regeneration of catalyst from Example 13.
[8] Regeneration of catalyst from Example 15.
[9] Regeneration of catalyst from Example 17.
[10] Regeneration of catalyst from Example 18.
[11] Regeneration of catalyst from Example 19.

The above MnAPSO-31 and CoAPSO-31 samples were evaluated according to the procedure employed in Example 6. The results (given on a weight basis for each MnAPSO-31 and CoAFSO-31 of Examples 8 to 20 are set forth in Tables V to XVII, respectively, and are reported on a weight percent basis. The reaction temperature was: 800° F. in Examples 8, 10, 12, 13, 15, 16, 17 and 18; 900° F. in Examples 11, 14, 19 and 20; and 940° F. in Example 9.

TABLE V (Example 8)

| Time on Stream (Minutes) | 90 | 150 | 180 | 210 |
|---|---|---|---|---|
| Benzene | 1.47 | 0.85 | 0.80 | 0.73 |
| Toluene | 1.05 | 0.74 | 0.69 | 1.44 |
| Ethylbenzene | 13.45 | 14.98 | 15.16 | 14.57 |
| P-Xylene | 20.23 | 20.61 | 20.42 | 19.32 |
| M-Xylene | 53.74 | 56.03 | 56.57 | 57.34 |
| O-Xylene | 7.45 | 5.64 | 5.29 | 4.74 |
| 1,2,3 Trimethylbenzene | 0.93 | 0.46 | 0.43 | 0.41 |
| 1,2,4 Trimethylbenzene | 0.29 | 0.27 | 0.24 | 0.26 |
| 1,3,5 Trimethylbenzene | 0.01 | 0.01 | 0.01 | 0.01 |
| M & P Ethyl Toluene | 0.40 | 0.29 | 0.27 | 0.44 |
| O-Ethyl Toluene | 0.01 | 0.01 | 0.01 | 0.02 |
| $C_{10}$-Aromatics | 0.97 | 0.11 | 0.11 | 0.73 |
| M-Xylene Conversion | 34.78 | 31.98 | 31.31 | 30.34 |
| Ethylbenzene Conv. | 24.31 | 15.72 | 14.69 | 17.97 |
| Equilibration (P/PEQ) | 106.23 | 107.08 | 106.09 | 101.47 |
| Total Xylene Loss | 1.19 | 0.11 | 0.10 | 1.11 |
| % M-Xylene Isom. | 96.58 | 99.65 | 99.69 | 96.35 |
| % M Xylene Loss | 3.42 | 0.35 | 0.31 | 3.65 |
| P/(P + O + M) | 24.85 | 25.05 | 24.81 | 23.73 |
| P/O Ratio | 2.72 | 3.65 | 3.86 | 4.07 |
| Wt. % $C_9+$ In Product | 6.70 | 3.44 | 3.28 | 5.58 |

TABLE VI (Example 9)

| Time on Stream (Minutes) | 75 | 105 | 135 | 165 |
|---|---|---|---|---|
| Benzene | 3.83 | 3.22 | 2.79 | 2.53 |
| Toluene | 3.28 | 1.75 | 1.17 | 0.90 |
| Ethylbenzene | 10.03 | 11.21 | 12.23 | 12.69 |
| P-Xylene | 19.97 | 20.61 | 21.09 | 20.72 |
| M-Xylene | 46.41 | 48.96 | 50.45 | 52.17 |
| O-Xylene | 13.35 | 11.88 | 10.52 | 9.62 |
| 1,2,3 Trimethylbenzene | 0.26 | 0.65 | 0.57 | 0.50 |
| 1,2,4 Trimethylbenzene | 0.89 | 0.57 | 0.41 | 0.31 |
| 1,3,5 Trimethylbenzene | 0.08 | 0.06 | 0.05 | 0.04 |
| M & P Ethyl Toluene | 0.70 | 0.38 | 0.25 | 0.19 |

TABLE VI-continued (Example 9)

| | | | | |
|---|---|---|---|---|
| O-Ethyl Toluene | 0.05 | 0.03 | 0.02 | 0.01 |
| $C_{10}$-Aromatics | 1.16 | 0.67 | 0.45 | 0.32 |
| M-Xylene Conversion | 44.39 | 41.15 | 39.27 | 37.15 |
| Ethylbenzene Conv. | 43.80 | 37.00 | 31.16 | 28.51 |
| Equilibration (P/PEQ) | 107.10 | 108.20 | 109.87 | 107.35 |
| Total Xylene Loss | 4.46 | 2.09 | 1.22 | 0.61 |
| % M-Xylene Isom. | 89.95 | 94.92 | 96.88 | 98.37 |
| % M-Xylene Loss | 10.05 | 5.08 | 3.12 | 1.63 |
| P/(P + O + M) | 25.05 | 25.31 | 25.70 | 25.11 |
| P/O Ratio | 1.50 | 1.74 | 2.00 | 2.15 |
| % $C_9+$ In Product | 5.92 | 4.96 | 3.94 | 3.29 |

TABLE VII (Example 10)

| Time on Stream (Minutes) | 60 | 90 | 120 | 150 |
|---|---|---|---|---|
| Benzene | 0.47 | 0.50 | 0.51 | 0.51 |
| Toluene | 0.84 | 0.78 | 0.78 | 0.78 |
| Ethylbenzene | 15.39 | 15.04 | 15.28 | 15.14 |
| P-Xylene | 18.07 | 19.92 | 20.63 | 20.18 |
| M-Xylene | 59.20 | 57.85 | 56.78 | 57.42 |
| O-Xylene | 4.99 | 4.99 | 5.01 | 5.00 |
| 1,2,3 Trimethylbenzene | 0.24 | 0.16 | 0.25 | 0.16 |
| 1,2,4 Trimethylbenzene | 0.20 | 0.19 | 0.19 | 0.19 |
| 1,3,5 Trimethylbenzene | 0.02 | 0.01 | 0.01 | 0.01 |
| M & P Ethyl Toluene | 0.33 | 0.31 | 0.31 | 0.31 |
| O-Ethyl Toluene | 0.01 | 0.01 | 0.01 | 0.01 |
| $C_{10}$-Aromatics | 0.23 | 0.24 | 0.24 | 0.29 |
| M-Xylene Conversion | 28.05 | 29.70 | 30.99 | 30.21 |
| Ethylbenzene Conv. | 13.26 | 15.29 | 13.93 | 14.72 |
| Equilibration (P/PEQ) | 93.89 | 102.91 | 107.03 | 104.46 |
| Total Xylene Loss | 0.02 | −0.57 | −0.17 | −0.39 |
| % M-Xylene Isom. | 99.94 | 101.93 | 100.54 | 101.27 |
| % M-Xylene Loss | 0.06 | −1.93 | −0.54 | −1.27 |
| P/(P + O + M) | 21.96 | 24.07 | 25.03 | 24.43 |
| P/O Ratio | 3.62 | 4.00 | 4.12 | 4.04 |
| % $C_9+$ In Product | 3.48 | 2.90 | 3.10 | 3.01 |

TABLE VIII (Example 11)

| Time on Stream (Minutes) | 80 | 110 | 140 | 170 |
|---|---|---|---|---|
| Benzene | 1.27 | 1.12 | 0.98 | 0.85 |
| Toluene | 1.34 | 0.94 | 0.73 | 0.58 |
| Ethylbenzene | 14.05 | 14.62 | 15.04 | 15.32 |
| P-Xylene | 21.61 | 22.19 | 22.39 | 22.31 |
| M-Xylene | 51.59 | 51.07 | 52.75 | 53.69 |

TABLE VIII-continued (Example 11)

| | | | | |
|---|---|---|---|---|
| O-Xylene | 8.67 | 7.92 | 7.18 | 6.59 |
| 1,2,3 Trimethylbenzene | 0.29 | 0.24 | 0.18 | 0.15 |
| 1,2,4 Trimethylbenzene | 0.45 | 0.36 | 0.29 | 0.24 |
| 1,3,5 Trimethylbenzene | 0.03 | 0.03 | 0.02 | 0.02 |
| M & P Ethyl Toluene | 0.41 | 0.29 | 0.21 | 0.17 |
| O-Ethyl Toluene | 0.02 | 0.02 | 0.01 | 0.01 |
| $C_{10}$-Aromatics | 0.28 | 0.20 | 0.21 | 0.07 |
| M-Xylene Conversion | 37.60 | 36.97 | 36.11 | 34.96 |
| Ethylbenzene Conv. | 20.55 | 17.29 | 14.83 | 13.26 |
| Equilibration (P/PEQ) | 112.85 | 115.44 | 116.28 | 115.50 |
| Total Xylene Loss | 0.98 | 0.53 | 0.30 | −0.05 |
| % M-Xylene Isom. | 97.40 | 98.56 | 99.17 | 100.14 |
| % M-Xylene Loss | 2.60 | 1.44 | 0.83 | −0.14 |
| P/(P + O + M) | 26.40 | 27.00 | 27.20 | 27.01 |
| P/O Ratio | 2.49 | 2.80 | 3.12 | 3.39 |
| Wt. % $C_9+$ In Product | 3.68 | 2.95 | 2.44 | 1.84 |

TABLE IX (Example 12)

| | | | | | |
|---|---|---|---|---|---|
| Time on Stream (Minutes) | 140 | 168 | 210 | 250 | 290 |
| Benzene | 0.00 | 0.00 | 0.00 | 0.00 | 0.00 |
| Toluene | 2.15 | 1.78 | 1.58 | 1.42 | 1.27 |
| Ethylbenzene | 13.94 | 14.41 | 14.72 | 14.97 | 15.19 |
| P-Xylene | 21.76 | 22.54 | 22.75 | 23.00 | 23.12 |
| M-Xylene | 47.44 | 48.27 | 49.07 | 49.85 | 50.39 |
| O-Xylene | 12.56 | 11.20 | 10.32 | 9.55 | 8.91 |
| 1,2,3 Trimethylbenzene | 0.68 | 0.56 | 0.48 | 0.42 | 0.38 |
| 1,2,4 Trimethylbenzene | 0.00 | 0.00 | 0.00 | 0.00 | 0.00 |
| 1,3,5 Trimethylbenzene | 0.08 | 0.06 | 0.05 | 0.05 | 0.04 |
| M & P Ethyl Toluene | 0.74 | 0.62 | 0.55 | 0.50 | 0.47 |
| O-Ethyl Toluene | 0.00 | 0.00 | 0.00 | 0.00 | 0.00 |
| $C_{10}$-Aromatics | 0.65 | 0.56 | 0.47 | 0.23 | 0.24 |
| M-Xylene Conversion | 42.41 | 41.40 | 40.44 | 39.51 | 38.85 |
| Ethylbenzene Conv. | 20.46 | 17.79 | 16.02 | 14.61 | 13.37 |
| Equilibration (P/PEQ) | 113.77 | 117.49 | 118.42 | 119.33 | 119.93 |
| Total Xylene Loss | 0.76 | 0.44 | 0.30 | −0.01 | −0.02 |
| % M-Xylene Isom. | 98.21 | 98.94 | 99.27 | 99.97 | 100.05 |
| % M-Xylene Loss | 1.79 | 1.06 | 0.73 | 0.03 | −0.05 |
| P/(P + O + M) | 26.61 | 27.48 | 27.70 | 27.91 | 28.05 |
| P/O Ratio | 1.73 | 2.01 | 2.20 | 2.41 | 2.59 |
| Wt. % $C_9+$ In Product | 4.77 | 4.11 | 3.69 | 2.94 | 2.82 |

TABLE X (Example 13)

| | | | | |
|---|---|---|---|---|
| Time on Stream (Minutes) | 105 | 135 | 165 | 200 |
| Benzene | 0.34 | 0.27 | 0.23 | 0.20 |
| Toluene | 0.47 | 0.34 | 0.27 | 0.24 |
| Ethylbenzene | 16.19 | 16.40 | 16.59 | 16.69 |
| P-Xylene | 14.22 | 12.54 | 11.44 | 10.85 |
| M-Xylene | 66.08 | 68.12 | 69.41 | 70.14 |
| O-Xylene | 2.30 | 1.99 | 1.77 | 1.66 |
| 1,2,3 Trimethylbenzene | 0.12 | 0.10 | 0.10 | 0.06 |
| 1,2,4 Trimethylbenzene | 0.09 | 0.08 | 0.06 | 0.06 |
| 1,3,5 Trimethylbenzene | 0.02 | 0.02 | 0.02 | 0.02 |
| M & P Ethyl Toluene | 0.13 | 0.09 | 0.06 | 0.05 |
| O-Ethyl Toluene | 0.00 | 0.00 | 0.00 | 0.00 |
| $C_{10}$-Aromatics | 0.05 | 0.05 | 0.04 | 0.03 |
| M-Xylene Conversion | 19.68 | 17.17 | 15.58 | 14.69 |
| Ethylbenzene Conv. | 8.78 | 7.54 | 6.44 | 5.88 |
| Equilibration (P/PEQ) | 73.59 | 64.87 | 59.21 | 56.13 |
| Total Xylene Loss | −0.40 | −0.50 | −0.49 | −0.53 |
| % M-Xylene Isom. | 102.01 | 102.92 | 103.15 | 103.57 |
| % M Xylene Loss | −2.01 | −2.92 | −3.15 | −3.57 |
| P/(P + O + M) | 17.21 | 15.17 | 13.85 | 13.13 |
| P/O Ratio | 6.18 | 6.30 | 6.46 | 6.54 |
| Wt. % $C_9+$ In Product | 2.00 | 1.90 | 1.73 | 1.45 |

TABLE XI (Example 14)

| | | | | | |
|---|---|---|---|---|---|
| Time on Stream (Minutes) | 75 | 105 | 135 | 165 | 205 |
| Benzene | 0.80 | 0.66 | 0.47 | 0.35 | 0.27 |
| Toluene | 0.76 | 0.58 | 0.41 | 0.32 | 0.26 |
| Ethylbenzene | 15.30 | 15.62 | 16.07 | 16.38 | 16.56 |
| P-Xylene | 15.38 | 14.74 | 12.99 | 11.72 | 10.63 |
| M-Xylene | 63.83 | 64.80 | 67.07 | 68.61 | 69.97 |
| O-Xylene | 3.19 | 3.02 | 2.62 | 2.34 | 2.08 |
| 1,2,3 Trimethylbenzene | 0.14 | 0.11 | 0.04 | 0.05 | 0.04 |
| 1,2,4 Trimethylbenzene | 0.19 | 0.16 | 0.12 | 0.10 | 0.08 |
| 1,3,5 Trimethylbenzene | 0.04 | 0.04 | 0.03 | 0.03 | 0.02 |
| M & P Ethyl Toluene | 0.21 | 0.15 | 0.10 | 0.07 | 0.05 |
| O-Ethyl Toluene | 0.01 | 0.01 | 0.00 | 0.00 | 0.01 |
| $C_{10}$-Aromatics | 0.14 | 0.11 | 0.08 | 0.03 | 0.03 |
| M-Xylene Conversion | 22.67 | 21.46 | 18.65 | 16.74 | 15.07 |
| Ethylbenzene Conv. | 13.34 | 11.47 | 8.87 | 7.08 | 6.00 |
| Equilibration (P/PEQ) | 79.80 | 76.33 | 67.16 | 60.59 | 54.96 |
| Total Xylene Loss | 0.17 | −0.07 | −0.28 | −0.32 | −0.35 |
| % M-Xylene Isom. | 99.25 | 100.32 | 101.52 | 101.88 | 102.34 |
| % M-Xylene Loss | 0.75 | −0.32 | −1.52 | −1.88 | −2.34 |
| P/(P + O + M) | 18.66 | 17.85 | 15.71 | 14.17 | 12.86 |
| P/O Ratio | 4.82 | 4.88 | 4.95 | 5.00 | 5.11 |
| Wt. % $C_9+$ In Product | 2.99 | 2.53 | 1.88 | 1.62 | 1.48 |

TABLE XII (Example 15)

| | | | | | |
|---|---|---|---|---|---|
| Time on Stream (Minutes) | 90 | 150 | 180 | 225 | 270 |
| Benzene | 0.60 | 0.57 | 0.53 | 0.50 | 0.47 |
| Toluene | 1.11 | 0.64 | 0.45 | 0.39 | 0.35 |
| Ethylbenzene | 14.65 | 15.26 | 15.54 | 15.70 | 15.82 |
| P-Xylene | 22.67 | 22.52 | 22.19 | 21.78 | 21.29 |
| M-Xylene | 54.78 | 55.96 | 56.84 | 57.54 | 58.32 |
| O-Xylene | 4.99 | 4.25 | 3.81 | 3.50 | 3.23 |
| 1,2,3 Trimethylbenzene | 0.32 | 0.28 | 0.25 | 0.23 | 0.20 |
| 1,2,4 Trimethylbenzene | 0.22 | 0.18 | 0.16 | 0.14 | 0.12 |
| 1,3,5 Trimethylbenzene | 0.00 | 0.00 | 0.00 | 0.00 | 0.00 |
| M & P Ethyl Toluene | 0.49 | 0.31 | 0.22 | 0.19 | 0.17 |
| O-Ethyl Toluene | 0.01 | 0.00 | 0.00 | 0.00 | 0.00 |
| $C_{10}$-Aromatics | 0.16 | 0.04 | 0.01 | 0.02 | 0.02 |
| M-Xylene Conversion | 33.59 | 32.14 | 31.06 | 30.20 | 29.24 |
| Ethylbenzene Conv. | 16.98 | 13.49 | 11.87 | 10.96 | 10.27 |
| Equilibration (P/PEQ) | 117.57 | 116.38 | 114.50 | 112.44 | 109.88 |
| Total Xylene Loss | 0.06 | −0.31 | −0.47 | −0.48 | −0.51 |
| % M-Xylene Isom. | 99.83 | 100.96 | 101.52 | 101.58 | 101.74 |
| % M-Xylene Loss | 0.17 | −0.96 | −1.52 | −1.58 | −1.74 |
| P/(P + O + M) | 27.50 | 27.22 | 26.78 | 26.30 | 25.70 |
| P/O Ratio | 4.54 | 5.30 | 5.82 | 6.22 | 6.59 |
| Wt. % $C_9+$ In Product | 3.40 | 2.46 | 2.03 | 1.90 | 1.73 |

TABLE XIII (Example 16)

| | | | | | |
|---|---|---|---|---|---|
| Time on Stream (Minutes) | 105 | 135 | 165 | 195 | 245 |
| Benzene | 0.30 | 0.30 | 0.28 | 0.26 | 0.24 |
| Toluene | 0.48 | 0.30 | 0.21 | 0.17 | 0.15 |
| Ethylbenzene | 15.71 | 16.07 | 16.21 | 16.31 | 16.39 |
| P-Xylene | 18.90 | 17.79 | 16.87 | 16.05 | 15.27 |
| M-Xylene | 61.21 | 62.93 | 64.03 | 65.09 | 66.00 |
| O-Xylene | 2.79 | 2.21 | 2.04 | 1.90 | 1.76 |
| 1,2,3 Trimethylbenzene | 0.14 | 0.12 | 0.10 | 0.05 | 0.08 |
| 1,2,4 Trimethylbenzene | 0.10 | 0.07 | 0.06 | 0.05 | 0.04 |
| 1,3,5 Trimethylbenzene | 0.00 | 0.00 | 0.00 | 0.00 | 0.00 |
| M & P Ethyl Toluene | 0.19 | 0.14 | 0.10 | 0.08 | 0.07 |
| O-Ethyl Toluene | 0.00 | 0.00 | 0.00 | 0.00 | 0.00 |
| $C_{10}$-Aromatics | 0.18 | 0.07 | 0.09 | 0.04 | 0.01 |
| M-Xylene Conversion | 25.69 | 23.62 | 22.26 | 20.98 | 19.87 |
| Ethylbenzene Conv. | 10.83 | 8.80 | 7.97 | 7.41 | 6.96 |

TABLE XIII-continued
(Example 16)

| | | | | | |
|---|---|---|---|---|---|
| Equilibration (P/PEQ) | 97.46 | 91.72 | 86.96 | 82.64 | 78.62 |
| Total Xylene Loss | 0.64 | −0.67 | −0.71 | −0.81 | −0.80 |
| % M-Xylene Isom. | 102.47 | 102.83 | 103.18 | 103.86 | 104.04 |
| % M-Xylene Loss | −2.47 | −2.83 | −3.18 | −3.86 | −4.04 |
| P/(P + O + M) | 22.80 | 21.45 | 20.34 | 19.33 | 18.39 |
| P/O Ratio | 6.78 | 8.04 | 8.26 | 8.44 | 8.67 |
| Wt. % $C_9+$ In Product | 2.26 | 1.65 | 1.52 | 1.02 | 0.95 |

TABLE XIV
(Example 17)

| Time on Stream (Minutes) | 80 | 130 | 165 | 195 |
|---|---|---|---|---|
| Benzene | 0.69 | 0.51 | 0.37 | 0.29 |
| Toluene | 1.63 | 0.79 | 0.42 | 0.30 |
| Ethylbenzene | 14.19 | 15.45 | 16.08 | 16.33 |
| P-Xylene | 19.83 | 18.76 | 17.31 | 16.26 |
| M-Xylene | 57.35 | 60.91 | 63.04 | 64.46 |
| O-Xylene | 4.00 | 2.93 | 2.39 | 2.09 |
| 1,2,3 Trimethylbenzene | 1.23 | 0.21 | 0.14 | 0.10 |
| 1,2,4 Trimethylbenzene | 0.23 | 0.13 | 0.09 | 0.07 |
| 1,3,5 Trimethylbenzene | 0.01 | 0.00 | 0.00 | 0.00 |
| M & P Ethyl Toluene | 0.57 | 0.28 | 0.14 | 0.10 |
| O-Ethyl Toluene | 0.01 | 0.00 | 0.00 | 0.00 |
| $C_{10}$-Aromatics | 0.25 | 0.03 | 0.01 | 0.00 |
| M-Xylene Conversion | 30.33 | 26.03 | 23.38 | 21.62 |
| Ethylbenzene Conv. | 20.11 | 13.00 | 9.38 | 7.96 |
| Equilibration (P/PEQ) | 104.43 | 97.09 | 89.46 | 83.94 |
| Total Xylene Loss | 1.38 | −0.32 | −0.57 | −0.68 |
| % M-Xylene Isom. | 95.45 | 101.21 | 102.45 | 103.17 |
| % M-Xylene Loss | 4.55 | −1.21 | −2.45 | −3.17 |
| P/(P + O + M) | 24.43 | 22.71 | 20.92 | 19.63 |
| P/O Ratio | 4.96 | 6.39 | 7.24 | 7.78 |
| Wt. % $C_9+$ In Product | 7.02 | 2.40 | 1.59 | 1.23 |

TABLE XV
(Example 18)

| Time on Stream (Minutes) | 100 | 155 | 200 | 260 | 305 |
|---|---|---|---|---|---|
| Benzene | 0.60 | 0.45 | 0.34 | 0.26 | 0.22 |
| Toluene | 1.01 | 0.52 | 0.33 | 0.25 | 0.20 |
| Ethylbenzene | 14.97 | 15.80 | 16.19 | 16.39 | 16.51 |
| P-Xylene | 20.32 | 19.38 | 18.07 | 16.76 | 15.42 |
| M-Xylene | 58.72 | 60.56 | 62.41 | 64.11 | 65.70 |
| O-Xylene | 3.35 | 2.75 | 2.34 | 2.01 | 1.78 |
| 1,2,3 Trimethylbenzene | 0.29 | 0.19 | 0.12 | 0.09 | 0.07 |
| 1,2,4 Trimethylbenzene | 0.16 | 0.11 | 0.08 | 0.06 | 0.05 |
| 1,3,5 Trimethylbenzene | 0.00 | 0.00 | 0.00 | 0.00 | 0.00 |
| M & P Ethyl Toluene | 0.42 | 0.21 | 0.12 | 0.07 | 0.06 |
| O-Ethyl Toluene | 0.00 | 0.00 | 0.00 | 0.00 | 0.00 |
| $C_{10}$-Aromatics | 0.16 | 0.03 | 0.00 | 0.00 | 0.00 |
| M-Xylene Conversion | 28.69 | 26.42 | 24.13 | 22.04 | 20.10 |
| Ethylbenzene Conv. | 15.74 | 10.99 | 8.77 | 7.61 | 6.93 |
| Equilibration (P/PEQ) | 105.47 | 100.21 | 93.27 | 86.45 | 79.51 |
| Total Xylene Loss | −0.06 | −0.48 | −0.68 | −0.78 | −0.81 |
| % M-Xylene Isom. | 100.20 | 101.82 | 102.82 | 103.55 | 104.05 |
| % M-Xylene Loss | −0.20 | −1.82 | −2.82 | −3.55 | −4.05 |
| P/(P + O + M) | 24.67 | 23.44 | 21.82 | 20.22 | 18.60 |
| P/O Ratio | 6.07 | 7.04 | 7.72 | 8.33 | 8.66 |
| Wt. % $C_9+$ In Product | 3.38 | 1.99 | 1.31 | 0.99 | 0.89 |

TABLE XVI
(Example 19)

| Time on Stream (Minutes) | 140 | 170 | 200 | 230 |
|---|---|---|---|---|
| Benzene | 0.63 | 0.44 | 0.30 | 0.22 |
| Toluene | 0.97 | 0.67 | 0.46 | 0.35 |

TABLE XVI-continued
(Example 19)

| | | | | |
|---|---|---|---|---|
| Ethylbenzene | 15.43 | 15.93 | 16.29 | 16.51 |
| P-Xylene | 18.98 | 17.00 | 14.23 | 11.50 |
| M-Xylene | 59.27 | 62.43 | 66.22 | 69.56 |
| O-Xylene | 3.98 | 3.00 | 2.14 | 1.57 |
| 1,2,3 Trimethylbenzene | 0.11 | 0.07 | 0.05 | 0.04 |
| 1,2,4 Trimethylbenzene | 0.30 | 0.22 | 0.15 | 0.12 |
| 1,3,5 Trimethylbenzene | 0.05 | 0.05 | 0.04 | 0.04 |
| M & P Ethyl Toluene | 0.21 | 0.14 | 0.08 | 0.06 |
| O-Ethyl Toluene | 0.01 | 0.00 | 0.00 | 0.00 |
| $C_{10}$-Aromatics | 0.06 | 0.05 | 0.04 | 0.03 |
| M-Xylene Conversion | 28.19 | 24.29 | 19.65 | 15.56 |
| Ethylbenzene Conv. | 12.58 | 9.69 | 7.57 | 6.27 |
| Equilibration (P/PEQ) | 98.71 | 88.17 | 73.66 | 59.48 |
| Total Xylene Loss | 0.37 | 0.03 | −0.22 | −0.30 |
| % M-Xylene Isom. | 98.70 | 99.87 | 101.12 | 101.95 |
| % M-Xylene Loss | 1.30 | 0.13 | −1.12 | −1.95 |
| P/(P + O + M) | 23.09 | 20.62 | 17.23 | 13.91 |
| P/O Ratio | 4.78 | 5.66 | 6.64 | 7.31 |
| Wt. % $C_9+$ In Product | 2.54 | 2.13 | 1.79 | 1.81 |

TABLE XVII
(Example 20)

| Time on Stream (Minutes) | 75 | 105 | 145 | 180 | 210 |
|---|---|---|---|---|---|
| Benzene | 0.59 | 0.43 | 0.43 | 0.19 | 0.15 |
| Toluene | 0.75 | 0.50 | 0.50 | 0.22 | 0.18 |
| Ethylbenzene | 15.39 | 15.91 | 15.91 | 16.62 | 16.69 |
| P-Xylene | 17.55 | 15.68 | 15.68 | 10.06 | 8.03 |
| M-Xylene | 61.44 | 64.23 | 64.23 | 71.37 | 73.51 |
| O-Xylene | 3.61 | 2.85 | 2.85 | 1.39 | 1.06 |
| 1,2,3 Trimethylbenzene | 0.10 | 0.06 | 0.06 | 0.02 | 0.01 |
| 1,2,4 Trimethylbenzene | 0.21 | 0.15 | 0.15 | 0.07 | 0.05 |
| 1,3,5 Trimethylbenzene | 0.02 | 0.02 | 0.02 | 0.02 | 0.01 |
| M & P Ethyl Toluene | 0.22 | 0.12 | 0.12 | 0.04 | 0.03 |
| O-Ethyl Toluene | 0.01 | 0.00 | 0.00 | 0.00 | 0.00 |
| $C_{10}$-Aromatics | 0.11 | 0.05 | 0.05 | 0.00 | 0.28 |
| M-Xylene Conversion | 25.52 | 22.09 | 22.09 | 13.35 | 10.69 |
| Ethylbenzene Conv. | 12.75 | 9.77 | 9.77 | 5.68 | 5.21 |
| Equilibration (P/PEQ) | 90.84 | 81.00 | 81.00 | 51.91 | 41.58 |
| Total Xylene Loss | −0.12 | −0.38 | −0.38 | −0.55 | −0.36 |
| % M-Xylene Isom. | 100.47 | 101.72 | 101.72 | 104.15 | 103.36 |
| % M-Xylene Loss | −0.47 | −1.72 | −1.72 | −4.15 | −3.36 |
| P/(P + O + M) | 21.25 | 18.95 | 18.95 | 12.14 | 9.72 |
| P/O Ratio | 4.87 | 5.51 | 5.51 | 7.22 | 7.57 |
| Wt. % $C_9+$ In Product | 2.49 | 1.74 | 1.74 | 1.10 | 3.16 |

Figure 2:
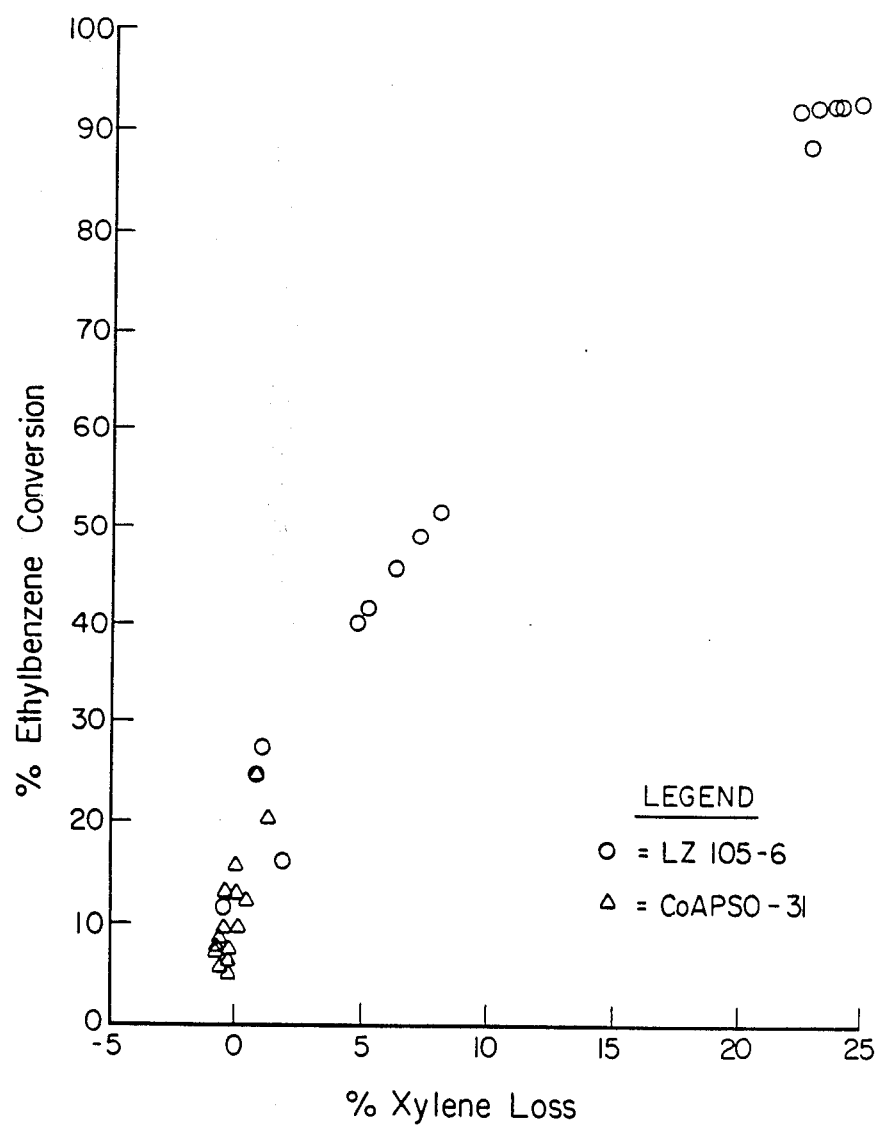
FIG. 2 is a plot of wt. % ethylbenzene conversion vs. wt. % xylene loss for LZ-105 and CoAPSO-31.
Figure 3:
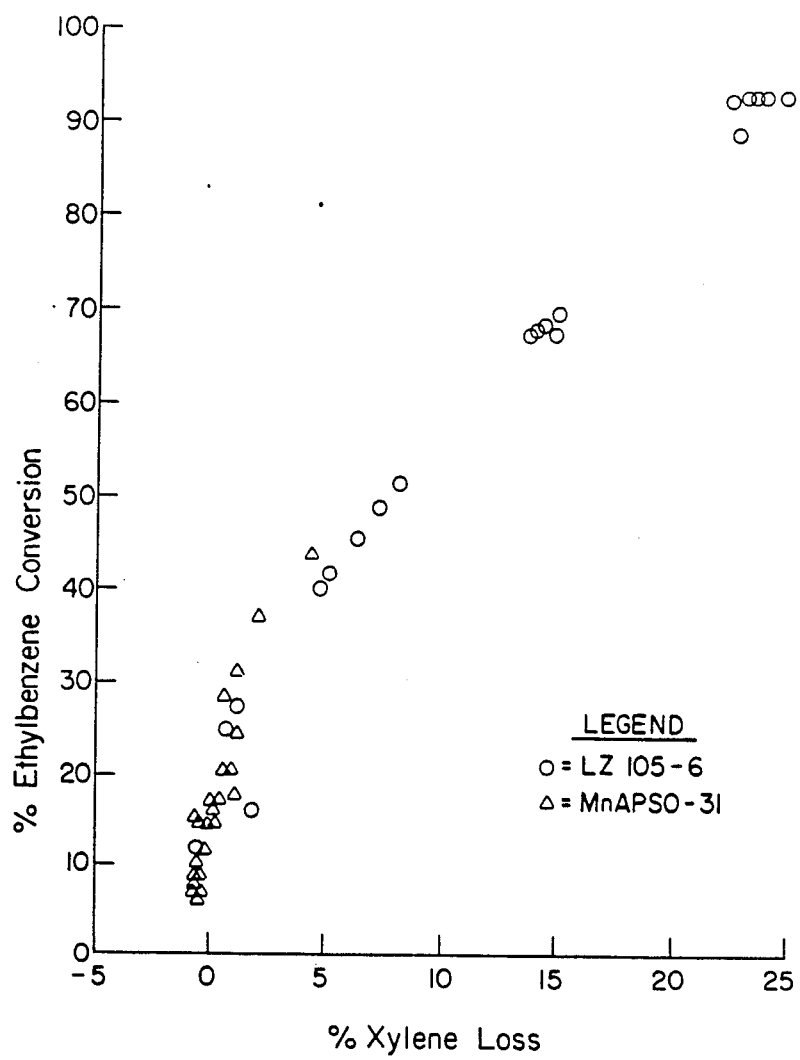
FIG. 3 is a plot of wt. % ethylbenzene conversion vs. wt. % xylene loss of LZ-105 and MnAPSO-31.

A comparison of MnAPSO-31 and CoAPSO-31 with the LZ-105 of comparative examples B-F are depicted in FIGS. 2 and 3. The activity and selectivity of MnAPSO-11 and CoAPSO-11 over LZ-105 is shown. Further, Comparative example A demonstrates that it is the novel compositions of this invention and not simply the chemical mixture that is important.

EXAMPLES 21, 22 and 23

The procedure employed in Examples 8–20 was employed to evaluate three samples of NZMSs characterized by the adsorption criteria for isobutane and triethylamine characteristic of NZMSs employed in the process of the instant process. The two NZMS samples are denominated CoAPSO-11 and MnAPSO-11 and were prepared according to the procedures disclosed in the EPC applications noted in Examples 8–20 and the MnAPO was prepared according to U.S. Pat. No. 4,567,029. The as-synthesized samples were treated as follows prior to evaluation at a reaction temperature of 800° F.:

| Example | NZMS | Prep. Ex. | Post Synthesis Treatment |
|---|---|---|---|
| 21 | MnAPSO-11 | 25 | Calcined in air at 500° C. for 2 hours |
| 22 | MnAPO-11 | 72[1] | Calcined in air[2] |
| 23 | CoAPSO-11 | 60 | Calcined in air at 600° C. for 1.5 hours |
| A | Co, Al, P, Si, O | I[3] | Calcined in air at 600° C. for 1 hour |

[1] Prepared according to example 72 of U.S. Pat. No. 4,567,029
[2] Calcined in air at 100–500° C., increased to 500° C. over a four hour period; calcined in air at 500° C. for 24 hours; and then calcined in air at 550° C. for 51 hours.
[3] Example I of EPC Application No. 85104389.3

MnAPSO-11, MnAPO-11, CoAPSO-11 and Example A were evaluated and the results are reported (on a weight basis) in Tables XVIII to XXI.

TABLE XVIII
(Example 21)

| Time on Stream (Minutes) | 80 | 115 | 145 | 185 |
|---|---|---|---|---|
| Benzene | 0.68 | 0.48 | 0.38 | 0.36 |
| Toluene | 2.88 | 1.48 | 0.98 | 0.84 |
| Ethylbenzene | 14.02 | 15.29 | 15.72 | 15.90 |
| P-Xylene | 18.77 | 19.25 | 18.82 | 18.53 |
| M-Xylene | 44.61 | 47.71 | 50.01 | 51.10 |
| O-Xylene | 15.43 | 14.03 | 12.95 | 12.29 |
| 1,2,3 Trimethylbenzene | 0.39 | 0.24 | 0.18 | 0.16 |
| 1,2,4 Trimethylbenzene | 0.97 | 0.48 | 0.33 | 0.28 |
| 1,3,5 Trimethylbenzene | 0.16 | 0.08 | 0.06 | 0.05 |
| M & P Ethyl Toluene | 0.84 | 0.43 | 0.28 | 0.24 |
| O-Ethyl Toluene | 0.10 | 0.05 | 0.03 | 0.03 |
| $C_{10}$-Aromatics | 1.14 | 0.48 | 0.26 | 0.22 |
| M-Xylene Conversion | 45.79 | 42.01 | 39.21 | 37.87 |
| Ethylbenzene Conv. | 21.01 | 13.87 | 11.38 | 10.38 |
| Equilibration (P/PEQ) | 101.84 | 101.64 | 98.38 | 96.71 |
| Total Xylene Loss | 4.22 | 1.56 | 0.59 | 0.40 |
| % M-Xylene Isom. | 90.78 | 96.28 | 98.50 | 98.93 |
| % M-Xylene Loss | 9.22 | 3.72 | 1.50 | 1.07 |
| P/(P + O + M) | 23.82 | 23.77 | 23.01 | 22.62 |
| P/O Ratio | 1.22 | 1.37 | 1.45 | 1.51 |
| Wt. % $C_9+$ In Product | 7.42 | 4.07 | 2.86 | 2.55 |

TABLE XIX
(Example 22)

| Time on Stream (Minutes) | 110 | 150 | 180 | 215 | 245 |
|---|---|---|---|---|---|
| Benzene | 0.11 | 0.10 | 0.09 | 0.08 | 0.08 |
| Toluene | 0.36 | 0.28 | 0.24 | 0.21 | 0.20 |
| Ethylbenzene | 16.46 | 16.63 | 16.72 | 16.77 | 16.83 |
| P-Xylene | 16.60 | 15.95 | 14.98 | 14.32 | 13.91 |
| M-Xylene | 58.28 | 59.84 | 61.46 | 62.64 | 63.32 |
| O-Xylene | 7.80 | 6.90 | 6.29 | 5.81 | 5.48 |
| 1,2,3 Trimethylbenzene | 0.05 | 0.04 | 0.04 | 0.03 | 0.03 |
| 1,2,4 Trimethylbenzene | 0.09 | 0.07 | 0.06 | 0.05 | 0.05 |
| 1,3,5 Trimethylbenzene | 0.00 | 0.00 | 0.00 | 0.00 | 0.00 |
| M & P Ethyl Toluene | 0.14 | 0.12 | 0.10 | 0.08 | 0.08 |
| O-Ethyl Toluene | 0.00 | 0.00 | 0.00 | 0.00 | 0.00 |
| $C_{10}$-Aromatics | 0.11 | 0.07 | 0.02 | 0.01 | 0.01 |
| M-Xylene Conversion | 29.08 | 27.19 | 25.22 | 23.78 | 22.95 |
| Ethylbenzene Conv. | 7.14 | 6.19 | 5.69 | 5.41 | 5.04 |
| Equilibration (P/PEQ) | 85.85 | 82.46 | 77.40 | 73.95 | 71.91 |
| Total Xylene Loss | −0.60 | −0.62 | −0.66 | −0.72 | −0.65 |
| % M-Xylene Isom. | 102.07 | 102.27 | 102.64 | 103.01 | 102.83 |
| % M-Xylene Loss | −2.07 | −2.27 | −2.64 | −3.01 | −2.83 |
| P/(P + O + M) | 20.08 | 19.29 | 18.10 | 17.30 | 16.82 |
| P/O Ratio | 2.13 | 2.31 | 2.38 | 2.46 | 2.54 |
| Wt. % $C_9+$ In Product | 1.32 | 1.10 | 0.88 | 0.72 | 0.75 |

TABLE XX
(Example 23)

| Time on Stream (Minutes) | 75 | 100 | 125 | 150 |
|---|---|---|---|---|
| Benzene | 0.76 | 0.78 | 0.71 | 0.67 |
| Toluene | 3.28 | 3.26 | 2.98 | 2.76 |
| Ethylbenzene | 14.50 | 14.43 | 14.72 | 14.94 |
| P-Xylene | 9.83 | 9.02 | 8.85 | 8.59 |
| M-Xylene | 62.01 | 63.43 | 64.27 | 65.12 |
| O-Xylene | 5.70 | 5.17 | 4.89 | 4.62 |
| 1,2,3 Trimethylbenzene | 0.45 | 0.33 | 0.42 | 0.39 |
| 1,2,4 Trimethylbenzene | 1.60 | 1.59 | 1.46 | 1.33 |
| 1,3,5 Trimethylbenzene | 0.21 | 0.21 | 0.19 | 0.18 |
| M & P Ethyl Toluene | 0.83 | 0.82 | 0.76 | 0.69 |
| O-Ethyl Toluene | 0.08 | 0.08 | 0.07 | 0.07 |
| $C_{10}$-Aromatics | 0.75 | 0.87 | 0.68 | 0.63 |
| M-Xylene Conversion | 24.71 | 22.97 | 21.95 | 20.90 |
| Ethylbenzene Conv. | 18.36 | 18.76 | 17.13 | 15.85 |
| Equilibration (P/PEQ) | 54.20 | 49.66 | 48.48 | 46.90 |
| Total Xylene Loss | 5.86 | 5.74 | 5.26 | 4.85 |
| % M-Xylene Isom. | 76.30 | 75.02 | 76.03 | 76.78 |
| % M-Xylene Loss | 23.70 | 24.98 | 23.97 | 23.22 |
| P/(P + O + M) | 12.68 | 11.62 | 11.34 | 10.97 |
| P/O Ratio | 1.73 | 1.74 | 1.81 | 1.86 |
| Wt. % $C_9+$ In Product | 14.31 | 15.05 | 14.60 | 14.14 |

TABLE XXI
(Example A)

| Time on Stream (Minutes) | 165 | 205 |
|---|---|---|
| Benzene | 0.03 | 0.03 |
| Toluene | 0.14 | 0.13 |
| Ethylbenzene | 17.30 | 17.42 |
| P-Xylene | 1.09 | 0.00 |
| M-Xylene | 80.75 | 82.19 |
| O-Xylene | 0.61 | 0.17 |
| 1,2,3 Trimethylbenzene | 0.00 | 0.00 |
| 1,2,4 Trimethylbenzene | 0.04 | 0.04 |
| 1,3,5 Trimethylbenzene | 0.01 | 0.01 |
| M & P Ethyl Toluene | 0.02 | 0.01 |
| O-Ethyl Toluene | 0.00 | 0.00 |
| $C_{10}$-Aromatics | 0.01 | 0.00 |
| M-Xylene Conversion | 1.73 | −0.03 |
| Ethylbenzene Conv. | 2.39 | 1.74 |
| Equilibration (P/PEQ) | 5.66 | 0.00 |
| Total Xylene Loss | −0.34 | −0.24 |
| % M-Xylene Isom. | 119.76 | — |
| % M-Xylene Loss | −19.76 | 796.80 |
| P/(P + O + M) | 1.32 | 0.00 |
| P/O Ratio | 1.79 | 0.00 |
| Wt. % $C_9+$ In Product | 3.54 | 12.82 |

COMPARATIVE EXAMPLES B to F

LZ-105 (a zeolite having the pentasil structure) was prepared according to example 8 of U.S. Pat. No. 4,257,885. The LZ-105 product was washed with an acid solution (1.1 molar HCl) at 100° C. for 1 hour and then water washed until substantially all Cl⁻ was removed and dried at 100° C. in air. The final acid washed LZ-105 Examples B, E and F had a $SiO_2/Al_2O_3$ of 35.9 and the acid washed LZ-105 of Examples C and D had a $SiO_2/Al_2O_3$ of 40.0.

The five LZ-105 samples were evaluated according to the procedure described in Examples 8 to 20. The samples were evaluated at the following temperatures:

| Comparative Example | Evaluation Temperature (°F.) |
|---|---|
| B | 550 |
| C | 600 |
| D | 650 |
| E | 700 |

| Comparative Example | Evaluation Temperature (°F.) |
|---|---|
| F | 800 |

The results (given on a weight basis) of the evaluation of the LZ-105 samples (LZ-105 is characterized by the isobutane/triethylamine adsorption of the instant invention but is not a NZMS) are set forth in Tables XXII to XXVI.

TABLE XXII (Example B)

| | | | |
|---|---|---|---|
| Time on Stream (Minutes) | 105 | 135 | 160 |
| Benzene | 1.00 | 0.51 | 0.47 |
| Toluene | 1.73 | 0.37 | 0.34 |
| Ethylbenzene | 14.95 | 15.66 | 15.70 |
| P-Xylene | 18.57 | 19.02 | 18.69 |
| M-Xylene | 50.99 | 52.52 | 52.94 |
| O-Xylene | 11.40 | 11.07 | 10.96 |
| 1,2,3 Trimethylbenzene | 0.46 | 0.42 | 0.44 |
| 1,2,4 Trimethylbenzene | 0.05 | 0.05 | 0.06 |
| 1,3,5 Trimethylbenzene | 0.05 | 0.00 | 0.00 |
| M & P Ethyl Toluene | 0.31 | 0.10 | 0.10 |
| O-Ethyl Toluene | 0.14 | 0.00 | 0.00 |
| $C_{10}$-Aromatics | 0.35 | 0.28 | 0.30 |
| M-Xylene Conversion | 38.20 | 36.15 | 35.61 |
| Ethylbenzene Conv. | 15.99 | 11.72 | 11.49 |
| Equilibration (P/PEQ) | 98.08 | 98.45 | 96.74 |
| Total Xylene Loss | 1.88 | −0.44 | −0.45 |
| % M-Xylene Isom. | 95.09 | 101.22 | 101.26 |
| % M-Xylene Loss | 4.91 | −1.22 | −1.26 |
| P/(P + O + M) | 22.94 | 23.03 | 22.63 |
| P/O Ratio | 1.63 | 1.72 | 1.71 |
| Wt. % $C_9+$ In Product | 3.39 | 2.27 | 2.44 |

TABLE XXIII (Example C)

| | | | | | |
|---|---|---|---|---|---|
| Time on Stream (Minutes) | 110 | 140 | 170 | 200 | 230 |
| Benzene | 1.43 | 1.39 | 1.42 | 1.45 | 1.47 |
| Toluene | 1.52 | 1.19 | 1.08 | 1.06 | 1.06 |
| Ethylbenzene | 12.84 | 13.32 | 13.35 | 13.31 | 13.31 |
| P-Xylene | 19.22 | 19.50 | 19.44 | 19.47 | 19.46 |
| M-Xylene | 46.64 | 46.44 | 46.55 | 46.50 | 46.42 |
| O-Xylene | 15.90 | 15.90 | 15.91 | 15.97 | 15.97 |
| 1,2,3 Trimethylbenzene | 0.77 | 0.82 | 0.85 | 0.87 | 0.88 |
| 1,2,4 Trimethylbenzene | 0.24 | 0.18 | 0.17 | 0.17 | 0.17 |
| 1,3,5 Trimethylbenzene | 0.04 | 0.00 | 0.00 | 0.00 | 0.00 |
| M & P Ethyl Toluene | 0.36 | 0.30 | 0.28 | 0.28 | 0.28 |
| O-Ethyl Toluene | 0.03 | 0.01 | 0.01 | 0.01 | 0.01 |
| $C_{10}$-Aromatics | 1.00 | 0.95 | 0.94 | 0.90 | 0.97 |
| M-Xylene Conversion | 43.54 | 43.76 | 43.62 | 43.69 | 43.78 |
| Ethylbenzene Conv. | 27.31 | 24.55 | 24.40 | 24.64 | 24.65 |
| Equilibration (P/PEQ) | 100.50 | 101.88 | 101.46 | 101.60 | 101.64 |
| Total Xylene Loss | 1.02 | 0.89 | 0.81 | 0.76 | 0.87 |
| % M-Xylene Isom. | 97.65 | 97.96 | 98.14 | 98.26 | 98.01 |
| % M-Xylene Loss | 2.35 | 2.04 | 1.86 | 1.74 | 1.99 |
| P/P + O + M) | 23.51 | 23.83 | 23.73 | 23.76 | 23.77 |
| P/O Ratio | 1.21 | 1.23 | 1.22 | 1.22 | 1.22 |
| Wt. % $C_9+$ In Product | 5.06 | 4.71 | 4.71 | 4.66 | 4.81 |

TABLE XXIV (Example D)

| | | | | | |
|---|---|---|---|---|---|
| Time on Stream (Minutes) | 90 | 110 | 140 | 170 | 200 |
| Benzene | 3.44 | 3.36 | 3.12 | 2.81 | 2.68 |
| Toluene | 4.77 | 4.57 | 4.05 | 3.49 | 3.25 |
| Ethylbenzene | 8.66 | 9.11 | 9.70 | 10.37 | 10.67 |
| P-Xylene | 17.36 | 17.66 | 17.75 | 17.72 | 17.71 |
| M-Xylene | 43.53 | 44.12 | 44.95 | 46.16 | 46.63 |
| O-Xylene | 15.43 | 15.31 | 15.13 | 14.78 | 14.63 |
| 1,2,3 Trimethylbenzene | 0.96 | 0.92 | 0.90 | 0.87 | 0.87 |
| 1,2,4 Trimethylbenzene | 1.07 | 1.05 | 0.90 | 0.74 | 0.68 |
| 1,3,5 Trimethylbenzene | 0.04 | 0.04 | 0.03 | 0.02 | 0.02 |
| M & P Ethyl Toluene | 1.23 | 1.14 | 1.00 | 0.86 | 0.80 |
| O-Ethyl Toluene | 0.11 | 0.10 | 0.09 | 0.08 | 0.07 |
| $C_{10}$-Aromatics | 3.40 | 2.61 | 2.39 | 2.09 | 1.99 |
| M-Xylene Conversion | 47.55 | 46.91 | 45.87 | 44.36 | 43.76 |
| Ethylbenzene Conv. | 51.23 | 48.72 | 45.41 | 41.53 | 39.83 |
| Equilibration (P/PEQ) | 97.23 | 97.93 | 97.49 | 96.31 | 95.90 |
| Total Xylene Loss | 8.05 | 7.24 | 6.28 | 5.18 | 4.76 |
| % M-Xylene Isom. | 83.08 | 84.58 | 86.32 | 88.33 | 89.12 |
| % M-Xylene Loss | 16.92 | 15.42 | 13.68 | 11.67 | 10.88 |
| P/(P + O + M) | 22.74 | 22.91 | 22.80 | 22.53 | 22.43 |
| P/O Ratio | 1.12 | 1.15 | 1.17 | 1.20 | 1.21 |
| Wt. % $C_9+$ In Product | 11.73 | 10.35 | 9.67 | 8.88 | 8.60 |

TABLE XXV (Example E)

| | | | | | |
|---|---|---|---|---|---|
| Time on Stream (Minutes) | 80 | 110 | 140 | 170 | 200 |
| Benzene | 5.19 | 5.34 | 5.21 | 5.18 | 5.17 |
| Toluene | 8.26 | 8.32 | 8.01 | 7.80 | 7.68 |
| Ethylbenzene | 5.72 | 5.36 | 5.53 | 5.62 | 5.72 |
| P-Xylene | 16.33 | 16.65 | 16.82 | 16.76 | 16.92 |
| M-Xylene | 39.38 | 38.68 | 38.77 | 39.06 | 39.16 |
| O-Xylene | 15.74 | 16.09 | 16.19 | 16.21 | 16.26 |
| 1,2,3 Trimethylbenzene | 0.72 | 0.74 | 0.78 | 0.81 | 0.80 |
| 1,2,4 Trimethylbenzene | 2.15 | 2.14 | 2.08 | 2.02 | 1.98 |
| 1,3,5 Trimethylbenzene | 0.18 | 0.14 | 0.12 | 0.11 | 0.10 |
| M & P Ethyl Toluene | 1.96 | 2.02 | 1.99 | 1.95 | 1.92 |
| O-Ethyl Toluene | 0.22 | 0.22 | 0.21 | 0.21 | 0.20 |
| $C_{10}$-Aromatics | 4.15 | 4.29 | 4.28 | 4.25 | 4.09 |
| M-Xylene Conversion | 53.05 | 53.89 | 53.75 | 53.39 | 53.29 |
| Ethylbenzene Conv. | 67.53 | 69.54 | 68.56 | 68.02 | 67.51 |
| Equilibration (P/PEQ) | 97.73 | 99.67 | 100.20 | 99.49 | 99.98 |
| Total Xylene Loss | 14.80 | 14.87 | 14.36 | 14.04 | 13.70 |
| % M-Xylene Isom. | 72.10 | 72.41 | 73.28 | 73.71 | 74.29 |
| % M-Xylene Loss | 27.90 | 27.59 | 26.72 | 26.29 | 25.71 |
| P/(P + O + M) | 22.86 | 23.31 | 23.44 | 23.27 | 23.39 |
| P/O Ratio | 1.04 | 1.03 | 1.04 | 1.03 | 1.04 |
| Wt. % $C_9+$ In Product | 13.97 | 13.95 | 13.91 | 13.83 | 13.49 |

TABLE XXVI (Example F)

| | | | |
|---|---|---|---|
| Time on Stream (Minutes) | 110 | 170 | 260 |
| Benzene | 9.53 | 9.76 | 9.43 |
| Toluene | 34.38 | 36.36 | 35.96 |
| Ethylbenzene | 1.35 | 0.86 | 0.88 |
| P-Xylene | 9.93 | 9.85 | 9.99 |
| M-Xylene | 23.71 | 22.76 | 23.27 |
| O-Xylene | 10.04 | 10.01 | 10.23 |
| 1,2,3 Trimethylbenzene | 0.00 | 0.26 | 0.22 |
| 1,2,4 Trimethylbenzene | 4.26 | 4.26 | 4.06 |
| 1,3,5 Trimethylbenzene | 0.56 | 0.45 | 0.34 |
| M & P Ethyl Toluene | 1.44 | 1.60 | 1.74 |
| O-Ethyl Toluene | 0.23 | 0.26 | 0.29 |
| $C_{10}$-Aromatics | 3.58 | 3.57 | 3.60 |
| M-Xylene Conversion | 58.04 | 59.79 | 58.82 |
| Ethylbenzene Conv. | 88.79 | 92.91 | 92.73 |
| % Equilibration | 99.89 | 99.98 | 99.97 |
| % M-Xylene Isom. | 60.91 | 58.69 | 60.83 |
| % M-Xylene Loss | 39.09 | 41.31 | 39.17 |
| P/(P + O + M) | 22.73 | 23.12 | 22.98 |
| P/O Ratio | 0.99 | 0.98 | 0.98 |
| Wt. % $C_9+$ In Product | 20.65 | 21.11 | 20.88 |

We claim:

1. An isomerization process for manufacture of xylenes from an initial feed stream comprising $C_8$ aromatics and containing xylenes which comprises contacting said feed stream with a catalyst containing at least one NZMS which has been either calcined, hydrotreated or chemically treated to remove at least a portion of the template used in the manufacture of the NZMS, or, alternatively, is calcined, hydrotreated or chemically treated in situ prior to carrying out the isomerization process at effective isomerization conditions to provide a selected xylene isomer in a greater concentration than the concentration of said xylene isomer initially in said feed stream wherein said NZMS is characterized in the calcined form by an absorption of isobutane of at least 2 percent by weight at a partial pressure of 500 torr and a temperature of 20° C. and is further characterized after removal of the template by an adsorption of triethylamine less than 5 percent by weight at a pressure of 2.6 torr and a temperature of 22° C.

2. In a process for conversion of a mixture of aromatic compounds having 8 carbon atoms, said mixture containing ethylbenzene and xylenes, to isomerize xylenes contained in said mixture and convert at least part of said ethylbenzene; the improvement which comprises contacting such mixture with a catalyst containing at least one NZMS catalyst which has been either calcined, hydrotreated or chemically treated to remove at least a portion of the template used in the manufacture of the NZMS, or, alternatively, is calcined, hydrotreated or chemically treated in situ prior to carrying out the isomerization process, in the presence of added hydrogen at effective process conditions to isomerize xylenes containing in said mixture and to convert at least part of said ethylbenzene, wherein said NZMS is characterized in the calcined form by an adsorption of isobutane of at least 2 percent by weight at a partial pressure of 500 torr and a temperature of 20° C. and is further characterized after removal of the template by an adsorption of triethylamine of less than 5 percent by weight at a pressure of 2.6 torr and a temperature of 22° C.

3. The process of claim 1 wherein said NZMS is characterized in the calcined form by an adsorption of isobutane of at least 4 percent by weight at a partial pressure of 500 torr and a temperature of 20° C.

4. The process of claim 2 wherein said NZMS is further characterized in its calcined form by an adsorption of isobutane of at least 4 percent by weight at a pressure of 500 torr and a temperature of 20° C.

5. The process of claim 1 or claim 2 wherein said NZMS is characterized in the calcined form by an adsorption of triethylamine of less than 3 percent by weight at a pressure of 2.6 torr and a temperature of 22° C.

6. The process of claim 1 or claim 2 wherein said catalyst contains an effective amount of at least one crystalline aluminosilicate or crystalline silicate to achieve isomerization or conversion, having activity for the isomerization of xylenes in a weight ratio between about 1:100 and about 100:1 of said zeolitic aluminosilicate to said NZMS molecular sieve and from 0 and about 99 weight percent of at least one inorganic oxide matrix component, based on the total weight of said catalyst.

7. The process of claim 6 wherein the inorganic oxide component is present in an amount between about 5 and about 95 percent by weight, based on the total weight of said catalyst.

8. The process of claim 2 wherein said effective process conditions include a temperature between about 500° F. to 1000° F.

9. The process of claim 8 wherein said effective process conditions include a temperature between about 650° F. and about 950° F.

10. The process of claim 1 or claim 2 wherein said NZMS has at least part of its cations as hydrogen or hydrogen-forming species.

11. The process of claim 10 wherein said hydrogen-forming species is $NH_4^+$.

12. The process of claim 2 wherein ethylbenzene is converted to a xylene.

13. The process of 7 wherein said inorganic oxide matrix component is selected from the group consisting of clays, silicas, aluminas, and mixtures thereof.

14. The process of claim 1 or claim 2 wherein said NZMS is a SAPO.

15. The process of claim 1 or claim 2 wherein said NZMS is selected from the group consisting of CoAPSOs, FeAPSOs, MgAPSOs, MnAPSOs, TiAPSOs, ZnAPSOs, CoMgAPSOs, CoMnMgAPSOs, MeAPOs, TAPOs, FAPOs and mixture thereof.

16. The process of claim 1 or claim 2 wherein said NZMS is selected from the group consisting of CoAPSOs, FeAPSOs, MgAPSOs, MnAPSOs, TiAPSOs, ZnAPSOs, CoMgAPSOs, CoMnMgAPSOs and mixtures thereof.

17. The process of claim 1 or claim 2 wherein said NZMS is selected from the group consisting of ELAPSO-11, ELAPSO-31, ELAPSO-41, and mixtures thereof.

18. The process of claim 17 wherein said NZMS is selected from the group consisting of CoAPSO-11, CoAPSO-31, CoAPSO-41, FeAPSO-11, FeAPSO-31, FeAPSO-41, MgAPSO-11, MgAPSO-31, MgAPSO-41, MnAPSO-11, MnAPSO-31, MnAPSO-41, SAPO-11, SAPO-31, SAPO-41, TiAPSO-11, TiAPSO 31, TiAPSO-41, ZnAPSO-11, ZnAPSO-31, ZnAPSO-41, CoMgAPSO-11, CoMgAPSO-31, CoMgAPSO-41, CoMnMgAPSO-11, CoMnMgAPSO-31, CoMnMgAPSO-41 and mixtures thereof.

19. The process of claim 1 or claim 2 wherein said NZMS is selected from the group consisting of MeAPO-11, MeAPO-31, MeAPO-41, TAPO-11, TAPO-31, TAPO-41, FAPO-11, FAPO-31, FAPO-41 and mixtures thereof.

20. The process of claim 19 wherein "Me" is selected from the group consisting of cobalt magnesium, manganese and mixtures thereof.

21. The process of claim 19 wherein "Me" is selected from the group consisting of magnesium, manganese and mixtures thereof.

22. The process of claim 6 wherein said zeolitic aluminosilicate is selected from the group consisting of ferrierite, silicalite, ZSM-type zeolites and mixtures thereof.

23. The process of claim 2 wherein an effective amount of hydrogen is present and said catalyst contains an effective amount of at least one dehydrogenation catalyst to isomerized xylenes contained in said mixture and to convert at least part of said ethylbenzene.

24. The process of claim 23 wherein the hydrogenation component is selected from the group consisting of Pd, Pt, Ni and mixtures thereof.

25. The process of claim 24 wherein said hydrogenation component is present in an effective amount between 0.05 and about 3.0 wt. percent of at least one of Pd and Pt.

26. The process of claim 24 wherein the hydrogenation component is Ni and is present in an effective amount between about 0.05 and about 5.0 weight percent.

27. The process of claim 1 wherein said initial feed stream comprises m-xylene and said product contains a greater concentration of para-xylene than said initial feedstream.

28. The process of claim 1 wherein said product contains a greater concentration of o-xylene than said initial feed stream.

29. The process of claim 1 wherein said product contains a greater concentration of m-xylene than said initial feed stream.

30. The process of claim 1 wherein said initial feed stream contains ethylbenzene.

* * * * *